(12) United States Patent
Marshall et al.

(10) Patent No.: US 8,200,462 B2
(45) Date of Patent: Jun. 12, 2012

(54) DENTAL APPLIANCES

(75) Inventors: Michael Craig Marshall, Prior Lake, MN (US); Brian Paul Wallenfelt, Plymouth, MN (US); Minh Xuan Nguyen, St. Paul, MN (US)

(73) Assignee: GeoDigm Corporation, Chanhassen, MN (US)

( * ) Notice: Subject to any disclaimer, the term of this patent is extended or adjusted under 35 U.S.C. 154(b) by 562 days.

(21) Appl. No.: 12/013,194

(22) Filed: Jan. 11, 2008

(65) Prior Publication Data

US 2008/0220395 A1    Sep. 11, 2008

Related U.S. Application Data

(60) Provisional application No. 60/879,905, filed on Jan. 11, 2007.

(51) Int. Cl.
*G06G 7/48* (2006.01)
*G06G 7/58* (2006.01)

(52) U.S. Cl. .............................. 703/6; 703/11
(58) Field of Classification Search ............ 703/6, 11
See application file for complete search history.

(56) References Cited

U.S. PATENT DOCUMENTS

| | | | |
|---|---|---|---|
| 1,733,895 A | 10/1929 | Matteson, Jr. |
| 2,194,790 A | 3/1940 | Glück |
| 3,807,862 A | 4/1974 | Hatzenbuhler |
| 4,081,019 A | 3/1978 | Kulig |
| 4,206,545 A | 6/1980 | Lord |
| 4,273,580 A | 6/1981 | Shoher et al. |
| 4,411,626 A | 10/1983 | Becker et al. |
| 4,611,288 A | 9/1986 | Duret et al. |
| 4,663,720 A | 5/1987 | Duret et al. |
| 4,741,378 A | 5/1988 | Engelman et al. |
| 4,742,464 A | 5/1988 | Duret et al. |
| 4,778,386 A | 10/1988 | Spiry |
| 4,844,144 A | 7/1989 | Murphy et al. |
| 4,850,873 A | 7/1989 | Lazzara et al. |
| 4,869,666 A | 9/1989 | Talass |
| 4,937,928 A | 7/1990 | van der Zel |
| 4,952,149 A | 8/1990 | Duret et al. |
| 4,972,897 A | 11/1990 | Thomas |
| 5,004,037 A | 4/1991 | Castaldo |

(Continued)

FOREIGN PATENT DOCUMENTS

DE    36 26 789 A1    2/1988

(Continued)

OTHER PUBLICATIONS

Seymour et al., "Assessment of shoulder dimensions and angles of porcelain bonded to metal crown preparations," *The Journal of Prosthetic Dentistry* (1996) 75: 406-411.

(Continued)

*Primary Examiner* — David Silver
(74) *Attorney, Agent, or Firm* — Merchant & Gould P.C.

(57) ABSTRACT

Electronic models of components of dental appliances can be generated based on the outer surface of an electronic model of the dental appliance. The outer surface may be generated based on the dentition and anatomy of the patient. For example, automated processes may identify landmarks in the anatomy and define the outer surface based on the identified landmarks. Alternatively, the outer surface may be generated based on statistical data. A management system coordinates automated processes with interactive processes to facilitate collaboration of remotely located technicians and equipment in generating electronic models.

8 Claims, 44 Drawing Sheets

U.S. PATENT DOCUMENTS

| | | | |
|---|---|---|---|
| 5,011,405 | A | 4/1991 | Lemchen |
| 5,027,281 | A | 6/1991 | Rekow et al. |
| 5,092,022 | A | 3/1992 | Duret |
| 5,121,333 | A | 6/1992 | Riley et al. |
| 5,139,419 | A | 8/1992 | Andreiko et al. |
| 5,232,361 | A | 8/1993 | Sachdeva et al. |
| 5,237,998 | A | 8/1993 | Duret et al. |
| 5,257,203 | A | 10/1993 | Riley et al. |
| 5,273,429 | A | 12/1993 | Rekow et al. |
| 5,338,198 | A | 8/1994 | Wu et al. |
| 5,368,478 | A | 11/1994 | Andreiko et al. |
| 5,378,154 | A | 1/1995 | van der Zel |
| 5,431,562 | A | 7/1995 | Andreiko et al. |
| 5,447,432 | A | 9/1995 | Andreiko et al. |
| 5,454,717 | A | 10/1995 | Andreiko et al. |
| RE35,169 | E | 3/1996 | Lemchen et al. |
| 5,518,397 | A | 5/1996 | Andreiko et al. |
| 5,588,832 | A | 12/1996 | Farzin-Nia |
| 5,683,243 | A | 11/1997 | Andreiko et al. |
| 5,690,490 | A | 11/1997 | Cannon et al. |
| 5,725,376 | A | 3/1998 | Poirier |
| 5,735,692 | A | 4/1998 | Berger |
| 5,909,765 | A | 6/1999 | McDowell |
| 6,015,289 | A | 1/2000 | Andreiko et al. |
| 6,042,374 | A | 3/2000 | Farzin-Nia et al. |
| 6,049,743 | A * | 4/2000 | Baba .......................... 700/163 |
| RE36,863 | E | 9/2000 | Snyder |
| 6,152,731 | A | 11/2000 | Jordan et al. |
| 6,174,168 | B1 | 1/2001 | Dehoff et al. |
| 6,177,034 | B1 | 1/2001 | Ferrone |
| 6,217,334 | B1 | 4/2001 | Hultgren |
| 6,227,850 | B1 | 5/2001 | Chishti et al. |
| 6,283,753 | B1 | 9/2001 | Willoughby |
| 6,287,121 | B1 | 9/2001 | Guiot et al. |
| 6,287,490 | B2 | 9/2001 | Rheinberger et al. |
| 6,322,728 | B1 | 11/2001 | Brodkin et al. |
| 6,354,836 | B1 | 3/2002 | Panzera et al. |
| 6,371,761 | B1 | 4/2002 | Cheang et al. |
| 6,398,554 | B1 | 6/2002 | Perot et al. |
| 6,409,504 | B1 | 6/2002 | Jones et al. |
| 6,460,594 | B1 | 10/2002 | Lam |
| 6,463,344 | B1 | 10/2002 | Pavloskaia et al. |
| 6,506,054 | B2 | 1/2003 | Shoher et al. |
| 6,532,299 | B1 | 3/2003 | Sachdeva et al. |
| 6,568,936 | B2 | 5/2003 | MacDougald et al. |
| 6,575,751 | B1 | 6/2003 | Lehmann et al. |
| 6,648,640 | B2 | 11/2003 | Rubbert et al. |
| 6,648,645 | B1 | 11/2003 | MacDougald et al. |
| 6,662,112 | B2 | 12/2003 | Prasad et al. |
| 6,667,112 | B2 | 12/2003 | Prasad et al. |
| 6,691,764 | B2 | 2/2004 | Embert et al. |
| 6,835,066 | B2 | 12/2004 | Iiyama et al. |
| 6,915,178 | B2 | 7/2005 | O'Brien et al. |
| 7,228,191 | B2 | 6/2007 | Hofmeister et al. |
| 7,463,942 | B2 | 12/2008 | O'Brien et al. |
| 7,735,542 | B2 | 6/2010 | Marshall et al. |
| 2002/0015934 | A1 | 2/2002 | Rubbert et al. |
| 2002/0028425 | A1 | 3/2002 | Hurson |
| 2002/0064759 | A1 | 5/2002 | Durbin et al. |
| 2002/0110786 | A1 | 8/2002 | Dillier |
| 2004/0121291 | A1 | 6/2004 | Knapp et al. |
| 2004/0137408 | A1 | 7/2004 | Embert et al. |
| 2004/0204787 | A1 | 10/2004 | Kopelman et al. |
| 2004/0220691 | A1 * | 11/2004 | Hofmeister et al. ............. 700/98 |
| 2004/0265770 | A1 | 12/2004 | Chapoulaud et al. |
| 2005/0177261 | A1 | 8/2005 | Durbin et al. |
| 2005/0177266 | A1 | 8/2005 | Kopelman et al. |
| 2005/0236551 | A1 | 10/2005 | Lee |
| 2005/0251281 | A1 | 11/2005 | O'Brien et al. |
| 2006/0106484 | A1 | 5/2006 | Saliger et al. |
| 2006/0115793 | A1 | 6/2006 | Kopelman et al. |
| 2006/0115795 | A1 | 6/2006 | Marshall et al. |
| 2006/0122719 | A1 | 6/2006 | Kopelman et al. |
| 2008/0131846 | A1 | 6/2008 | Marshall et al. |
| 2008/0142183 | A1 | 6/2008 | Marshall et al. |
| 2009/0087818 | A1 | 4/2009 | O'Brien et al. |
| 2009/0148816 | A1 | 6/2009 | Marshall et al. |

FOREIGN PATENT DOCUMENTS

| | | |
|---|---|---|
| EP | 0 316 106 A1 | 5/1989 |
| EP | 0 322 257 A2 | 6/1989 |
| EP | 0 426 363 A2 | 5/1991 |
| EP | 0 502 227 B1 | 11/1996 |
| EP | 0 781 625 A1 | 7/1997 |
| EP | 1 006 931 B1 | 6/2000 |
| FR | 2 593 384 A1 | 1/1986 |
| GB | 2 296 673 A | 7/1996 |
| JP | 5049651 A | 3/1993 |
| JP | 10-118097 | 5/1998 |
| KR | 10-2008-0030016 | 4/2008 |
| WO | WO 94/10935 | 5/1994 |
| WO | WO 95/15731 | 6/1995 |
| WO | WO 02/19940 A1 | 3/2002 |
| WO | WO 02/076327 A1 | 10/2002 |

OTHER PUBLICATIONS

Sohmura et al., "Use of CAD/CAM system to fabricate dental prostheses. Part 1: CAD for a clinical crown restoration," *The International Journal of Prosthodontics* (1995) 8 (3): 252-258.

Lewis, J., "Software beefs up tractor radiator-guard mount," *Design News*, vol. 54, No. 4, pp. 87-88 (Feb. 15, 1999) (1 page abstract).

Rotert, V., "How one rapid prototyping method is able to eliminate tooling for investment casting," *Proceedings of the 45th Annual Technical Meeting and Exhibition Investment Casting Institute*, Atlanta, Georgia (1997) (1 page abstract).

Weeden, B. et al., "Alternative methods for custom implant production utilizing a combination of rapid prototyping technology and conventional investment casting," *Proceedings of the 1996 15th Southern Biomedical Engineering Conference*, Dayton, Ohio (1996) (1 page abstract).

Wirtz, H. et al., "Investment casting shells in 1 day using selective laser sintering (SLS)," *Proceedings of the 24th BICTA Conference on Investment Casting*, Oxford, GB (1999) (1 page abstract).

Wu, M. et al., "Application of rapid prototyping and numerical simulation in titanium dental castings," *Computer Assisted Surgery & Rapid Prototyping in Medicine*, 5th Int. Workshop (1999) (1 page abstract).

Frank Hermanek, Finding The Lost Wax Process, Jan.-Feb. 2002, pp. 5 & 7.

www.cranstoncasting.com/process.htm.

International Search Report and Written Opinion mailed Jul. 30, 2008.

Cad Cam Ventures, Auto-Milled Crown and the Cad Cam Ventures, 13 pages (Feb. 1999).

Cicero, It's Time for Digital Solutions, Brochure, 12 pages (Apr. 1999).

DCS Dental AG, The Precident System, 16 pages (Apr. 1999).

Dental Laboratory Technology, Fixed Restorative Techniques, Section 13 Spruing and Investing, pp. 149-180 pages (1972).

Dentalmatic Technologies, Inc., "Premiering a Dental Lab Tool that Eliminates Waxing, Investing, Casting, Increases Productivity and Improves Labor Efficiency," 8 pages (Publicly known at least as early as Sep. 6, 2000).

Denzir, "Denzir—for Superior Dental Restorations!," 14 pages (Publicly known at least as early as Sep. 6, 2000).

Model Maker II, Sanders Prototype, Inc., The High Precision 3-D Modeling System, Brochure, 10 pages (Jul. 2000).

Tamura, K., "Procelain-Fused-to-Metal Crowns," *Essential of Dental Technology*, pp. 356-359 (1987).

International Search Report and Written Opinion cited in International Application No. PCT/US2009/067350 mailed Aug. 18, 2010.

Non-Final Office Action mailed Nov. 16, 2011 for U.S. Appl. No. 12/956,857.

Final Office Action mailed Dec. 8, 2011 for U.S. Appl. No. 11/958,484.

* cited by examiner

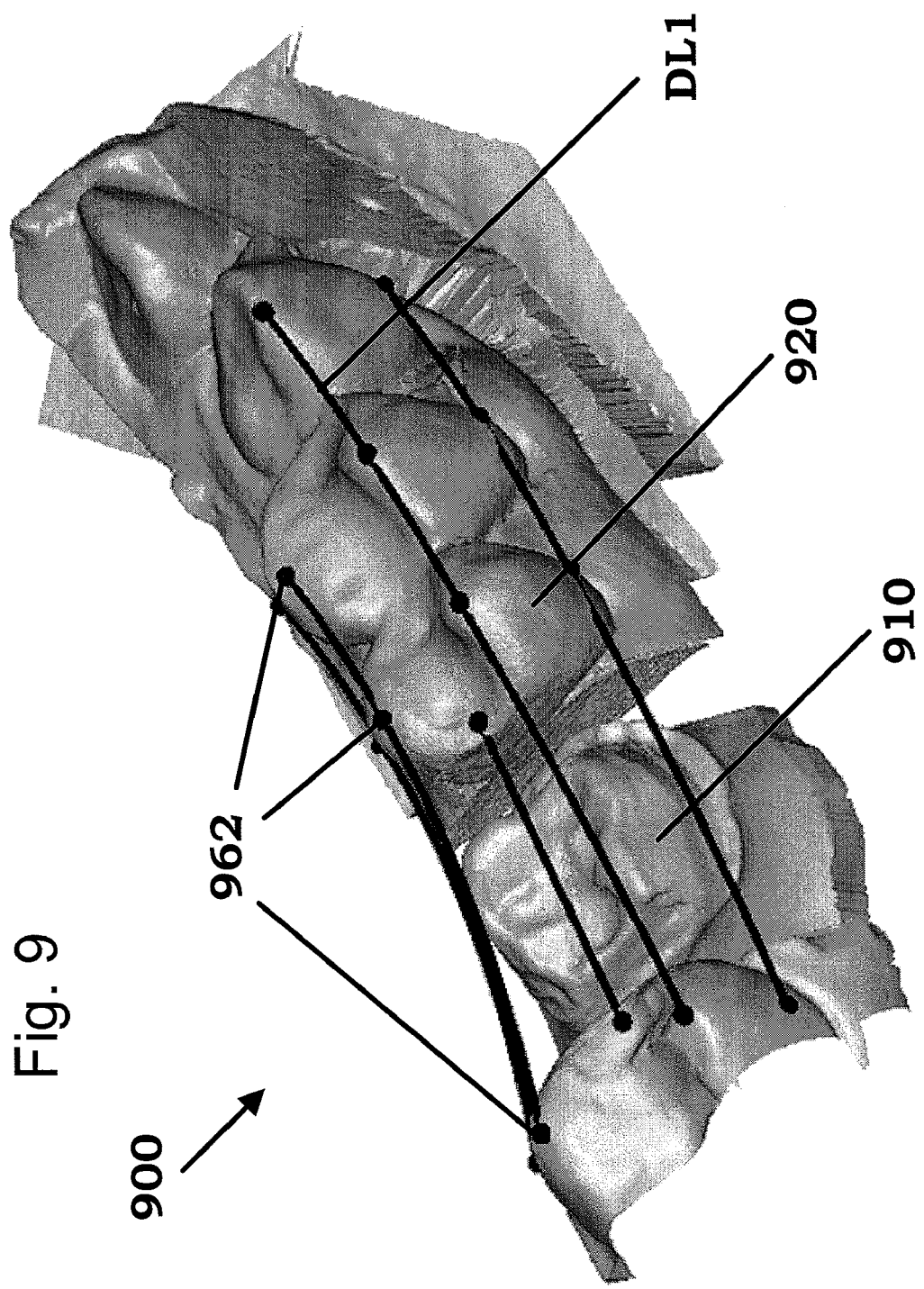

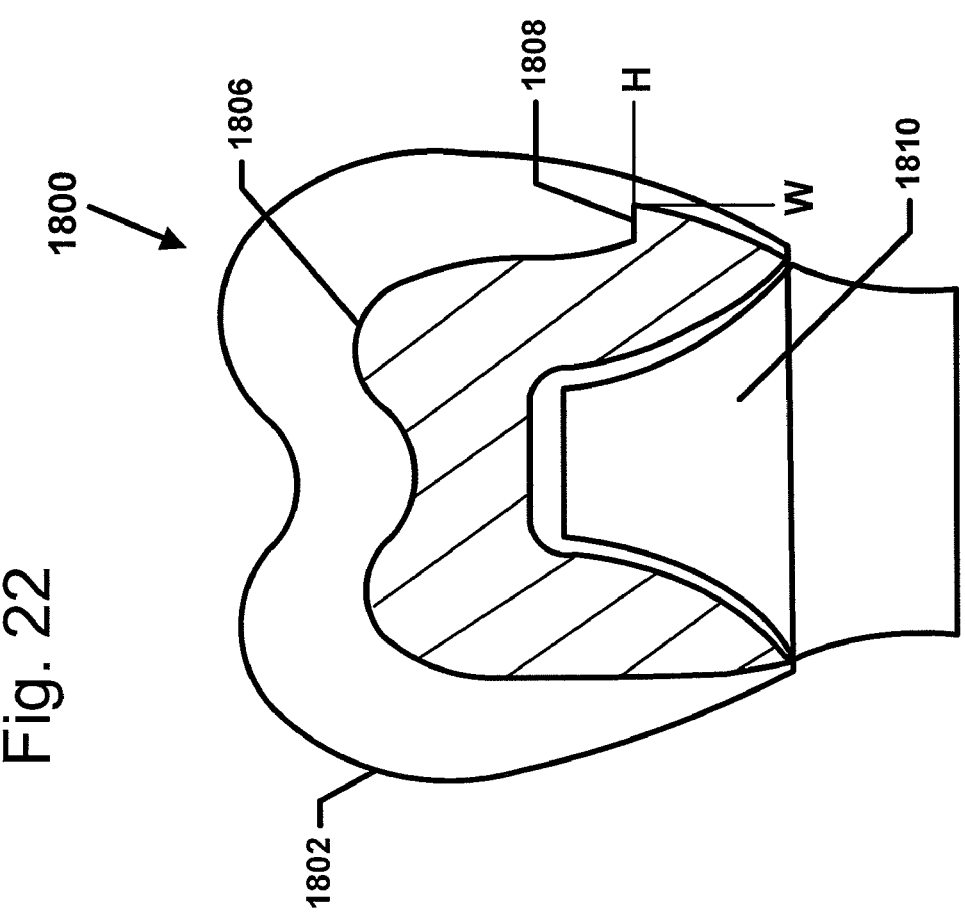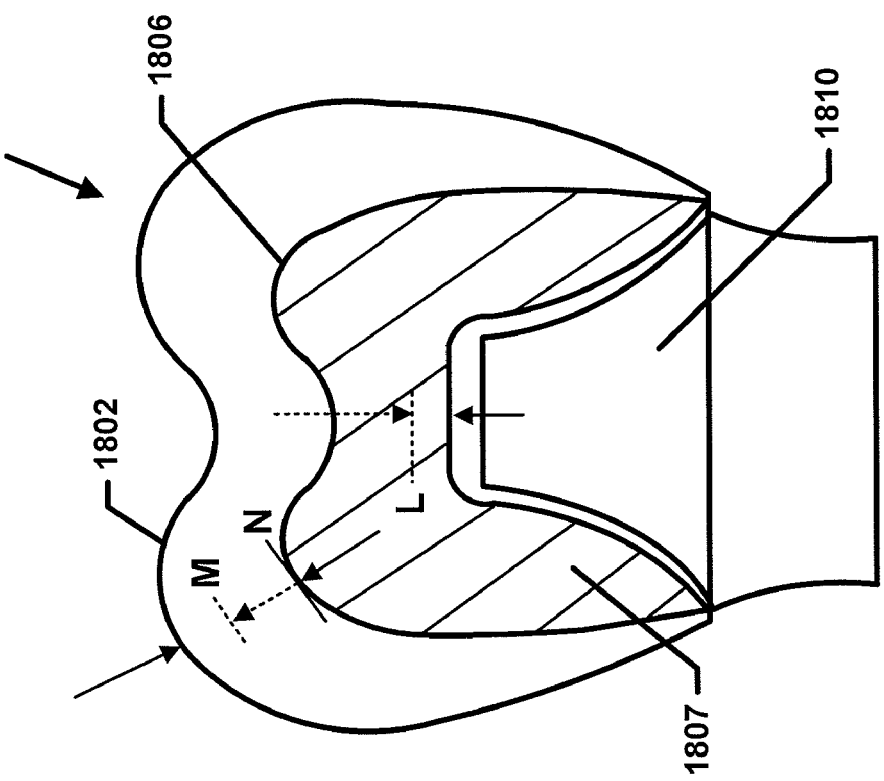

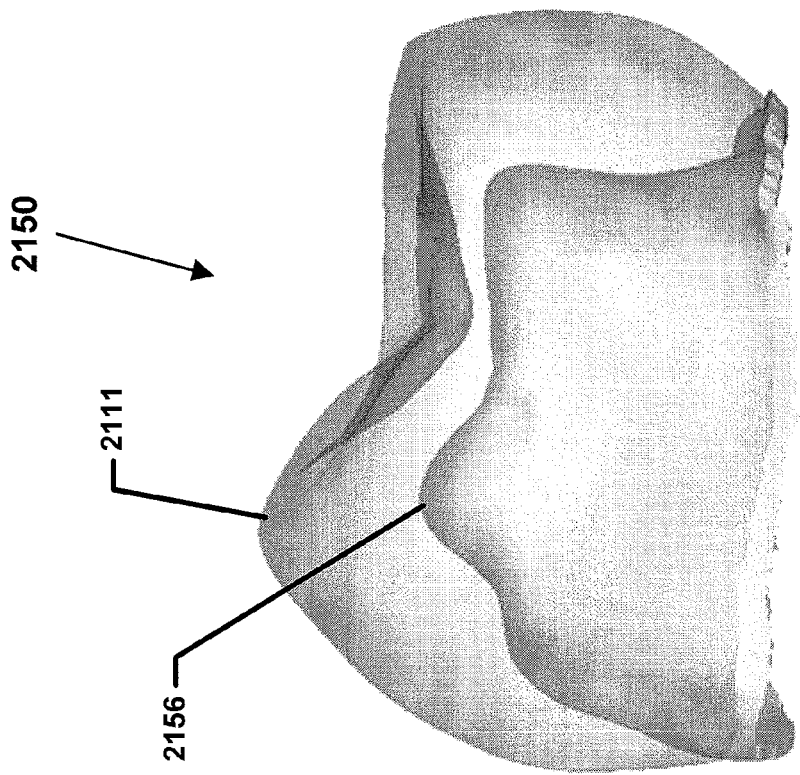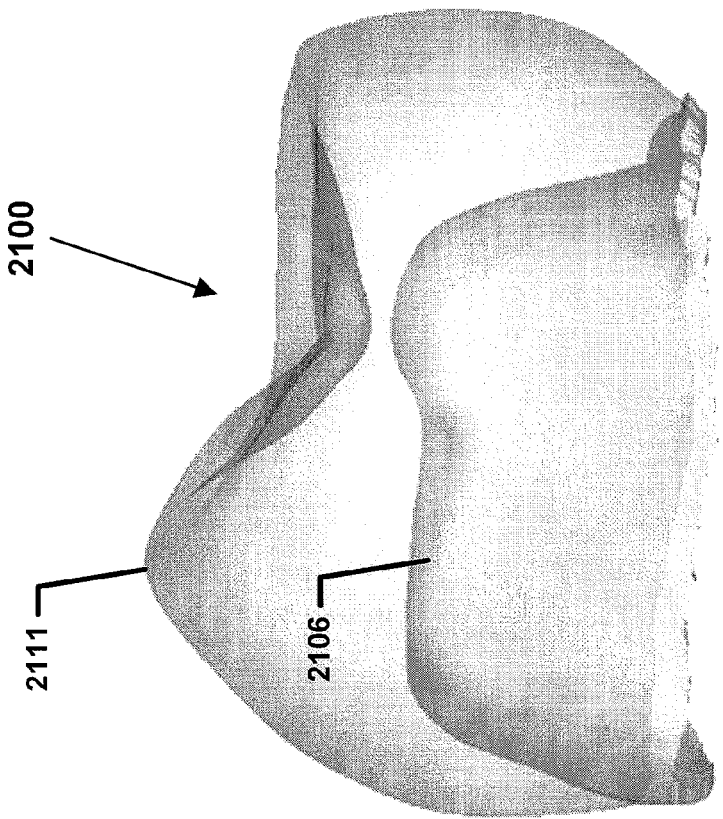
FIG. 21

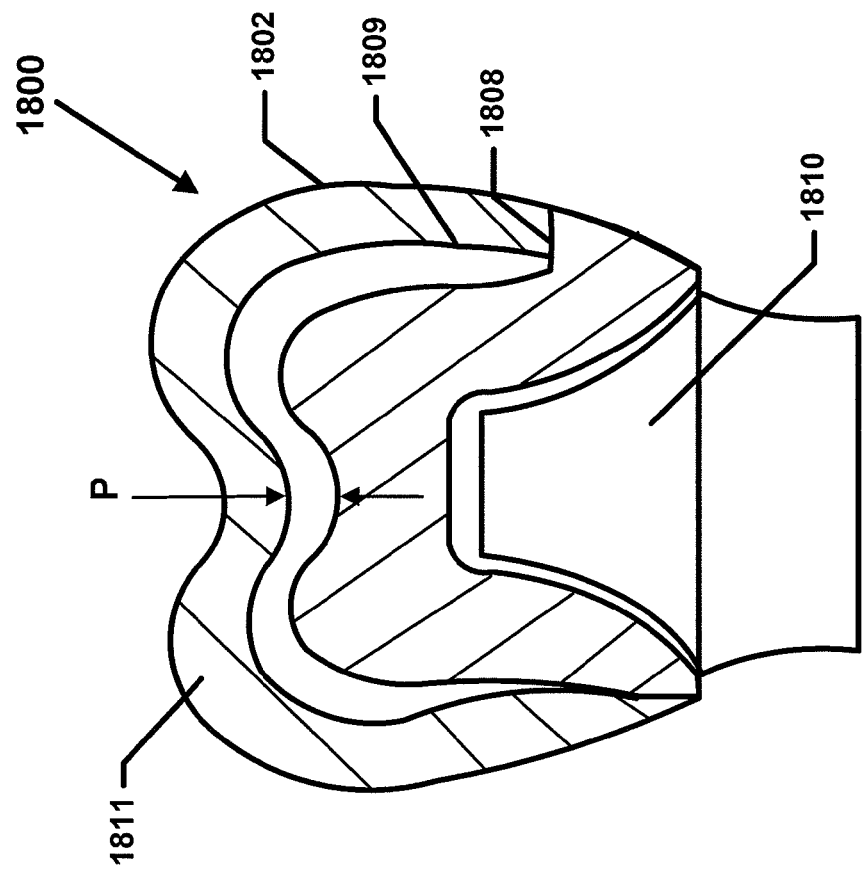
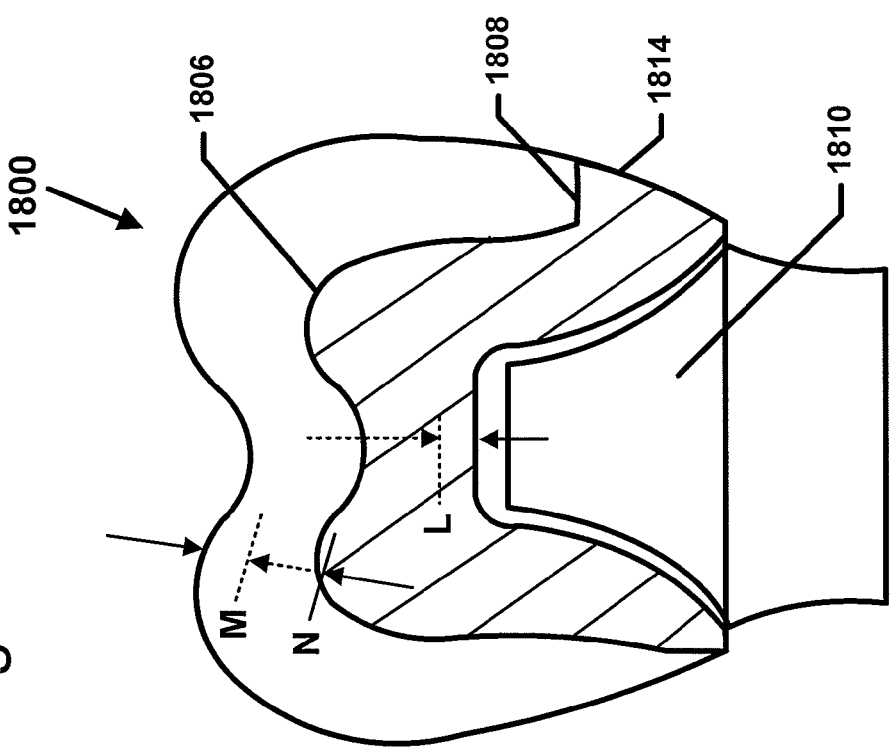

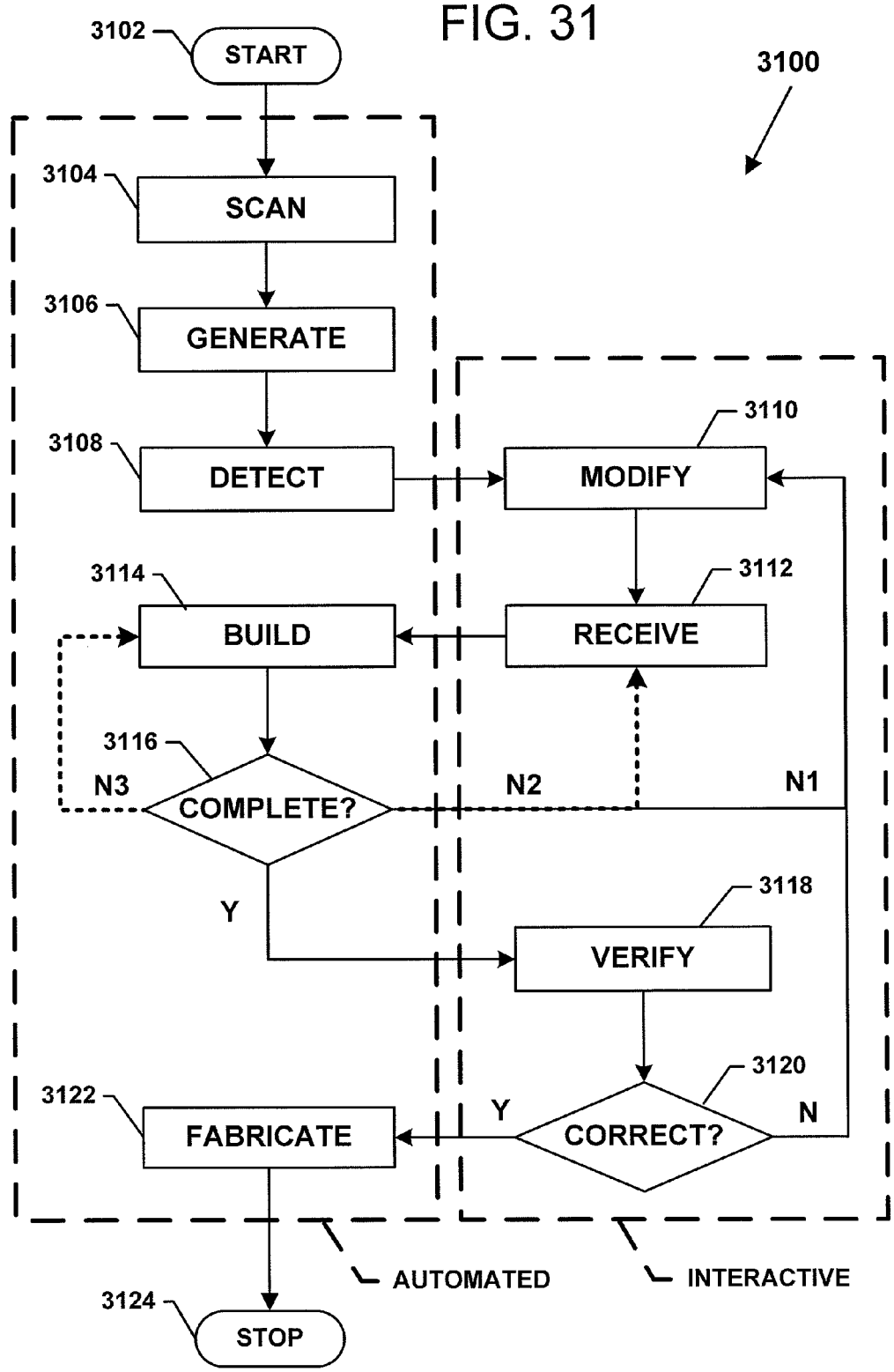

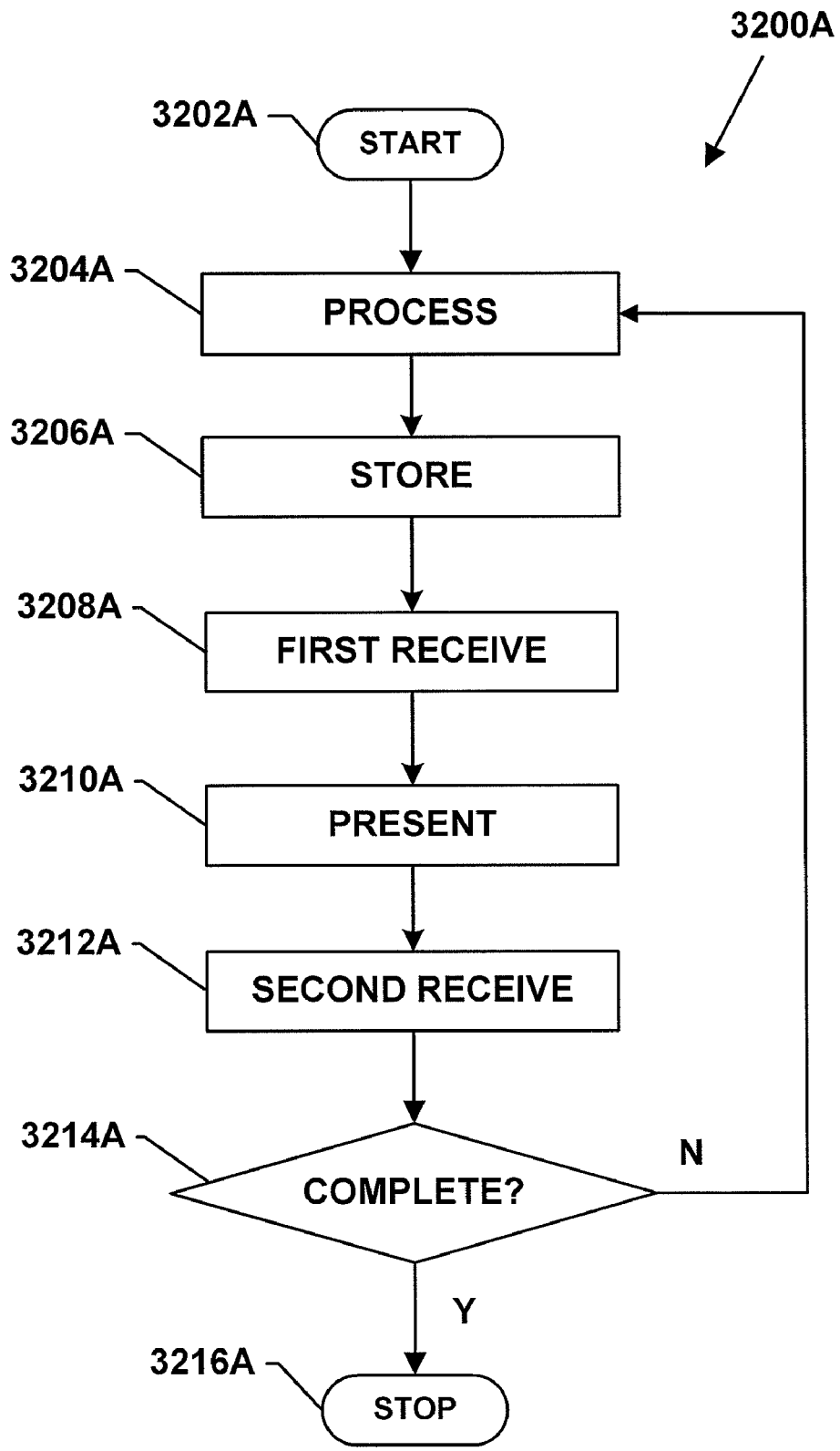

DENTAL APPLIANCES

CROSS REFERENCE TO RELATED APPLICATIONS

This application claims priority to U.S. Provisional Application Ser. No. 60/879,905, filed Jan. 11, 2007, entitled "DESIGN OF DENTAL APPLIANCES," the disclosure of which is hereby incorporated by reference herein.

BACKGROUND

Computer based systems that allow the creation and use of electronic models of teeth to design some types of dental appliances have been developed over time. Electronic models of dental appliances are designed to fit within the patient's mouth and then fabricated to produce the appliance or a pattern used in casting the appliance.

Dental appliances include, by way of illustration, restorations, bridges, and implants. Restorations include, by way of illustration, replacements for single teeth including incisors, molars, and pre-molars. Dental appliances are designed to mount to either natural teeth or implanted teeth substitutes. For the sake of convenience, this disclosure will use the term "preparation site" to refer to a site at which a dental appliance is to be mounted, regardless of whether the site is a natural tooth or an implanted tooth substitute.

In some prior systems, an electronic model for a dental appliance is designed to complement an electronic image of a preparation site. The electronic image of the preparation site can be generated based on a patient's actual preparation site (e.g., through intra-oral imaging) or a casting thereof (e.g., a dental study cast). In an embodiment, the electronic model of the dental appliance is generated based on an electronic image of a neighboring tooth. The electronic image is then edited to fit on the preparation site.

In another embodiment, a standard electronic model is obtained from an image library. The electronic model can be edited manually using an interactive computer graphics program. For example, sections of the electronic model can be selected and dragged into desired shapes using standard graphic editing techniques. New lines or sections can be added and undesired sections can be deleted from the electronic model. Such editing can be time-consuming and depends on the skill of the technician to create a visually pleasing dental appliance that will fit the space.

It is with respect to these and other considerations that the present invention has been made.

SUMMARY

This disclosure is directed generally to methods and systems for designing dental appliances. The invention enables a user to efficiently design dental appliances customized for the patient. Once designed, these dental appliances can be fabricated and installed on a patient.

According to aspects, electronic models of components of a dental appliance can be generated based on an electronic model of the dental appliance.

According to other aspects, electronic models of dental appliances and/or components thereof may be generated based on the dentition and anatomy of the patient.

According to other aspects, electronic models of dental appliances and/or components thereof may be generated based on statistical data.

A management system configured in accordance with principles of the present disclosure monitors automated processes and interactive processes to facilitate interaction among skilled technicians and computer processors.

While the invention will be described with respect to preferred embodiment configurations and with respect to particular structures used therein, it will be understood that the invention is not to be construed as limited in any manner by either such configurations or structures described herein. Rather, the invention is defined in the claims attached hereto.

Further, it will be appreciated that the present invention need not include each and every one of the features described herein. Instead, methods and assemblies constructed in accordance with the principles of the present invention may utilize one or more of the identified features.

BRIEF DESCRIPTION OF THE DRAWINGS

FIG. 9 illustrates an exemplary electronic model of a preparation site over which diagramming lines have been positioned in accordance with the principles of the present disclosure;

FIGS. 18-24 are schematic diagrams illustrating an electronic model of a dental restoration generated using the design process of FIG. 17 at different stages of the design process;

FIG. 31 is a flowchart illustrating an operational flow for an exemplary design and fabrication process by which dental appliances may be designed and fabricated in accordance with the principles of the present disclosure;

FIG. 32A is a flowchart illustrating an operational flow for an exemplary management process by which one or more processors may implement steps of the design and fabrication process of FIG. 31 in accordance with the principles of the present disclosure;

DETAILED DESCRIPTION

In the following detailed description, reference is made to the accompanying drawings, which form a part hereof, and in which are shown specific embodiments or examples by way of illustration. The embodiments described herein may be combined and other embodiments may be utilized without departing from the spirit or scope of the present disclosure. The following detailed description, therefore, is not to be taken in a limiting sense. The scope of the invention is defined by the appended claims and their equivalents.

In general, this disclosure is directed to designing dental appliances. Once designed, the dental appliances are fabricated and installed on a preparation site of a patient. Components of one system configured in accordance with the principles of the disclosure include a computing system, on which electronic models (e.g., polygonal, mesh-based, electronic models) can be processed, and software modules configured to generate and/or edit the electronic models.

Using electronic models to represent components of dental appliances enables a user to control and manipulate the interaction of these components before the dental appliance is fabricated. Consequently problems that may arise during interaction may be eliminated before a significant amount of fabrication material or labor is expended. Furthermore, all components of the dental appliance may be specified as to shape, size, and orientation to form complementary surfaces. For example, electronic models can be used to form a dental restoration having a cooperating coping substructure and crown structure.

Figure 1:
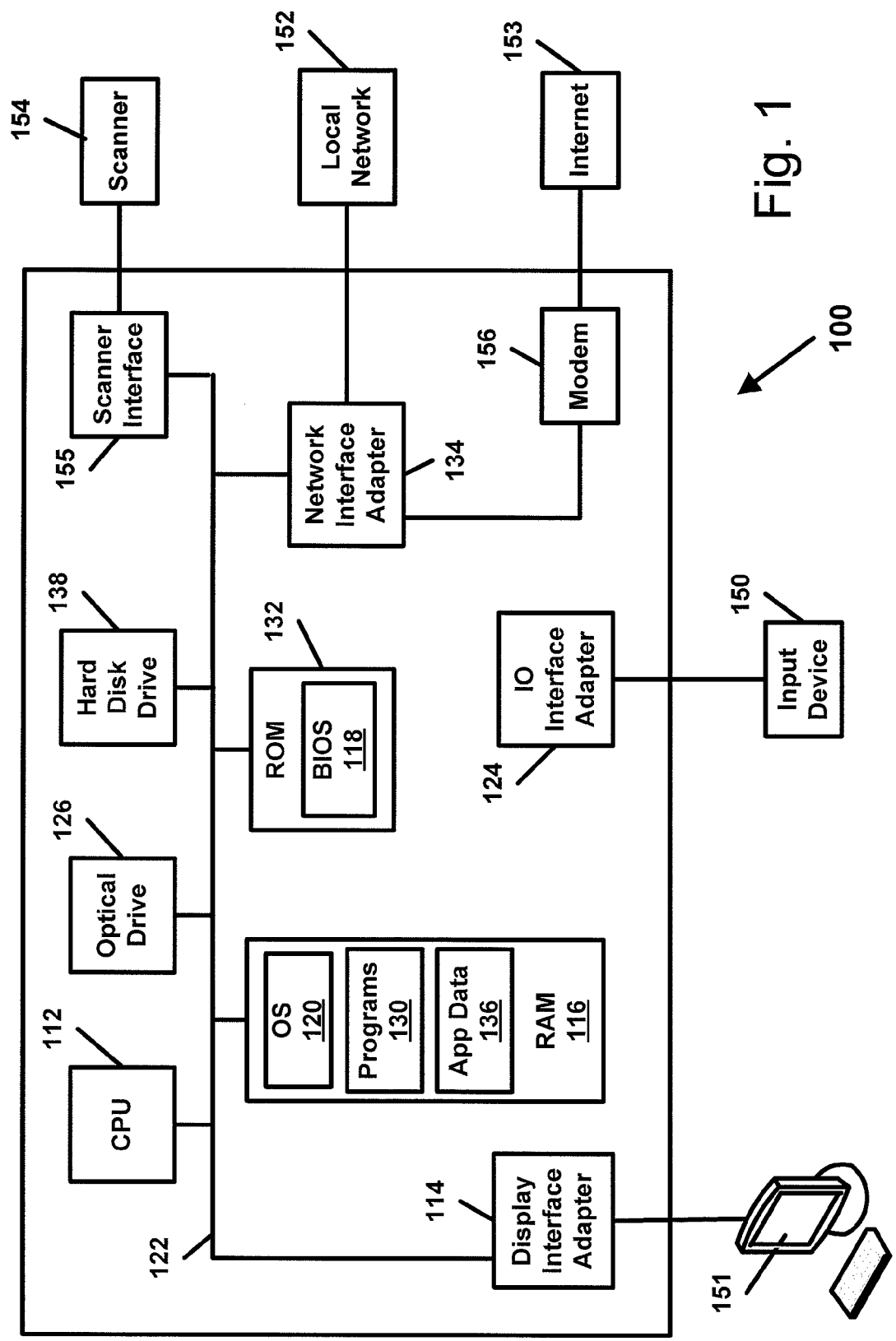
FIG. 1 is a block diagram of a general purpose computing system for use in implementing one or more computing embodiments of the disclosure.

One example general-purpose computing system for implementing the disclosure is shown in FIG. 1 in the form of a conventional personal computer 100. In other embodiments, however, other types of computing systems can be used. The computer 100 includes a processor unit 112, read only memory (ROM) 132, random access memory (RAM) 116, and a system bus 122 that couples various system components including the RAM 116 to the processor unit 112. The system bus 122 may be any of several types of bus structures including a memory bus or memory controller, a peripheral bus and a local bus using any of a variety of bus architectures. A basic input/output system 118 (BIOS), which contains basic routines that help transfer information between elements within the personal computer 100, is stored in ROM 132.

The personal computer 100 further includes a hard disk drive 138 for reading from and writing to a hard disk (not shown), a magnetic disk drive (not shown) for reading from or writing to a removable magnetic disk, and an optical disk drive 126 for reading from or writing to a removable optical disk such as a CD ROM, DVD, or other optical media. The hard disk drive 138, magnetic disk drive, and optical disk drive 126 are connected to the system bus 122 by a hard disk drive interface (not shown), a magnetic disk drive interface (not shown), and an optical drive interface (not shown), respectively. The drives and their associated computer-readable media provide nonvolatile storage of computer readable instructions, data structures, programs, and other data for the personal computer 100.

Although the exemplary environment described herein employs a hard disk drive 138, a removable magnetic disk, and removable optical disk drive 126, other types of computer-readable media capable of storing data can be used in the exemplary system. Examples of these other types of computer-readable mediums that can be used in the exemplary operating environment include magnetic cassettes, flash memory cards, digital video disks, Bernoulli cartridges, random access memories (RAMs), and read only memories (ROMs).

A number of program modules may be stored on the hard disk drive 138, magnetic disk drive, optical disk drive 126, ROM 332 or RAM 316, including an operating system 120, one or more application programs 130, other program modules (not shown), and program (i.e., application) data 136. A user may enter commands and information into the personal computer 100 through input devices such as a keyboard and/or mouse 150 (or other pointing device). Examples of other input devices may include a microphone, joystick, game pad, satellite dish, and scanner. These and other input devices are often connected to the processing unit 112 through an I/O port interface 124 that is coupled to the system bus 122. Nevertheless, these input devices also may be connected by other interfaces, such as a parallel port, game port, or a universal serial bus (USB). A monitor 151 or other type of display device is also connected to the system bus 122 via an interface, such as a video adapter 114. In addition to the monitor, personal computers typically include other peripheral output devices (not shown), such as speakers and printers.

The personal computer 100 may operate in a networked environment using logical connections to one or more remote computers. The remote computer may be another personal computer, a server, a router, a network PC, a peer device or other common network node, and typically includes many or all of the elements described above relative to the personal computer 100. The network connections include a local area network (LAN) and a wide area network (WAN). Such networking environments are commonplace in offices, enterprise-wide computer networks, intranets, and the Internet.

When used in a LAN networking environment, the personal computer 100 is connected to the local network 152 through a network interface or adapter 110. When used in a WAN networking environment, the personal computer 100 typically includes a modem or other means for establishing communications over the wide area network, such as the Internet 153. The modem 156, which may be internal or external, is connected to the system bus 122 via the network interface adapter 134. In a networked environment, program modules depicted relative to the personal computer 100, or portions thereof, may be stored in the remote memory storage device. It will be appreciated that the network connections shown are exemplary only and other means of establishing a communications link between the computers may be used.

A scanner 154 can be connected to the computer 100 via an appropriate scanner interface 155. The scanner interface 155 can be connected to the bus 122 such that the scanned data may be stored in the appropriate or desired memory location, manipulated by the CPU 112, displayed on the display 151, etc. Preferred scanners include a laser line scanner arranged and configured for scanning dental study casts. However, any suitable scanner may be used and a number of other methodologies might be employed to generate the scanned image data.

Portions of the preferred embodiment constructed in accordance with the principles of the present invention utilize a computer and are described herein as implemented by logical operations performed by a computer. The logical operations of these various computer implemented processes are generally performed either (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

Figure 2:
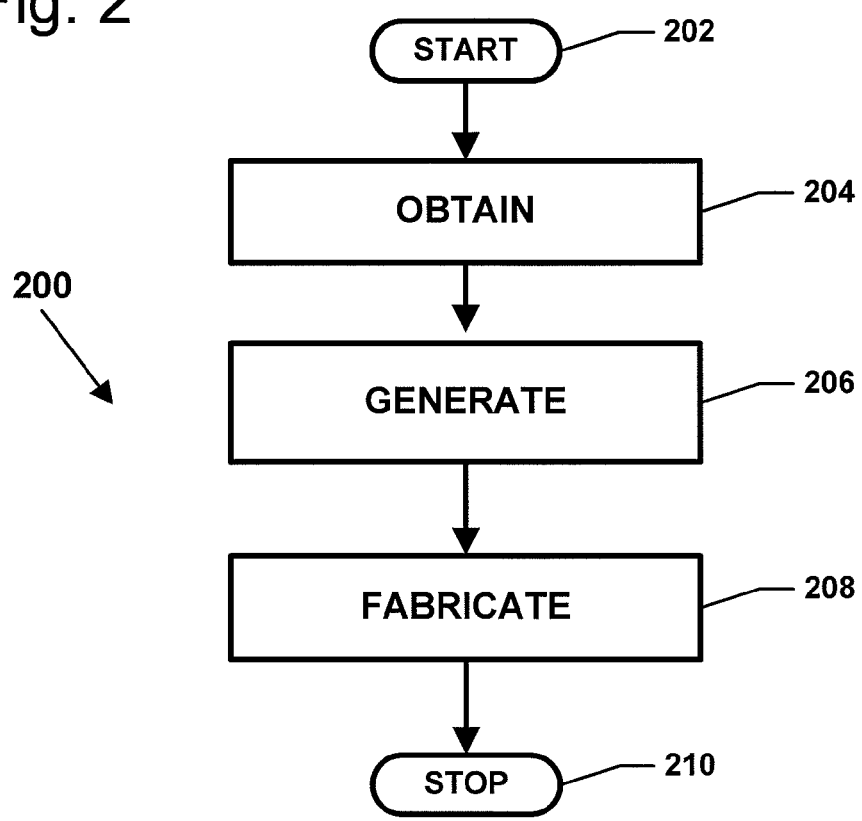
FIG. 2 is a flowchart illustrating an operational flow for a creation process for creating a dental appliance in accordance with the principles of the present disclosure.

FIG. 2 is a flowchart illustrating an operational flow for a creation process 200 for creating a dental appliance in accordance with the principles of the present disclosure. The creation process 200 is used generally to design and fabricate a customized dental appliance (e.g., a dental crown, a dental bridge, or a dental implant) configured to mount to a preparation site within a patient's mouth. The creation process 200 initializes and begins at a start module 202 and proceeds to an obtain operation 204.

Figure 3:
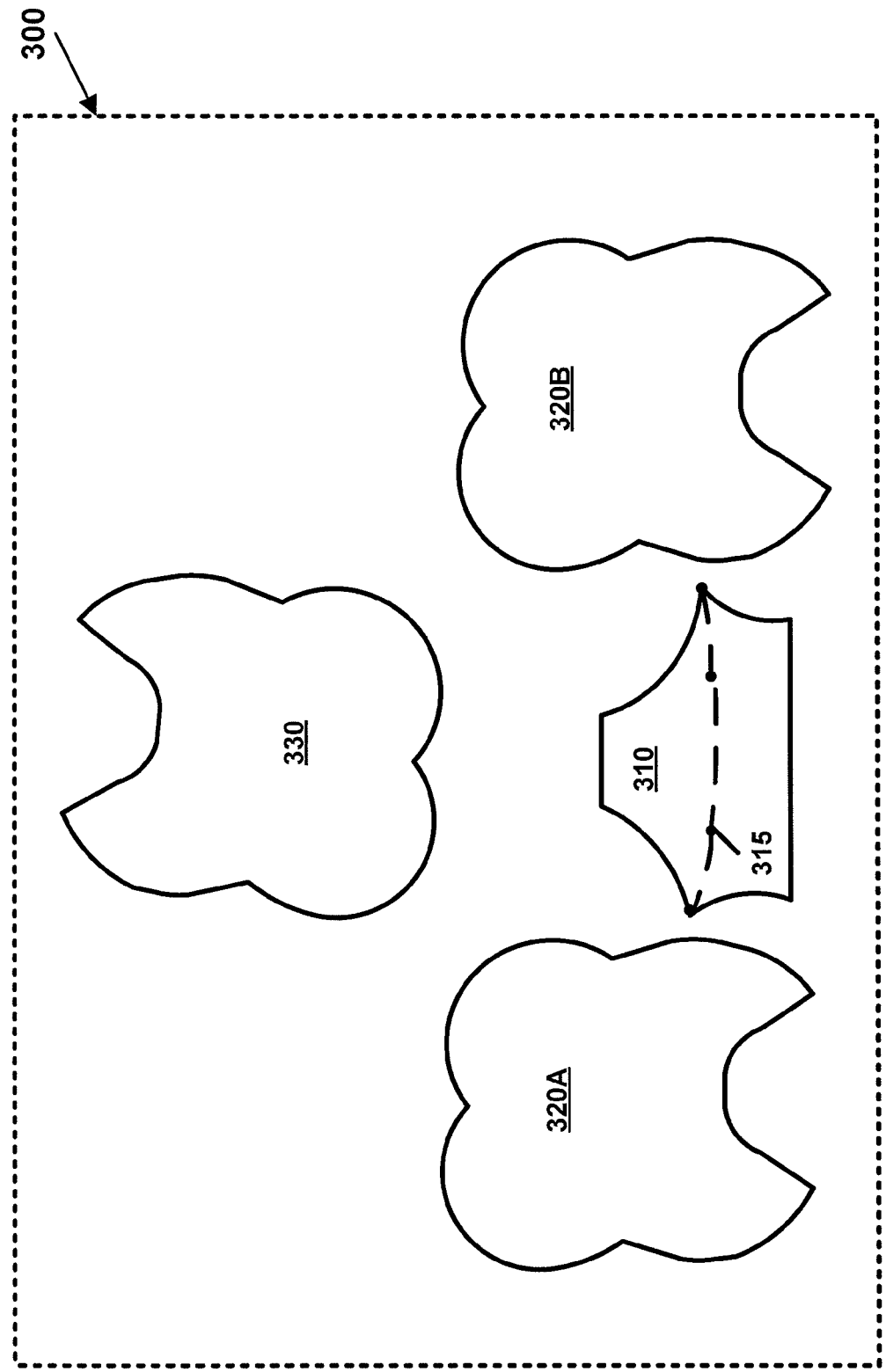
FIG. 3 illustrates an exemplary electronic model of a preparation site of a patient in accordance with the principles of the present disclosure.

The obtain operation 204 acquires or otherwise receives positional data indicating the location and/or dimensions of a preparation site at which the dental appliance is to be mounted. Typically, the obtain operation 204 acquires positional data representing a portion of the dentition of the patient. An example of such positional data includes an electronic model of the dentition of the patient. For example, FIG. 3 is a schematic block diagram illustrating an exemplary electronic model 300 representing a patient's dentition including an abutment (i.e., preparation site) 310. The circumference of the preparation site 310 is defined by a margin curve 315. In the example shown, the positional data also indicates positions of adjacent teeth 320 and antagonistic teeth 330 relative to the preparation site 310.

In an embodiment, the obtain operation 204 scans a physical model (e.g., a casting) or other representation of the preparation site of the patient to obtain positional data from which to generate the electronic model 300. For example, a polygonal mesh model of the preparation site can be generated using the processes described in commonly assigned U.S. Provisional Patent Application Ser. No. 60/351,270, filed Jan. 27, 2002, entitled "Method and Apparatus for Computer Generation of Electronic Model Images," now U.S. patent application Ser. No. 10/350,302, filed Jan. 22, 2003, now abandoned, the disclosure of which is hereby incorporated herein by reference. However, any suitable process for generating electronic models may be used.

Additionally, the electronic model 300 also may be created using computed tomography (CT) scans of dental impressions. For example, the electronic model 300 may be created using commercially available CT scanning processes, such as a process developed by Hytec Corp. of Los Alomos, N. Mex. Other methods of generating electronic models include optical system scanning, physical touch scanning, and any other such method using either direct scanning or scanning of physical models. For example, the obtain operation 204 can perform intra-oral scans of the patient's dentition or can retrieve the electronic models from a database or from another computing system. The acquired electronic model 300 of the preparation site is used in subsequent processing independent of the source of the electronic model 300.

A generate operation 206 creates an electronic model of the dental appliance based on the electronic model 300 of the preparation site. In general, the generate operation 206 produces an electronic model of a dental appliance that is dimensioned to enable the dental appliance to mount to the preparation site 310. One example of such a dental appliance model is a crown model shown at 400 in FIG. 4. The electronic model 400 generally includes an electronic mesh representation 410 of the dental appliance and a table 450 of attribute values. Further details describing the generation of the dental appliance electronic model 400 are discussed herein.

A fabricate operation 208 produces a physical dental appliance in accordance with the electronic model 400 of the dental appliance. In an embodiment, the fabricate operation 208 prints or mills the dental appliance from a biocompatible material. In another embodiment, the fabricate operation 208 prints or otherwise forms a pattern of the dental appliance and then produces the physical dental appliance from the pattern.

For example, the fabricate operation 208 can rapid prototype a wax pattern of the dental appliance and cast the dental appliance using lost-wax casting. One example of a rapid prototyping machine used to print wax models is the Patternmaster wax printer from Solidscape of Connecticut. However, any type of rapid prototyping process may be used without deviating from the spirit and scope of the disclosure. The creation process 200 completes and ends at a stop module 210.

Figure 5:
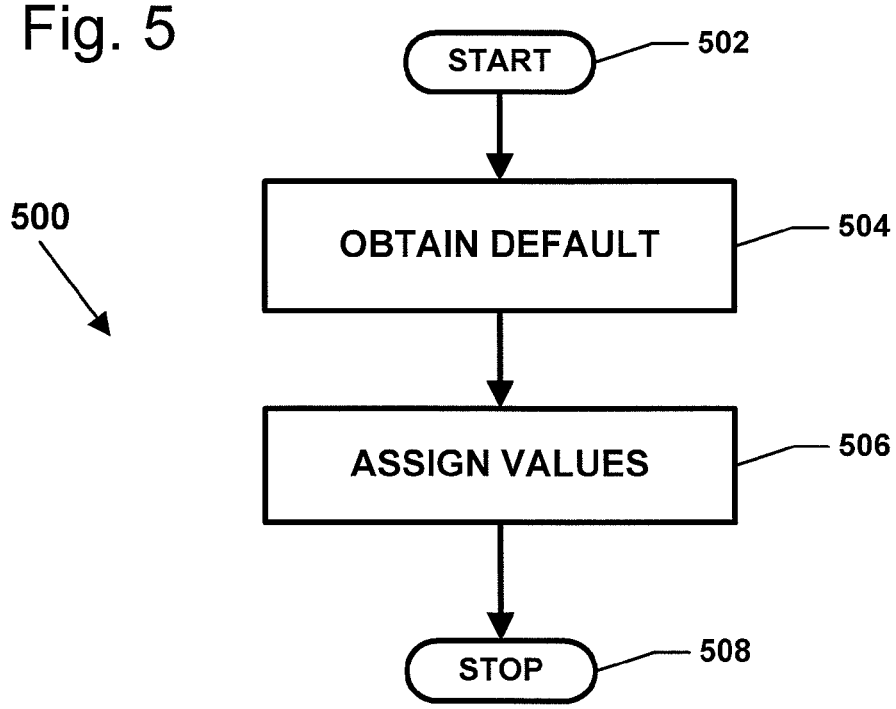
FIG. 5 is a flowchart illustrating an operational flow for a dental appliance generation process for producing an electronic model of a dental appliance in accordance with the principles of the present disclosure.

FIG. 5 shows one example dental appliance model generation process 500 that can be used to implement the generate operation 206 of FIG. 2. The appliance model generation process 500 initializes and begins at a start module 502 and proceeds to an obtain operation 504. The obtain operation 504 retrieves a template of the dental appliance from an electronic model library. For example, the obtain operation 504 can retrieve an electronic model, such as electronic model 400 including the mesh representation 410 of a restoration and the associated attribute table 450. In general, the attribute table 450 lists one or more attributes 452 of the dental appliance that define the mesh representation 410. For example, the attributes 452 may pertain to appliance dimensions, fabrication material, color, texture, or other properties of the dental appliance.

An assign operation 506 obtains values for the attributes 452 of the table. Typically, the table 450 includes a default value 454 associated with each attribute 452. In one embodiment, the assign operation 506 receives attribute values 454 input from a user to replace one or more of the default values. For example, a user may select attribute values 454 by deforming the electronic representation 410 to a desired shape. In another embodiment, the user may select from choices presented to the user. For example, a user may select ceramic as a fabrication material for the restoration. The generation process completes and ends at a stop module 508.

Figure 4:
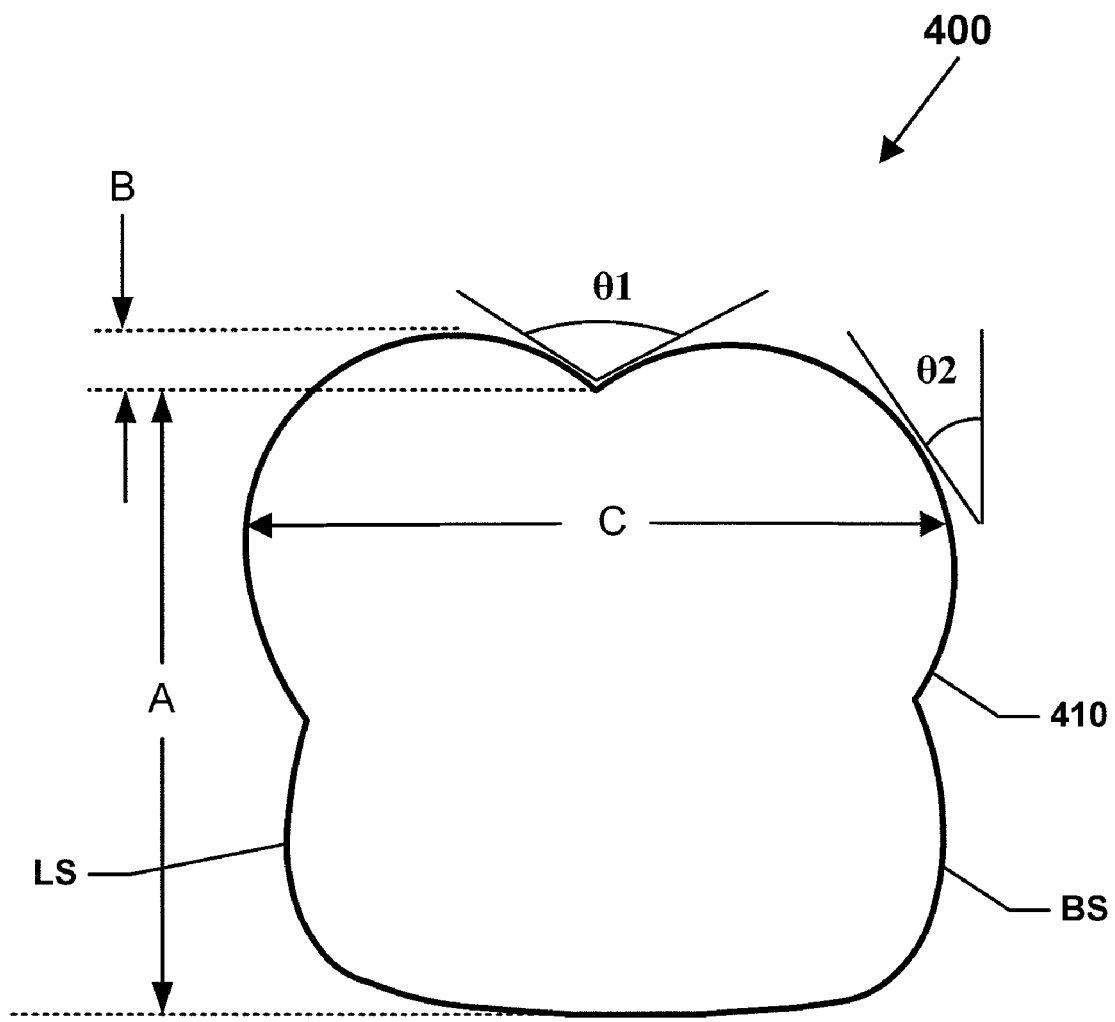
FIG. 4 illustrates an exemplary electronic model of a dental appliance to be installed on a preparation site in accordance with the principles of the present disclosure.

In the example shown in FIG. 4, the representation 410 of the restoration appliance has a marginal ridge height A, a cusp height B, a maximum facial-lingual thickness C, an inter-cusp angle $\theta 1$, and a buccal slope angle $\theta 2$. For the purposes of this disclosure, a marginal ridge height A is defined as the vertical distance between the gingival line and a fossa of a given tooth. In other embodiments, different attributes may be specified (e.g., height of contour, mamelon height, embrasures, etc.).

Figure 6:
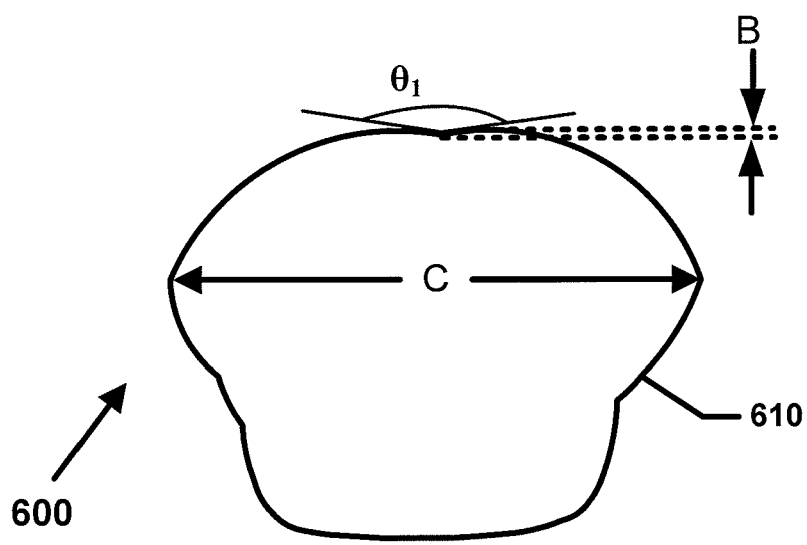
FIGS. 6 and 7 are examples illustrating how changing the values of attributes within an attribute table of an electronic model changes the properties of a corresponding representation in accordance with the principles of the present disclosure.
Figure 7:
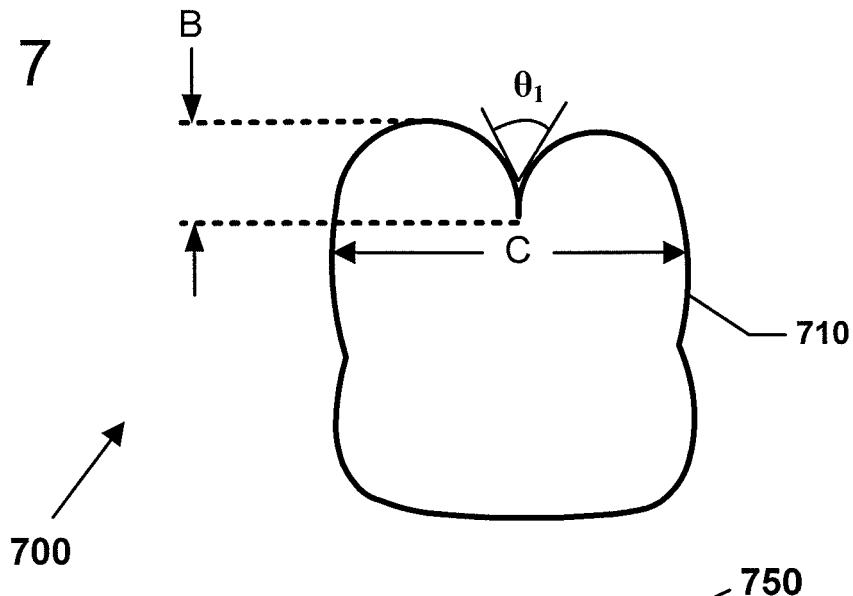

In general, the representation 410 of the dental appliance can be modified by entering new values 454 into the table 450. FIGS. 6 and 7 provide examples illustrating how changing the values 454 of the attributes 452 within the attribute table 450 of the electronic model 400 changes the properties of the corresponding representation 410. FIGS. 6 and 7 illustrate first and second electronic models 600, 700, respectively, resulting from different value assignments made to the attribute table 450 of the base model 400 (FIG. 4). Applicants note that FIGS. 6 and 7 present exaggerated depictions of the resulting electronic models for illustration purposes.

In FIG. 6, the first resulting electronic model 600 includes a dental appliance representation 610 having a different overall shape from the representation 410 of FIG. 4. The value 654 of the maximum facial-lingual thickness (i.e., buccal-facial or labial-facial) C listed in attribute table 650 of electronic model 600 has been increased from a base value of $C_{V1}$ to a value of $C_{V2}$. The value 652 of the cusp height B, however, was decreased from a base value of $B_{V1}$ to a value of $B_{V2}$. The decrease in cusp height B was complimented by a corresponding increase in the value of the inter-cusp angle $\theta 1$ from a value of $\theta 1_{V1}$ to a value of $\theta 1_{V2}$.

In contrast, the second resulting electronic model 700 includes a dental appliance representation 710 having a different shape as shown in FIG. 7. The value 752 of the maximum facial-lingual thickness C attribute 754 listed in attribute table 750 of the electronic model 700 has been decreased from a base value of $C_{V1}$ to a value of $C_{V3}$. The value 752 of the cusp height B, however, has been increased from a base value of $B_{V1}$ to a value of $B_{V3}$. The increase in the value 752 of the cusp height B was complimented by a corresponding decrease in the value of the inter-cusp angle $\theta 1$ from a value of $\theta 1_{V1}$ to a value of $\theta 1_{V3}$.

Figure 8:
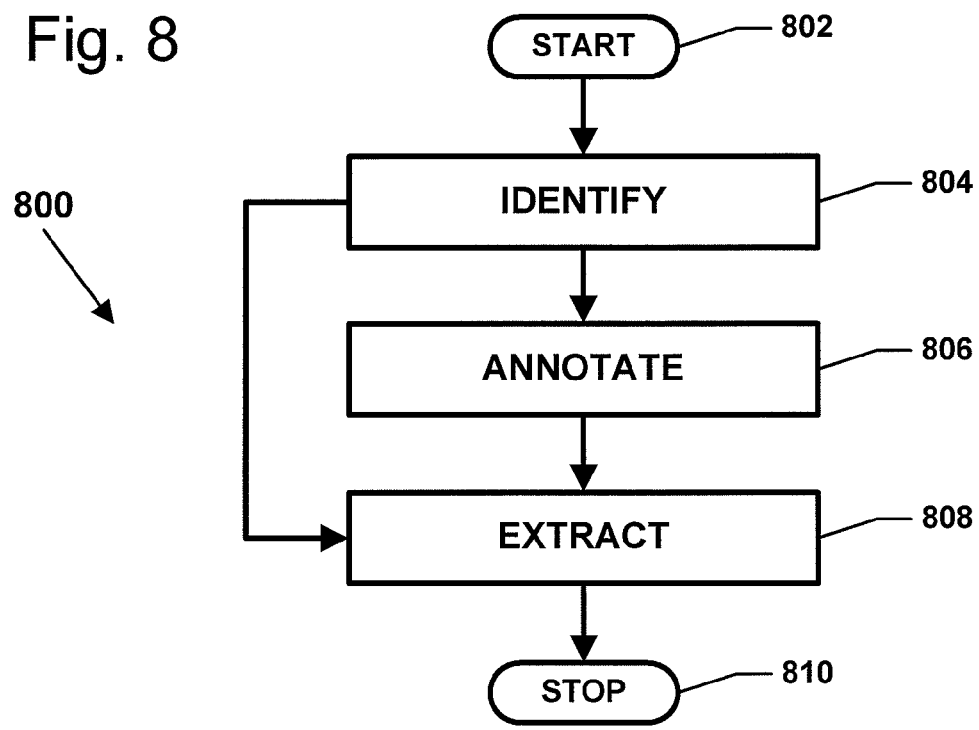
FIG. 8 is a flowchart illustrating an operational flow for a decision process for determining a value of each attribute in an attribute table of an electronic model of a dental appliance in accordance with the principles of the present disclosure.

Referring to FIGS. 8 and 9, desired attribute values for electronic models can be determined, at least in part, based on the anatomy of the patient (e.g., the surrounding teeth and gingiva). FIG. 8 is a flowchart illustrating an operational flow for a decision process 800 for determining a value of one or more attributes in the attribute table of an electronic model of a dental appliance. The decision process 800 initializes and begins at a start module 802 and proceeds to an identify operation 804.

Figure 33:
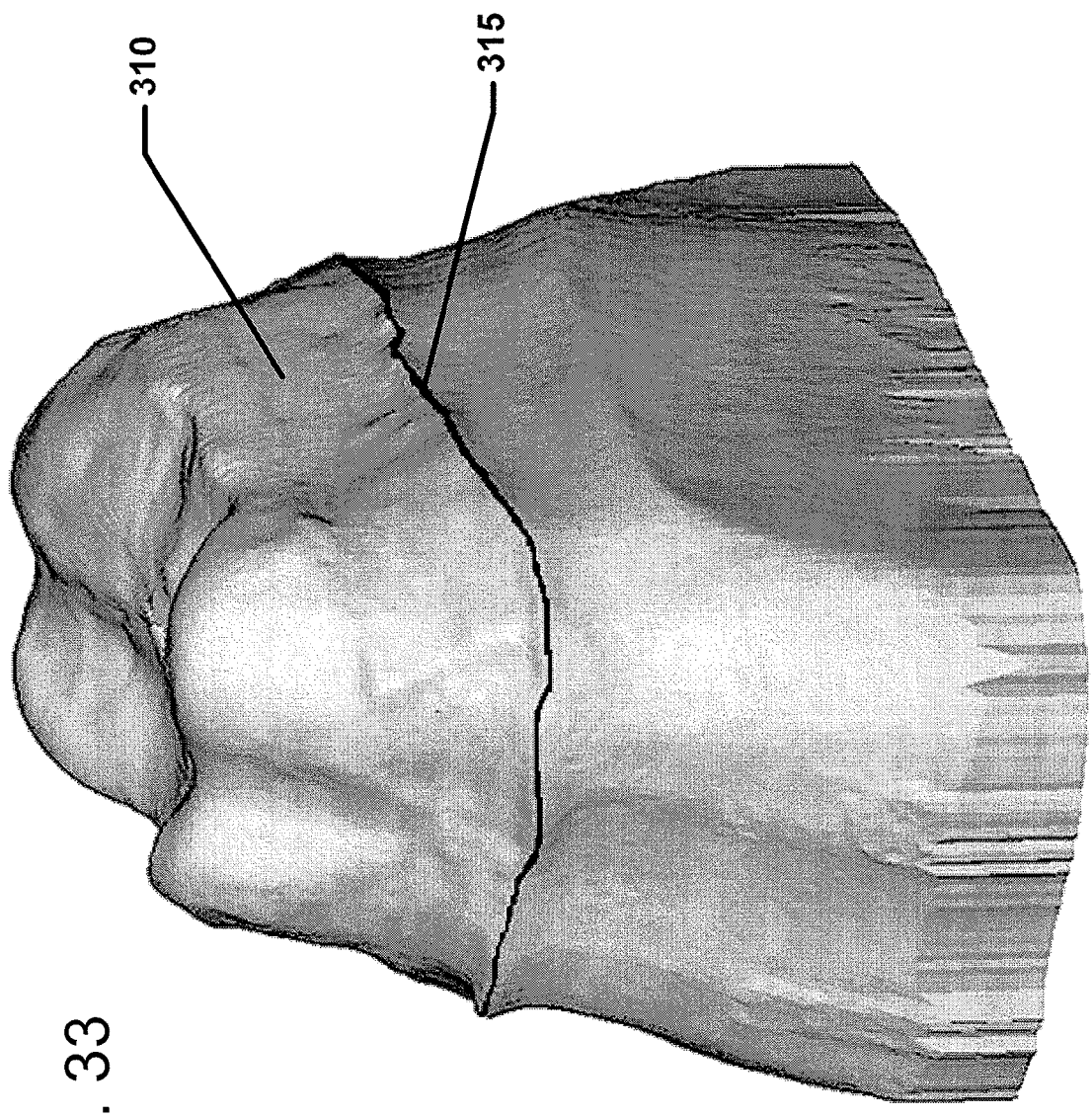
FIG. 33 is a perspective view of an electronic model of a preparation site including an annotated margin curve in accordance with the principles of the present disclosure.

The identify operation 804 determines the locations of landmarks (i.e., points of interest) within the positional data. For example, the identify operation 804 can determine the dimensions, such as the margin curve 315, of the preparation site 310 onto which the dental appliance is to be installed (e.g., see FIG. 33). Typically, the identify operation 804 also determines locations of adjacent teeth 320, antagonistic teeth 330, and/or edentulous tissue.

In some embodiments, the identify operation 804 analyzes the positional data representing the preparation site, such as electronic model 300 of FIG. 3, to identify landmarks. In other embodiments, the identify operation 804 receives and processes input from a user identifying the landmark feature. For example, the identify operation 804 can receive and interpret user input provided through an input tool, such as a mouse, light pen, or finger (on a touchpad).

Figure 34:
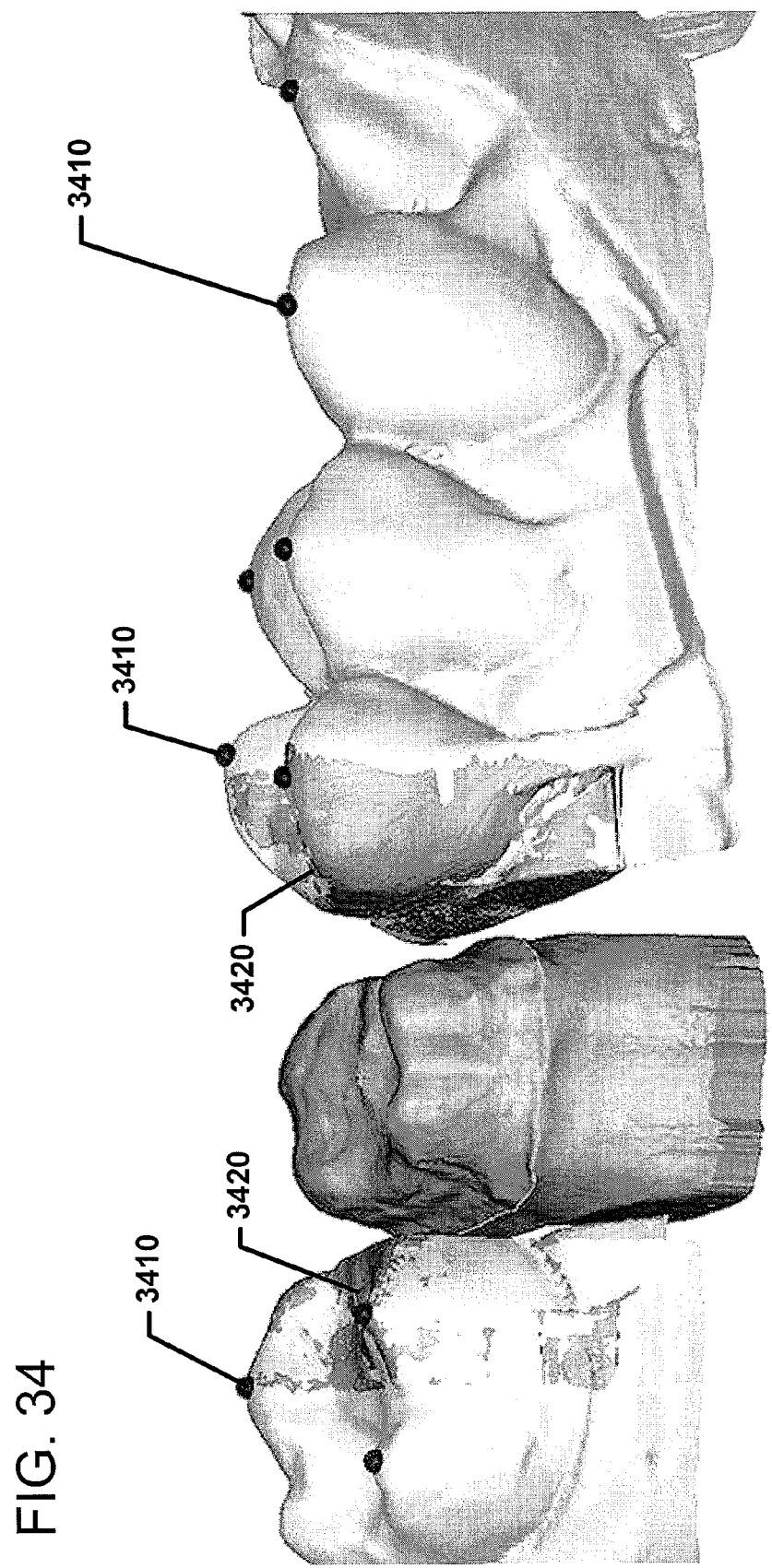
FIG. 34 is a perspective view of another electronic model of a preparation site and surrounding anatomy including annotated landmarks in accordance with the principles of the present disclosure.

An optional annotate operation 806 can superimpose markers over the identified features of the electronic model 300 of the dentition. The markers visually highlight the landmark features of the model 300 to the user (e.g., see cusp markers 3410 and fossa markers 3420 of FIG. 34). Some non-limiting examples of markers include arrows, circles, dots, shading, and other indicators displayed with the electronic model 300. In the example shown in FIG. 34, landmarks are annotated with dots.

Figure 35:
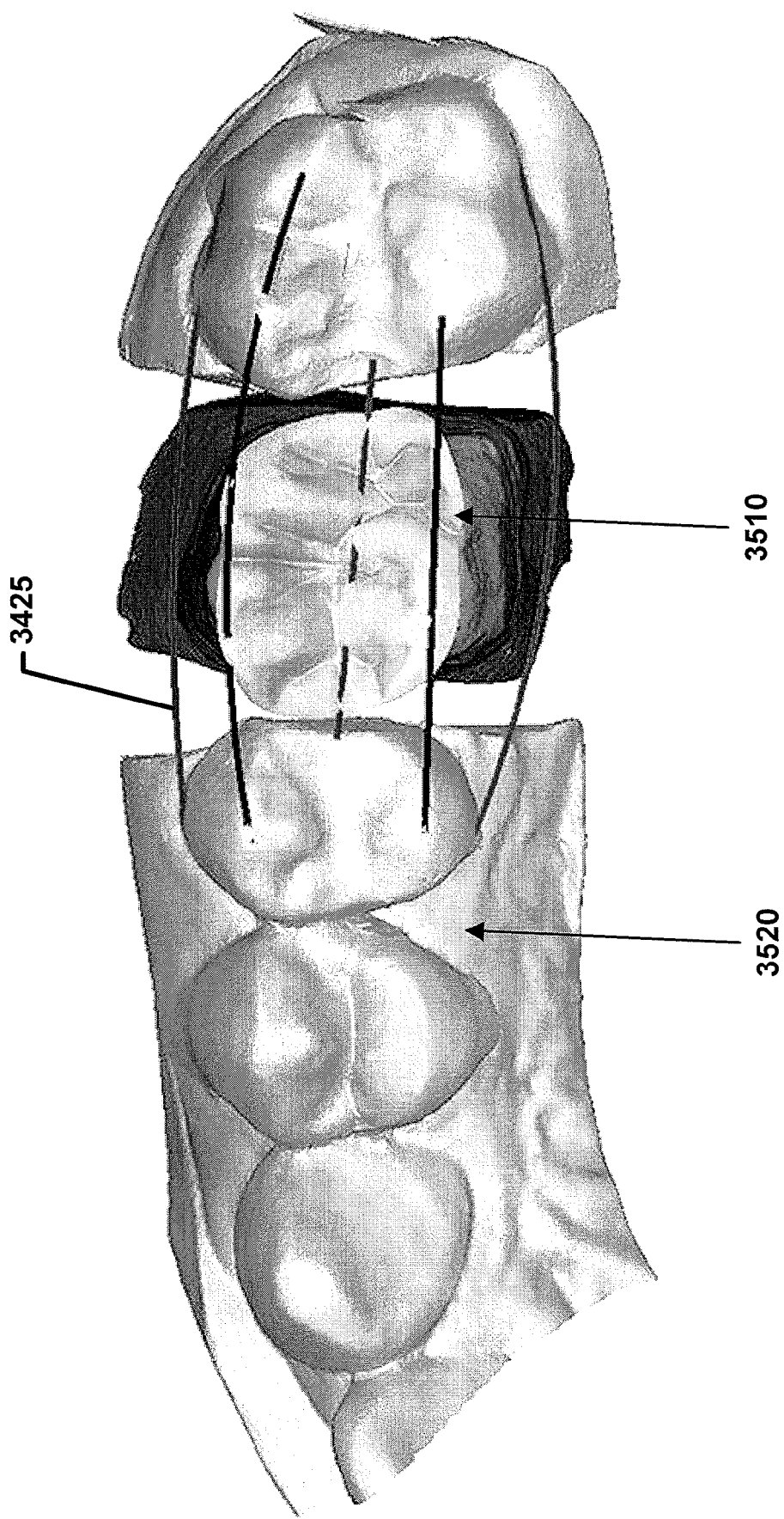
FIG. 35 is a plan view of another electronic model of a preparation site and surrounding anatomy including diagramming lines coupling identified landmarks in accordance with the principles of the present disclosure.
Figure 36:
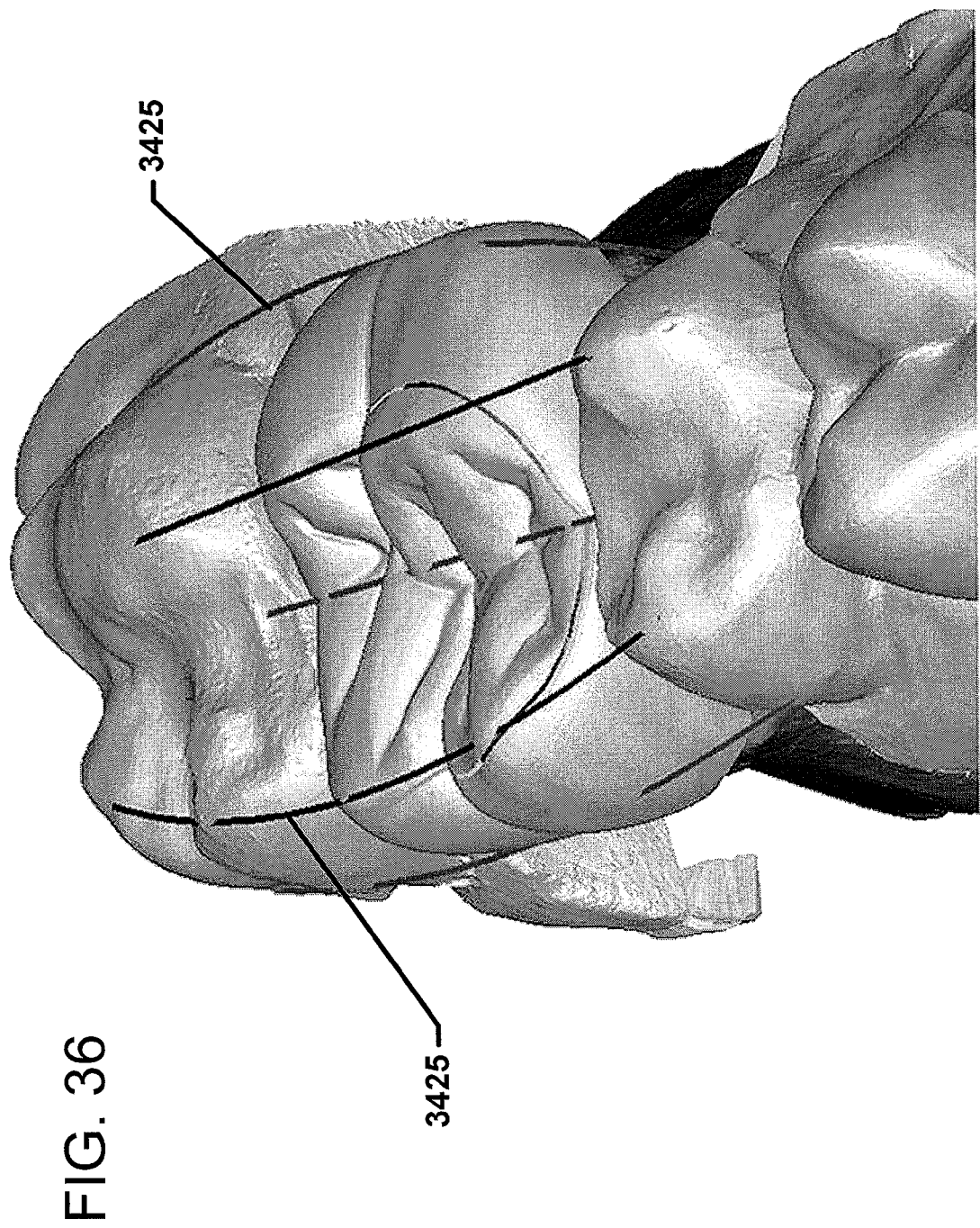
FIG. 36 is a perspective view of another electronic model of a preparation site and surrounding anatomy including diagramming lines coupling identified landmarks in accordance with the principles of the present disclosure.

Diagramming lines are another example of markers. For the purposes of this disclosure, a diagramming line is a line (e.g., linear or curved) extending over portions of an electronic model. In one embodiment, a diagramming line connects common anatomical features of adjacent teeth. Such a diagramming line can serve as a helpful visual reference when determining trends in patient anatomy or what dental appliance features will blend in with the patient's anatomy. For example, a diagramming line DL1 can be drawn along the lingual cusps 962 of neighboring teeth 920 as shown in FIG. 9 to aid in visualizing an appropriate cusp height for a dental appliance 900. Other examples of diagramming lines 3425 are shown in FIGS. 35 and 36.

An extract operation 808 determines attribute values of an electronic model of a dental appliance, such as attributes values 454 of electronic model 400, based, at least in part, on the identified anatomical landmarks. In general, the extract operation 808 can determine the location and dimensions of a landmark feature using the positional data representing the dentition. In one embodiment, the extract operation 808 can determine the location and dimensions of the landmarks based on user annotations. The extract operation 808 also can measure distances (e.g., within a coordinate system) between known points within the positional data or along diagramming lines.

For example, the extract operation 808 can determine a vertical height and/or a height of contour of one or more teeth, such as teeth 320, adjacent to the preparation site, such as preparation site 310 (FIG. 3). As another example, the extract operation 808 can determine the size, shape, and/or location of the cusps of a restoration appliance based on cusps and fossa of adjacent and/or antagonistic teeth (see FIG. 3). As yet another example, the extract operation 808 can determine the shape and location of the margin curve 315 of the preparation site 310 to enable an electronic model of a dental appliance (e.g., a restoration) to be designed to mate with the preparation site 310 at the margin curve 315 (FIG. 3).

Further details describing the measurement of landmarks using electronic modeling of positional data taken of the patient's dentition can be found in application Ser. No. 11/231,064, filed Sep. 19, 2005, entitled "System and Method for Determining Condyle Displacement Utilizing Electronic Models of Dental Impressions Having a Common Coordinate System," (issued as U.S. Pat. No. 7,824,346) the disclosure of which is hereby incorporated herein by reference. In still other embodiments, the extract operation 808 can determine a location of the landmark with respect to another landmark (e.g., antagonistic occlusal surfaces), a color of a landmark, or another property associated with the landmark.

The decision process 800 completes and ends at a stop module 810. In some embodiments, parts of the decision process 800 may be performed manually. For example, a user may display an electronic model of a patient's dentition, such as electronic model 300 of FIG. 3, on a computing device and add markers (e.g., circles, arrows, and other annotations) or trace diagramming lines using an input tool, such as input device 150 of FIG. 1. In other embodiments, however, the decision process 800 may be performed automatically by a computer.

Figure 10:
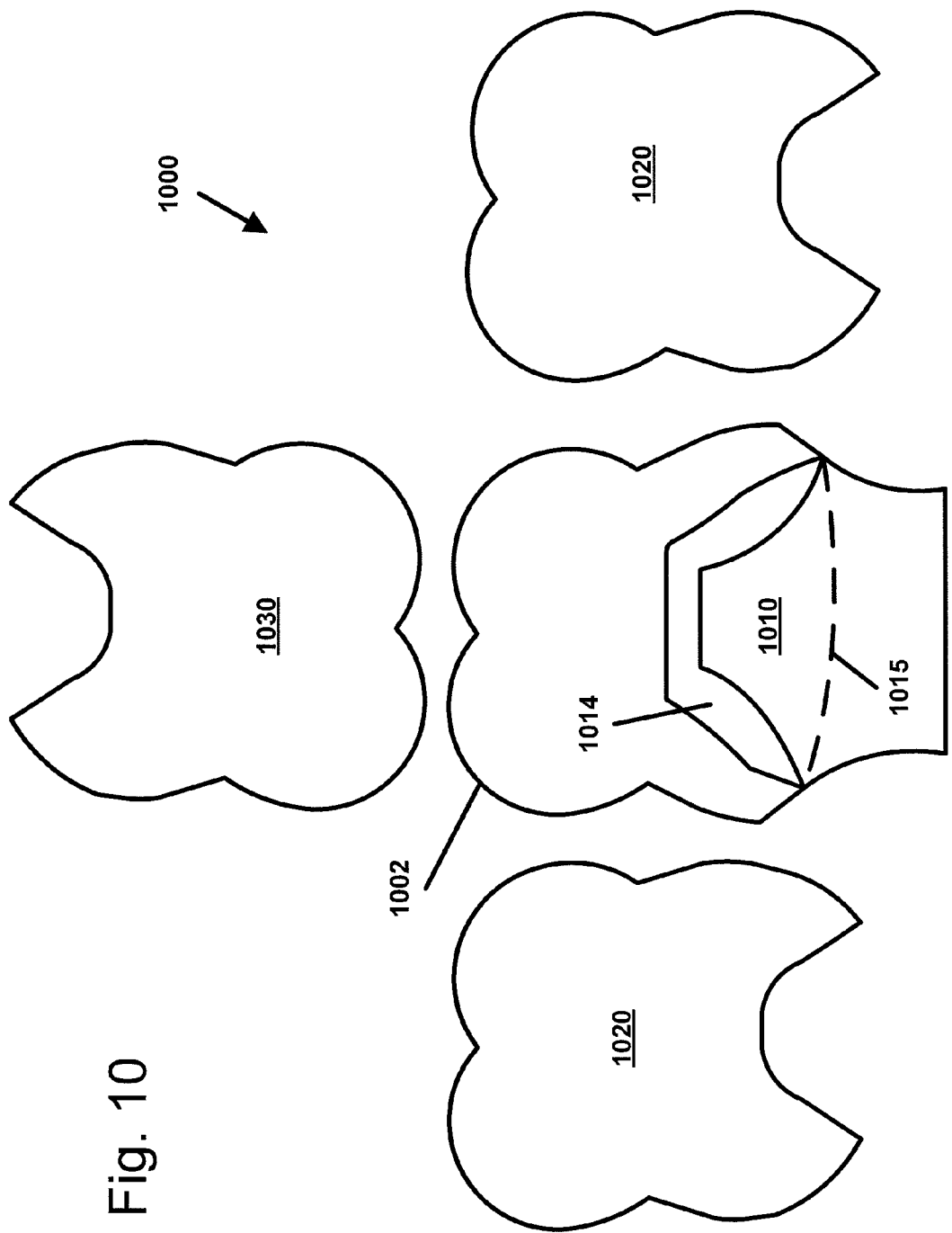
FIG. 10 illustrates an electronic model of a dental appliance superimposed over an electronic model of a preparation site in accordance with the principles of the present disclosure.

Referring to FIG. 10, in some embodiments, desired attribute values for electronic models can be determined interactively by superimposing the electronic model of the dental appliance over an electronic model of a preparation site and receiving user selections of anatomical features. For example, in FIG. 10, the display 1000 shows an electronic model of a restoration 1002 positioned over an electronic model of a preparation site 1010. Such a configuration enables the user to visually assess the values assigned to the attributes of the electronic model(s) and the effects of modifying the values.

For example, the electronic model 1002 of the dental appliance can be interactively modified by the user to create sufficient space 1014 to accommodate adhesive for securing the dental appliance 1002 to the preparation site 1010. Additional details describing the design of dental appliances can be found, e.g., in application Ser. No. 10/429,288, filed May 2, 2003, entitled "Method and Apparatus for Constructing Crowns, Bridges and Implants for Dental Use," (issued as U.S. Pat. No. 7,228,191) the disclosure of which is hereby incorporated by reference.

Figure 12:
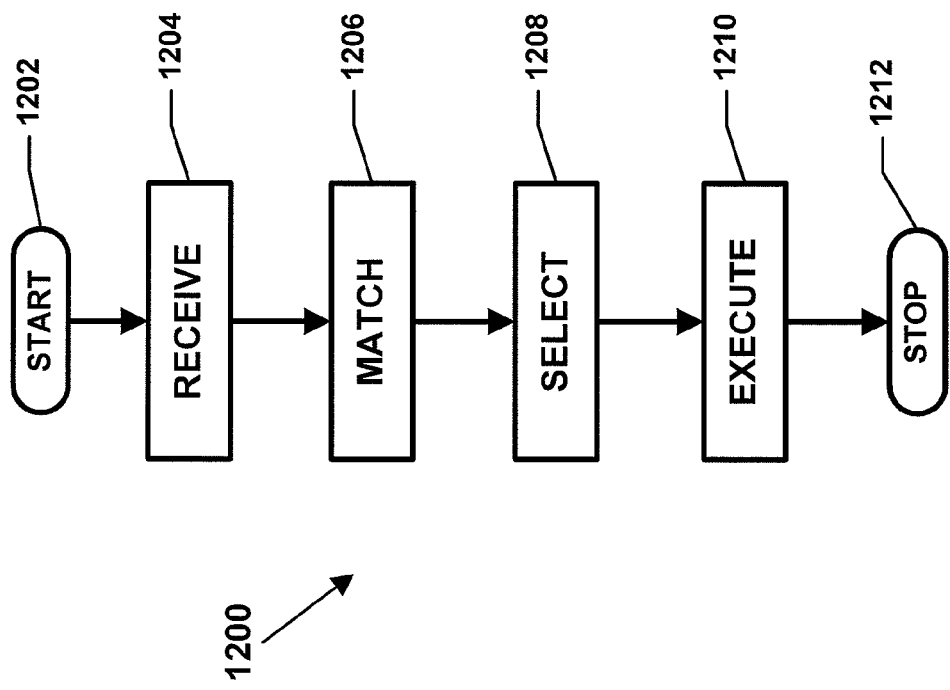
FIG. 12 is a flowchart illustrating an operational flow for designing a dental appliance using the inference engine of FIG. 11 in accordance with the principles of the present disclosure.

In other embodiments, desired attribute values for electronic models can be determined automatically by a computer device. For example, in FIGS. 11 and 12, at least part of the model generation process (e.g., the decision process 800 of FIG. 8) may be performed using an inference engine 1100 and a set 1120 of rules 1125 (or processes) for shaping and dimensioning an electronic model of a dental appliance to fit within a known space. In the example shown, the rule set 1120 includes a first rule (Rule 1) 1125A, a second rule (Rule 2) 1125B, and an Nth rule (Rule N) 1125N.

In general, the inference engine 1100 analyzes the rules 1125 to determine relevancy to a particular data set (e.g., the positional data pertaining to the preparation site) and chooses relevant rules to apply to the data set. Implementation of the selected rules 1125 can change the information of the received data set. For example, execution of the rules 1125 can change the values of attributes with which the dental appliance electronic model is associated. Implementation of the rules 1125 also can trigger additional processes, such as user interaction through a display and input interface.

Figure 11:
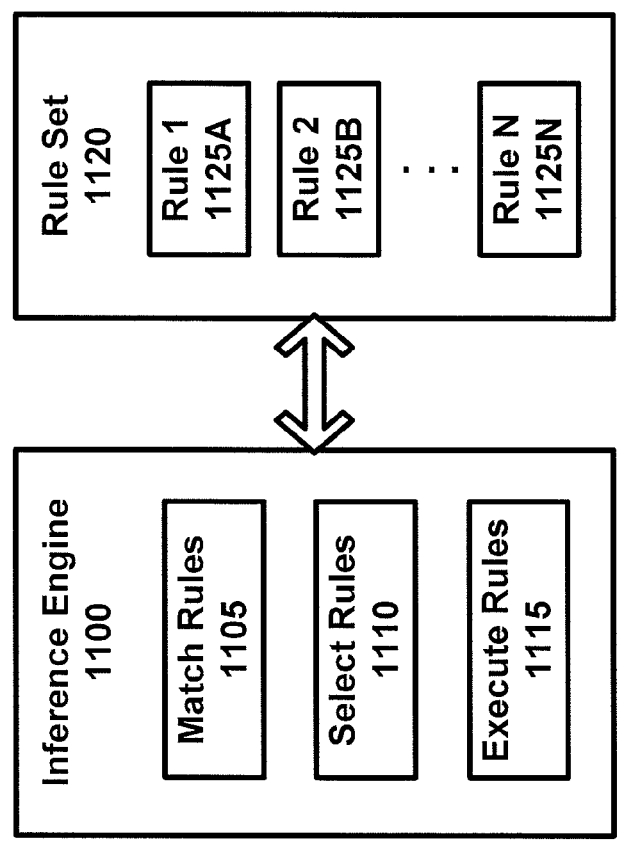
FIG. 11 is a block diagram of an inference engine configured to design a dental appliance in accordance with the principles of the present disclosure.

For example, FIG. 11 illustrates a set of processing modules within an inference engine 1100 utilized to implement the decision process 800 of FIG. 8 for generating electronic models of dental appliances. The inference engine 1100 shown includes a match rules module 1105, a select rules module 1110, and an execute rules module 1115. These modules 1105, 1110, 1115 implement the electronic modeling processes described herein. For example, in one embodiment, these modules 1105, 1110, 1115 implement an analysis process 1200 shown in FIG. 12 to generate an electronic model of a dental appliance.

The exemplary analysis process 1200 initializes and begins at a start module 1202 and proceeds to a receive operation 1204. The receive operation 1204 obtains a data set of information to which the rules 1125 are to be applied by the inference engine 1100. In one embodiment, the data set of information includes the positional data representing the preparation site 310 (FIG. 3) of the patient. In different embodiments, however, the data set of information can include positional data representing surrounding anatomy of the patient, positional data representing the dental appliance, subsets and combinations thereof, and any other desired information.

A match operation 1206 determines which rules 1125 of the rule set 1120 are applicable to the information of the received data set. For example, when the information of the received data set includes positional data of the preparation site, then the match operation 1206 can determine a rule 1125 for determining the dimensions of a gingival surface of the dental appliance. In one embodiment, a first rule 1125A may state the dimensions of the gingival surface of the dental appliance should correspond to a margin curve of the preparation site. In such an embodiment, a second rule 1125B may dictate how the margin curve of the preparation site is identified. In another embodiment, the information of the data set acquired at receive operation 1204 may include information pertaining to the surrounding anatomy of the patient. In such embodiments, the match operation 1206 can determine a rule 1125N for determining cusp height of the dental appliance based on the cusp height of adjacent teeth.

A select operation 1208 determines which matched rules 1125 to execute. For example, if the inference engine 1100 is adapted to insert a height of contour value for the electronic model based on the height of contour of a tooth adjacent to the preparation site, then the select operation 1208 may select rules for determining locations for adjacent teeth. In one embodiment, the select operation 1208 is configured to select rules 1125 based on one of the processes described in application Ser. No. 10/350,304, filed Jan. 22, 2003, entitled "Method and Apparatus for Automatically Determining the Location of Individual Teeth Within Electronic Model Images," (issued as U.S. Pat. No. 7,245,750) the disclosure of which is hereby incorporated by reference.

In general, the select operation 1208 generates a strategy for applying the selected rules 1125 to the received data set. The strategy includes a sequence in which the rules are to be executed. The select operation 1208 can sequence the rules according to dependency, relevancy, or as otherwise specified by one or more of the rules. An execute operation 1210 performs the selected rules 1125 according to the generated strategy. The analysis process completes and ends at a stop module 1210.

In general, the rules 1125 of the rule set 1120 may be obtained from one or more sources, e.g., dentists, dental lab technicians, orthodontists, and other such experts and/or professionals. In one embodiment, the rules 1125 may be inconsistent with one another because the rules 1125 can be obtained from different sources. Accordingly, the select operation 1208 optionally can perform conflict resolution by eliminating and/or sequencing the matched rules 1125 according to dependency, consistency, and/or relevancy.

In some embodiments, the rules 1125 indicate design criteria based on statistical data, such as average shapes, sizes, colors, and textures associated with one or more of the patient's age, sex, ethnicity, or other attributes. For example, in one embodiment, one or more rules 1125 may indicate an average crown shape and/or average dimensions for a forty-year-old Caucasian male. In another embodiment, the rule 1125 may indicate an average tooth color for a seventeen-year-old Asian female. In another embodiment, however, the rules 125 indicate how to determine design criteria for an electronic model based on surrounding anatomy of the patient.

Figure 13:
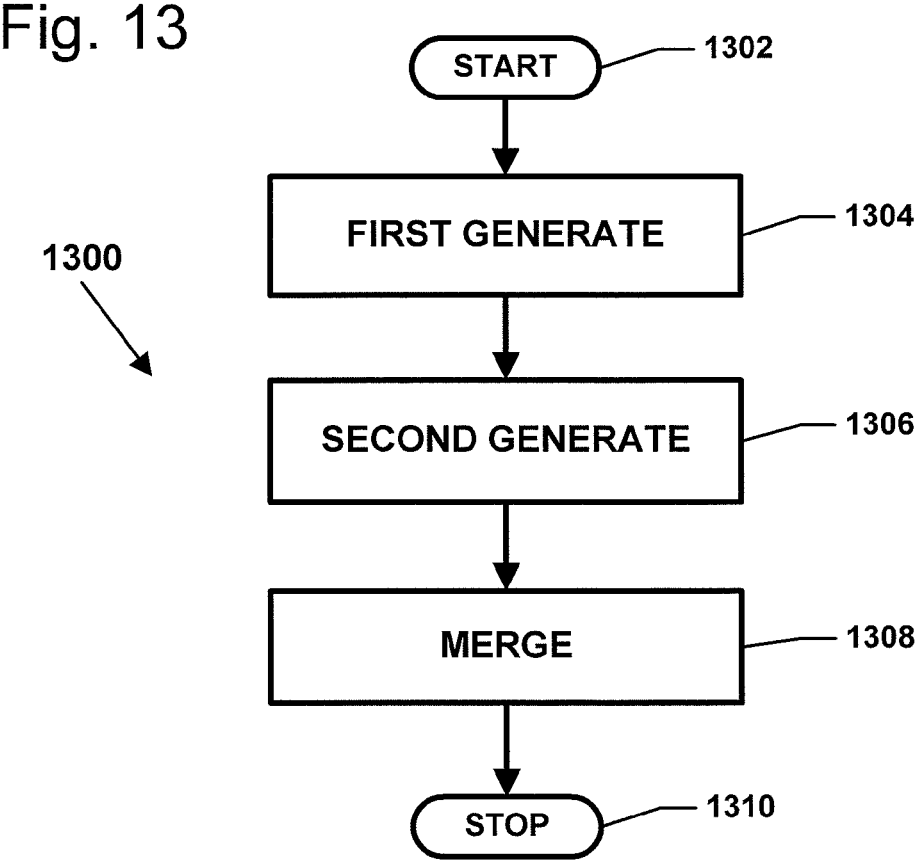
FIG. 13 is a flowchart illustrating an operational flow for a creation process for producing an electronic model of a dental appliance from at least two electronic models in accordance with the principles of the present disclosure.

Referring to FIGS. 13-16, the electronic models of dental appliances can be formed from multiple components. FIG. 13 is a flowchart illustrating an operational flow for an exemplary creation process 1300 for producing an electronic model of a dental appliance from at least two electronic models. The creation process 1300 initializes and begins at a start module 1302 and proceeds to a first generate operation 1304.

Figure 14:
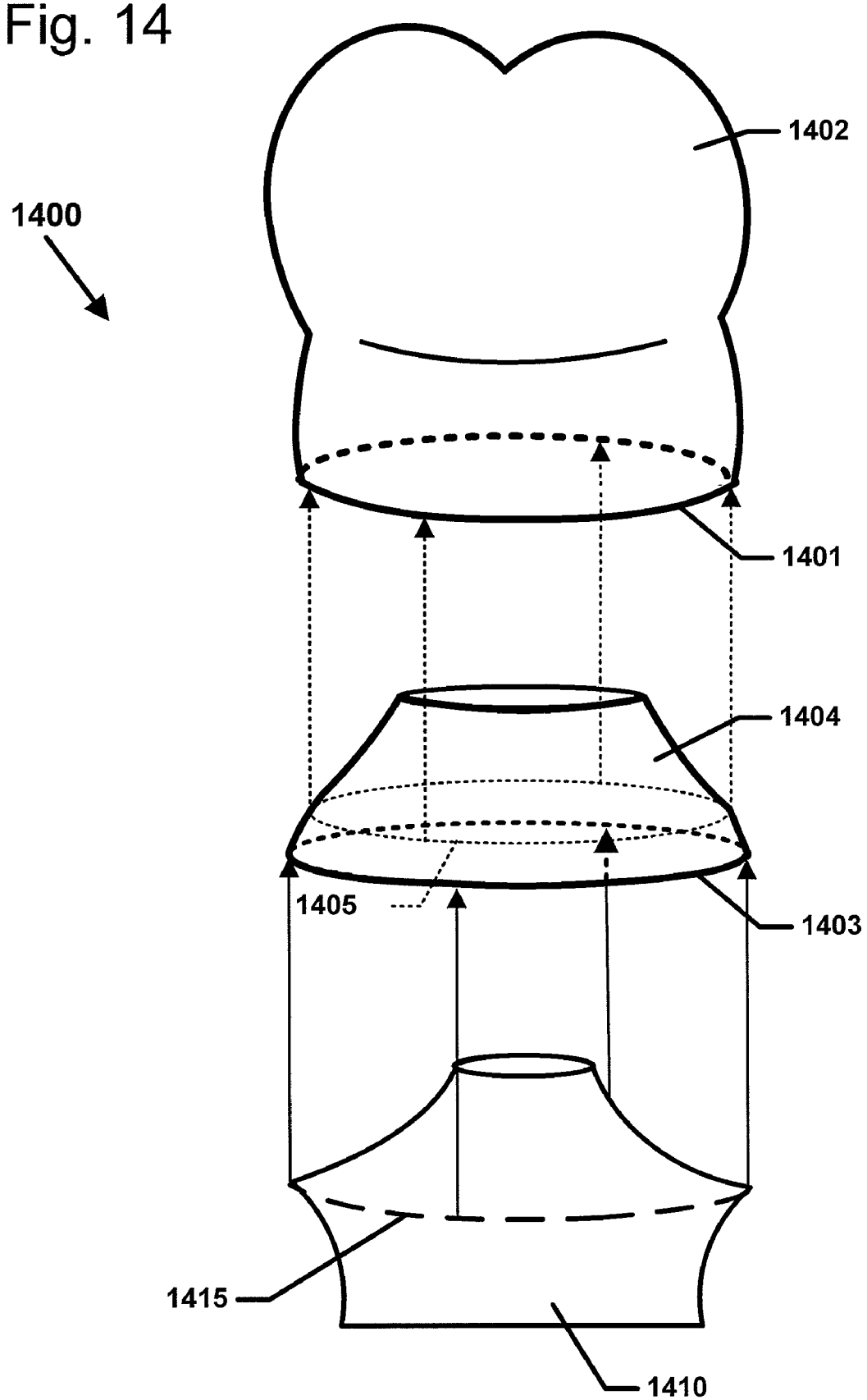
FIG. 14 illustrates an electronic model formed from a first surface mesh and a second surface mesh in accordance with the principles of the present disclosure.

The first generate operation 1304 generates an electronic model of a first component, such as an occlusal component 1402 of FIG. 14. For example, the first electronic model 1402 of FIG. 14 represents an occlusal component of a restoration configured to interact with the surface of an antagonistic tooth. A second generate operation 1306 generates an electronic model of a second component of the dental appliance, such as the interface component 1404 of FIG. 14. In the example shown, the second electronic model 1404 represents an interface component configured to interact with the preparation site 310 of FIG. 3. In other embodiments, the second electronic model 1404 can represents a coping substructure, an artificial abutment, a pontic, or any other component of a dental appliance.

A merge operation 1308 combines the electronic model of the first component 1402 with the electronic model of the second component 1404 to create a combined electronic model 1400 of the dental appliance. In the example shown, the merge operation 1308 defines an interaction site 1405 on the second electronic model 1404 at which to couple the gingival edge 1401 of the first electronic model 1402. The combined electronic model 1400 in FIG. 14 represents a restoration with the first electronic model 1402 representing an occlusal surface and the second electronic model representing a gingival surface of the restoration. The creation process 1300 completes and ends at a stop module 1310.

The electronic models 1402, 1404 can be produced using the generation process 500 discussed above with reference to FIG. 5. For example, the dimensions for the gingival surface 1401, 1403 of at least one of the electronic models 1402, 1404, respectively, can be determined based on measurements of the margin curve 1415 of the abutment 1410. Alternatively, one of the electronic models 1402, 1404 can be produced by an alternative generation process or can be obtained from a memory of a computing device.

Figure 15:
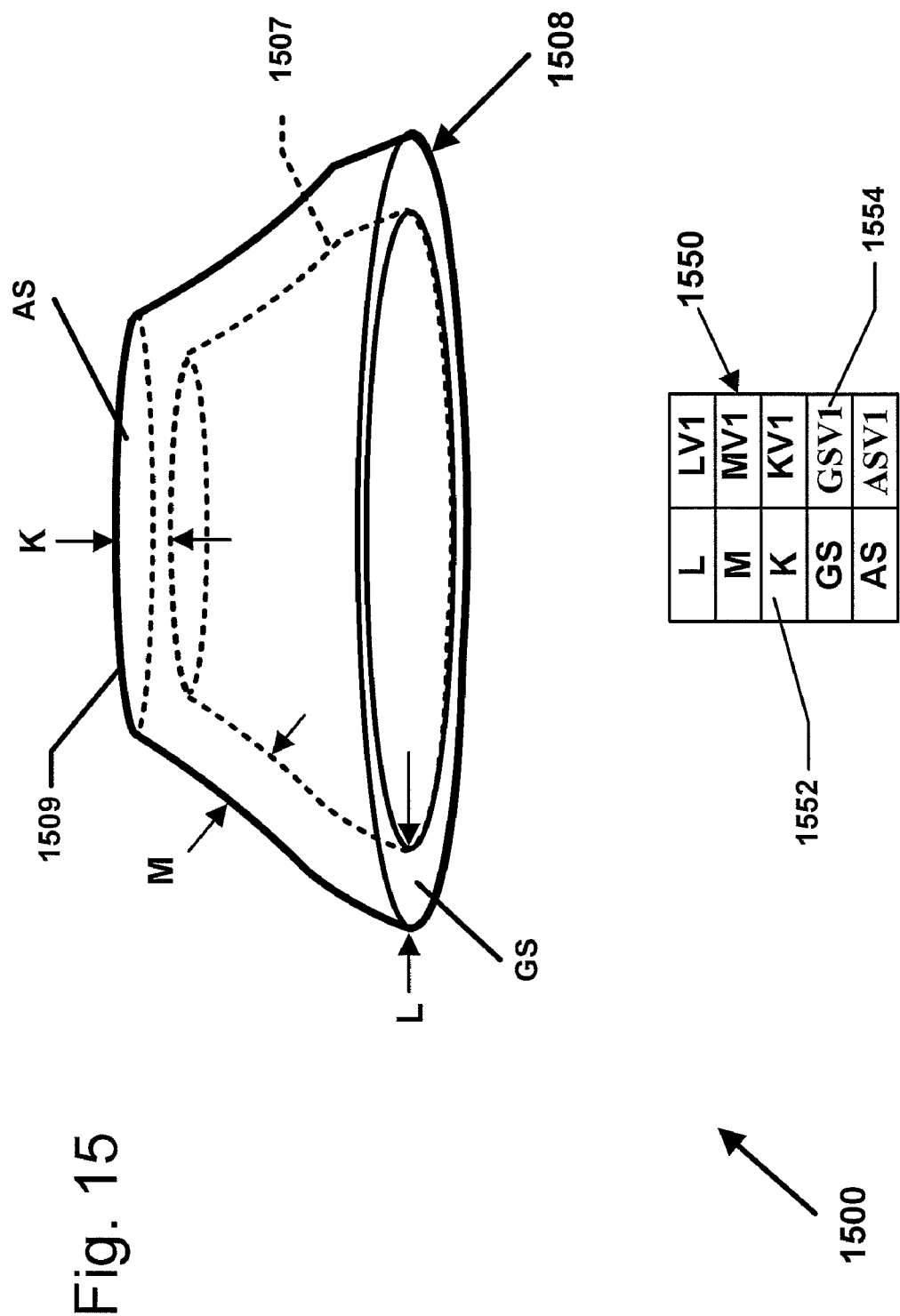
FIG. 15 is an exemplary electronic model of a coping substructure including a coping representation and an attribute table in accordance with the principles of the present disclosure.
Figure 16:
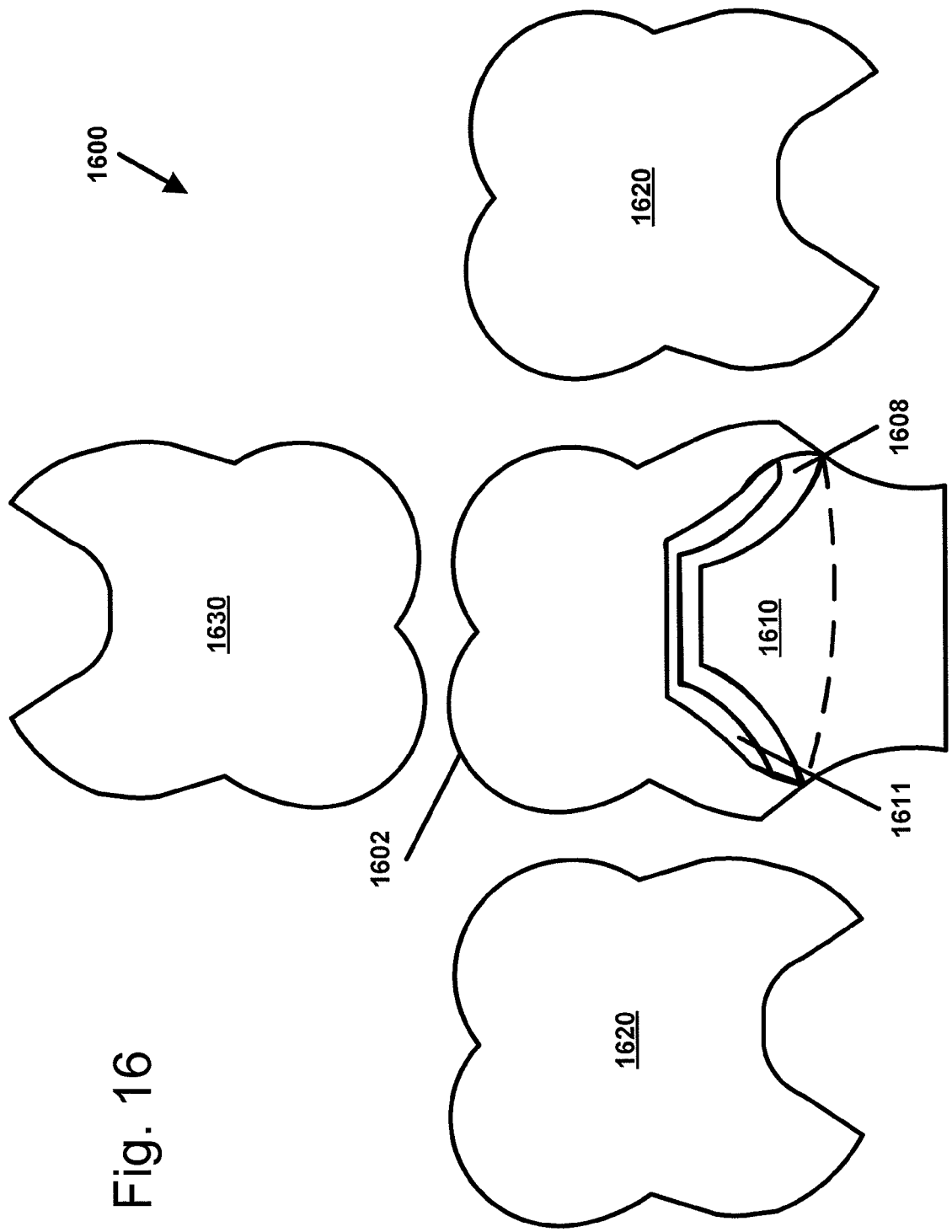
FIG. 16 illustrates an electronic model of a restoration superimposed over an electronic model of a coping substructure, which is superimposed over an electronic model of a preparation site in accordance with the principles of the present disclosure.

Referring to FIGS. 15-16, multiple components of the dental appliance can be designed together, but fabricated separately. For example, if the dental appliance is a restoration, a coping substructure 1508 can be designed before, after, or concurrently with a crown structure 1502 to fit together on a preparation site 1510 of a patient (see FIG. 16). Typically, the coping substructure 1508 is fabricated from metal, whereas the crown substructure 1502 may be fabricated from metal, ceramic, or other dental materials.

FIG. 15 illustrates an exemplary electronic model 1500 of a coping substructure 1540. The electronic model 1500 includes a representation 1508 of a coping substructure and an attribute table 1550. The representation 1508 has a gingival surface 1507, at which the coping substructure couples to the preparation site, and an abutment surface 1509, at which a crown is coupled. The representation 1508 also has a wall thickness L at the gingival surface 1507, a wall thickness K at the occlusal surface, and a wall thickness M along sidewalls of the coping substructure 1508. The shape and size of the coping substructure electronic model 1500 shown can be modified by modifying the values 1552 of the attributes 1554 of the attribute table 1550.

FIG. 16 illustrates an electronic model of a crown restoration 1602 superimposed over an electronic model of a coping substructure 1608, which is superimposed over an electronic model of a preparation site 1610. In the example shown in FIG. 16, the coping substructure 1608 has a generally consistent thickness that does not correspond to the crown restoration 1602 that the coping substructure 1608 supports. A gap 1611 is left between the coping substructure 1608 and the crown restoration 1602 for adhesive to be applied between the fabricated pieces.

In other embodiments, the coping substructure can have other features (e.g., collar dimensions) modifiable by the attribute table. Additional details pertaining to the design of coping substructures, can be found, e.g., in application Ser. No. 11/186,391, filed Jul. 20, 2005, entitled "Multi-Component Dental Appliances and a Method For Constructing the Same," (issued as U.S. Pat. No. 7,819,662) the disclosure of which is hereby incorporated by reference.

Multi-Piece Dental Restorations

Referring to FIGS. 17-24, a dental restoration may include one or more components (e.g., a coping substructure and a crown superstructure). In some embodiments, portions of a dental restoration (e.g., the coping substructure) may be designed based on other portions of the dental restoration (e.g., the crown superstructure). In other embodiments, an overall prosthesis (e.g., the dental restoration) is designed first, and the components are defined based on the overall prosthesis.

Figure 17:
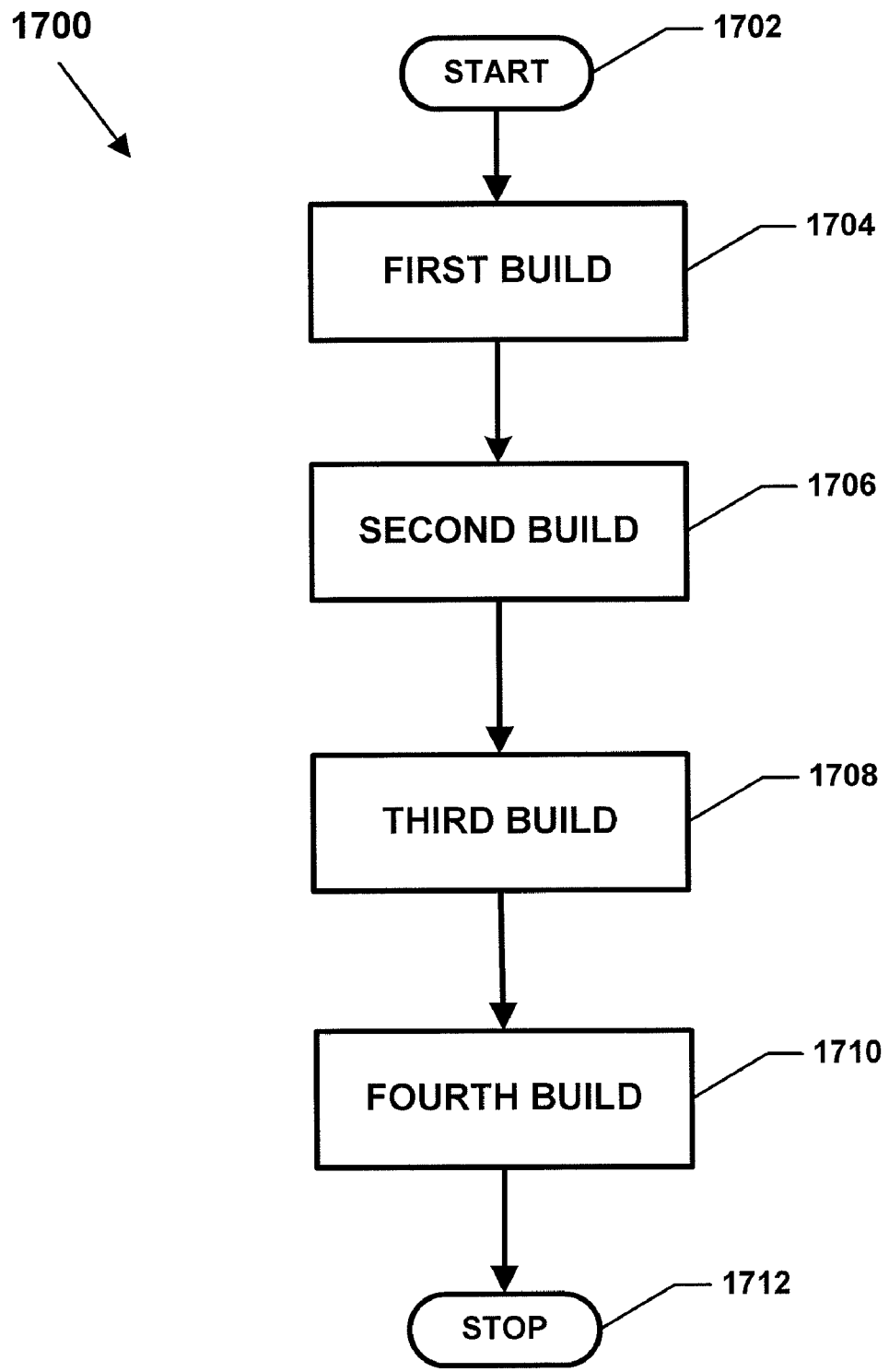
FIG. 17 is a flowchart illustrating an operational flow for an exemplary design process by which a first electronic model may be generated based on a second electronic model in accordance with the principles of the present disclosure.

For example, FIG. 17 is a flowchart illustrating an operational flow for an exemplary design process 1700 by which a dental restoration may be designed. FIGS. 18-24 are schematic diagrams illustrating an electronic model of a dental restoration 1800 generated using the design process 1700 of FIG. 17 at different stages of the design process 1700. The design process 1700 initializes and begins at a start module 1702 and proceeds to a first build operation 1704.

In general, the first build operation 1704 generates or acquires a first electronic model that is shaped and dimensioned in accordance with outer boundaries of the dental restoration. For example, in one embodiment, the first build operation 1704 generates or otherwise obtains an electronic mesh representing an occlusal surface and side walls of a crown superstructure of the dental restoration. In another embodiment, the first build operation 1704 generates or otherwise obtains a closed electronic model of the dental restoration.

In some embodiments, the first build operation 1704 may access a database of electronic models of dental restorations and select one of the electronic models as a template. In one embodiment, the first build operation 1704 modifies the electronic model template to fit with surrounding anatomy of the patient. For example, the first build operation 1704 may modify an attribute table associated with the template model as described herein. In other embodiments, the first build operation 1704 may generate the first electronic model based, at least in part, on the surrounding anatomy of the patient.

Figure 18:
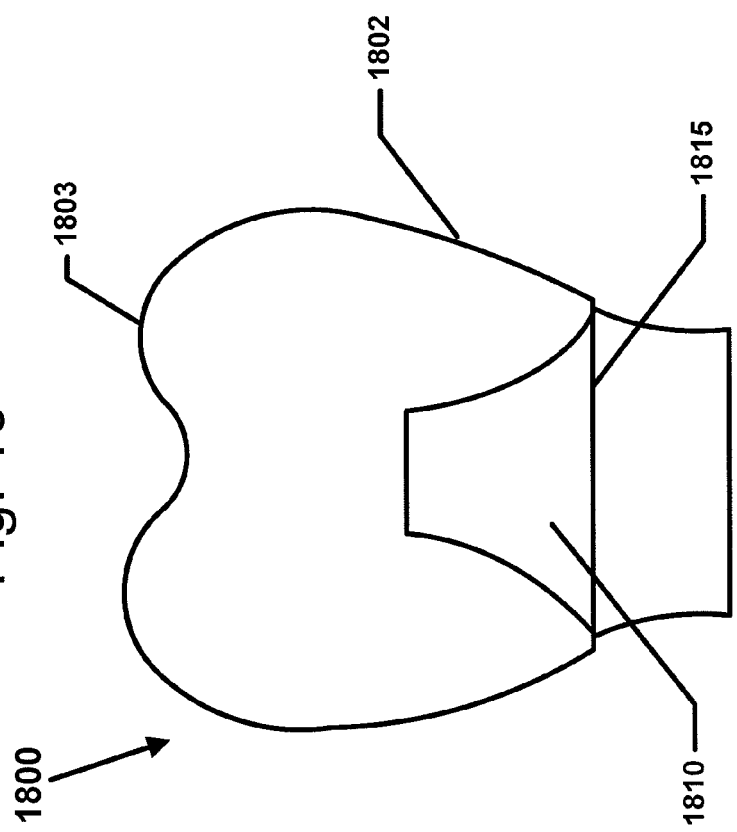

For example, in the embodiment shown in FIG. 18, the first build operation 1704 generates an electronic model of an exterior surface 1802 of a dental restoration 1800. In one embodiment, the exterior surface 1802 includes an occlusal surface 1803, which may be configured to interact with an antagonistic tooth (see FIG. 16), and sidewalls extending down to a margin curve 1815 of a preparation site 1810 of the patient. In another embodiment, the exterior surface 1802 may be a closed electronic model.

In one embodiment, the first build operation 1704 generates or deform the exterior surface 1802 so the occlusal surface 1803 is at least a predetermined distance away from the preparation site 1810 to ensure the dental restoration has sufficient thickness. For example, the first build operation 1704 may generate or deform the exterior surface 1802 to accommodate a coping substructure having a minimum thickness and a crown superstructure having a minimum thickness.

Figure 19:
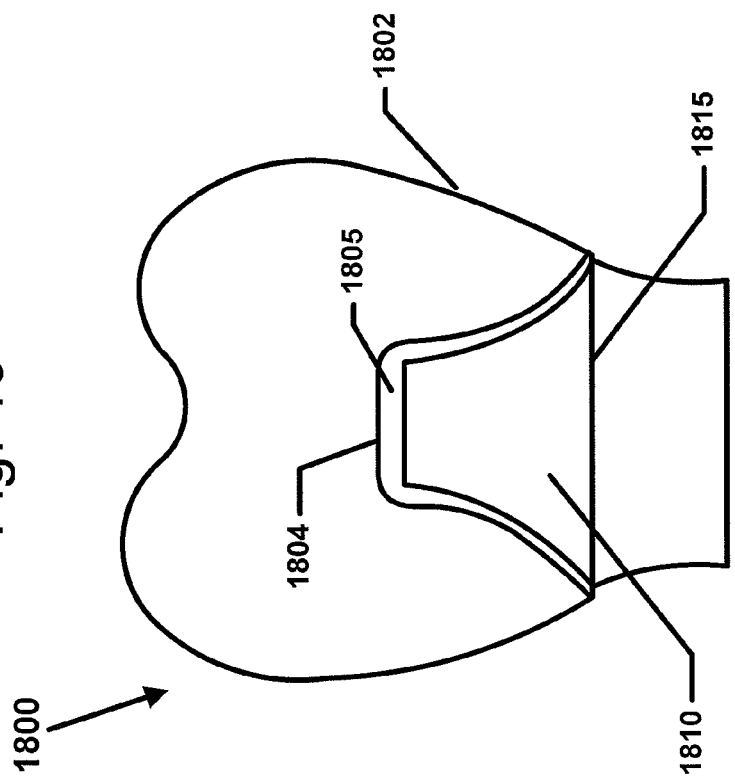

A second build operation 1706 obtains a second electronic model representing an abutment surface 1804 of the dental restoration (see FIG. 19). In one embodiment, the second build operation 1706 generates the abutment surface 1804 based on the electronic model 1810 of the preparation site. For example, in one embodiment, the second build operation 1706 may generate the second electronic model 1804 having a perimeter defined by the margin curve 1815. In another embodiment, the second build operation 1706 modifies an existing abutment surface of a closed electronic model of the exterior surface 1802.

In one embodiment, the second build operation 1706 positions the second electronic model of the abutment surface 1804 to leave a predetermined gap 1805 between the abutment surface 1804 and the preparation site 1810 to accommodate adhesive (not shown) for securing the fabricated dental restoration 1800 to the preparation site 1810. In one embodiment, the second build operation 1706 generates the abutment surface 1804 to leave about a 0.05 mm gap.

A third build operation 1708 generates a third electronic model of an exterior surface 1806 of a coping substructure 1807, which may cooperate with the abutment surface 1804 of the dental restoration 1800 to form the coping substructure 1807 (see FIG. 20). In some embodiments, the third build operation 1708 produces a coping substructure having a substantially constant thickness. For example, in one embodiment, the third build operation 1708 generates the exterior surface 1806 based upon a predetermined offset from the abutment surface 1804. In another embodiment, the third build operation 1708 generates the exterior surface 1806 of the coping substructure 1807 based on a fixed offset from the crown exterior 1802.

In some embodiments, the third build operation 1708 determines the offset amount based on one or more preset offset values. In one embodiment, the preset offset values are obtained experimentally. In another embodiment, the third build operation 1708 may determine the offset amount based on material properties of the fabrication material. In another embodiment, the third build operation 1708 may determine the offset amount based on a value input by a dental technician or other user.

In other embodiments, the third build operation 1708 generates and/or modifies the third electronic model of the coping exterior 1806 to have a variable thickness. In one embodiment, the third build operation 1708 may generate and/or modify the third electronic model 1806 to have sufficient thickness to support a corresponding crown portion of the restoration 1800.

FIG. 21 illustrates the difference between building a coping exterior surface 2106 to provide a coping substructure with a generally uniform thickness and building a coping exterior surface 2156 to produce a coping substructure having a variable thickness configured to provide support for a crown superstructure 2111. A first electronic model of a dental restoration 2100 in FIG. 21 includes a coping exterior surface 2106 generated based on a uniform offset from either an abutment surface (not shown) or a preparation site (not shown). A second electronic model of the dental restoration 2150 includes a coping exterior surface 2156 generated to provide support for the corresponding crown superstructure 2111. For example, the exterior surface 2156 deforms upwardly towards a cusp of the crown superstructure 2111 to provide support for the extra fabrication material that will be needed to form the cusp.

For example, in a preferred embodiment, the third build operation 1708 generates the third electronic model of the coping exterior surface 1806 based on a uniform offset from the abutment surface 1804 (e.g., see coping substructure 2100 of FIG. 21) and deforms the coping exterior surface 1806 (e.g., see coping substructure 2150 of FIG. 21) to meet the following constraints:

1. Minimum coping thickness L (FIG. 20);
2. Minimum crown thickness M (FIG. 20); and
3. Maximum crown thickness N (FIG. 20).

In some embodiments, the third build operation 1708 also to generate and/or modify the coping exterior surface 1806 based on the following additional constraints.

4. Uniform crown thickness; and
5. Minimize coping volume.

For example, the third build operation 1708 may determine a minimum coping thickness L for the coping substructure 1807 and initially offset the coping exterior surface 1806 by at least the minimum thickness L. The third build operation 1708 also may determine a minimum thickness M and a maximum thickness N for the crown superstructure. If an initial distance between the crown exterior 1802 and the coping exterior 1806 (e.g., based on the initial offset of the coping exterior 1806) exceeds the maximum thickness N, then the third build operation 1708 may deform the coping exterior surface 1806 outwardly to provide additional support for the crown exterior 1802 (e.g., see FIG. 23). If the distance between the crown exterior 1802 and the coping exterior 1806 does not meet the minimum crown thickness M, however, then the third build operation 1708 may deform the coping exterior surface 1806 inwardly unless such a deformation would violate the minimum coping thickness L.

The third build operation 1708 also may generate the coping exterior 1806 to include a collar 1808 configured to support a crown superstructure 1811 (e.g., see FIGS. 22 and 23). The collar 1808 is formed by extending at least part of the exterior surface 1806 of the coping substructure 1807 laterally outwardly past the interior surface 1804. In one embodiment, the collar 1808 is a partial collar extending outwardly on the lingual side of the coping exterior 1806 so that the collar 1808 or other portion of the coping substructure 1807 are not visible on the facial side of the dental restoration. In other embodiments, the third build operation 1708 may build a collar 1808 extending over any portion of the perimeter of the exterior surface 1806.

In some embodiments, the third build operation 1708 enables the user to specify and/or modify properties of the collar 1808. For example, in one embodiment, when the third build operation 1708 generates the coping exterior surface 1806, the third build operation 1708 may allow the user to specify a collar height H, a collar width W, and/or a portion of the perimeter of the coping exterior surface 1806 along which the collar 1808 should extend (see FIG. 22). In another embodiment, the third build operation 1708 may enable a user to deform a generated collar 1808 to an appropriate height H, width W, or location.

In other embodiments, however, the third build operation 1708 automatically generates a collar 1808 where appropriate to provide support for the crown superstructure 1811. In one embodiment, the third build operation 1708 may generate a collar 1808 based on the exterior surface of the dental restoration 1802. For example, the third build operation 1708 may generate the exterior coping surface 1806 to extend to the emersion profile 1814 of the dental restoration 1802 (e.g., see FIG. 23). In another embodiment, the third build operation 1708 may generate the collar 1808 based on the thickness of the crown (e.g., which may be approximated using the distance between the crown exterior surface 1802 and the coping exterior surface 1806).

A fourth build operation 1710 generates a crown interior surface 1809 to cooperate with the crown exterior 1802 to form a crown superstructure 1811 (see FIG. 24). In some embodiments, the fourth build operation 1710 generates the crown interior surface 1809 based on a uniform offset from the coping exterior 1806. For example, in one embodiment, the fourth build operation 1710 generates the crown interior surface 1809 to provide a sufficient gap between the coping substructure 1807 and the crown exterior 1811 to accommodate an opaque layer added to the fabricated coping substructure 1807.

In another embodiment, the fourth build operation 1710 generates the crown interior surface 1809 based on a uniform offset from the crown exterior 1802 to obtain an appropriate crown thickness. In certain embodiments, the fourth build operation 1710 generates the crown interior surface 1809 to produce a crown superstructure 1811 having a thickness ranging from about 0.5 millimeters to about 3 millimeters. In one embodiment, the fourth build operation 1710 generates the crown interior surface 1809 to produce a crown superstructure 1811 having a thickness of about 1.5 millimeters. In other embodiments, the fourth build operation 1710 may generate and/or deform the crown interior surface 1809 to have a variable thickness. The design process 1700 completes and ends at a stop module 1712.

In some embodiments, the steps of the design process 1700 are performed primarily by one or more computer processors. In other embodiments, however, one or more users may perform one or more of the steps either manually or interactively on a computing device. For example, in one embodiment, users may adjust (e.g., via input devices 150 of FIG. 1) the electronic models of the surfaces 1802, 1804, 1806, 1809 displayed to the users (e.g., via output devices 151) to provide space in which material (e.g., adhesive, an opaque layer, etc.) may be added after fabrication. In another embodiment, one or more users may adjust the electronic models of the surfaces 1802, 1804, 1806, 1809 to better accommodate the other surfaces.

Additional Design Features

Optional design features which may be added to dental restorations or other dental appliances will now be discussed. These design features may be added to any of the dental appliances disclosed herein.

Figure 25:
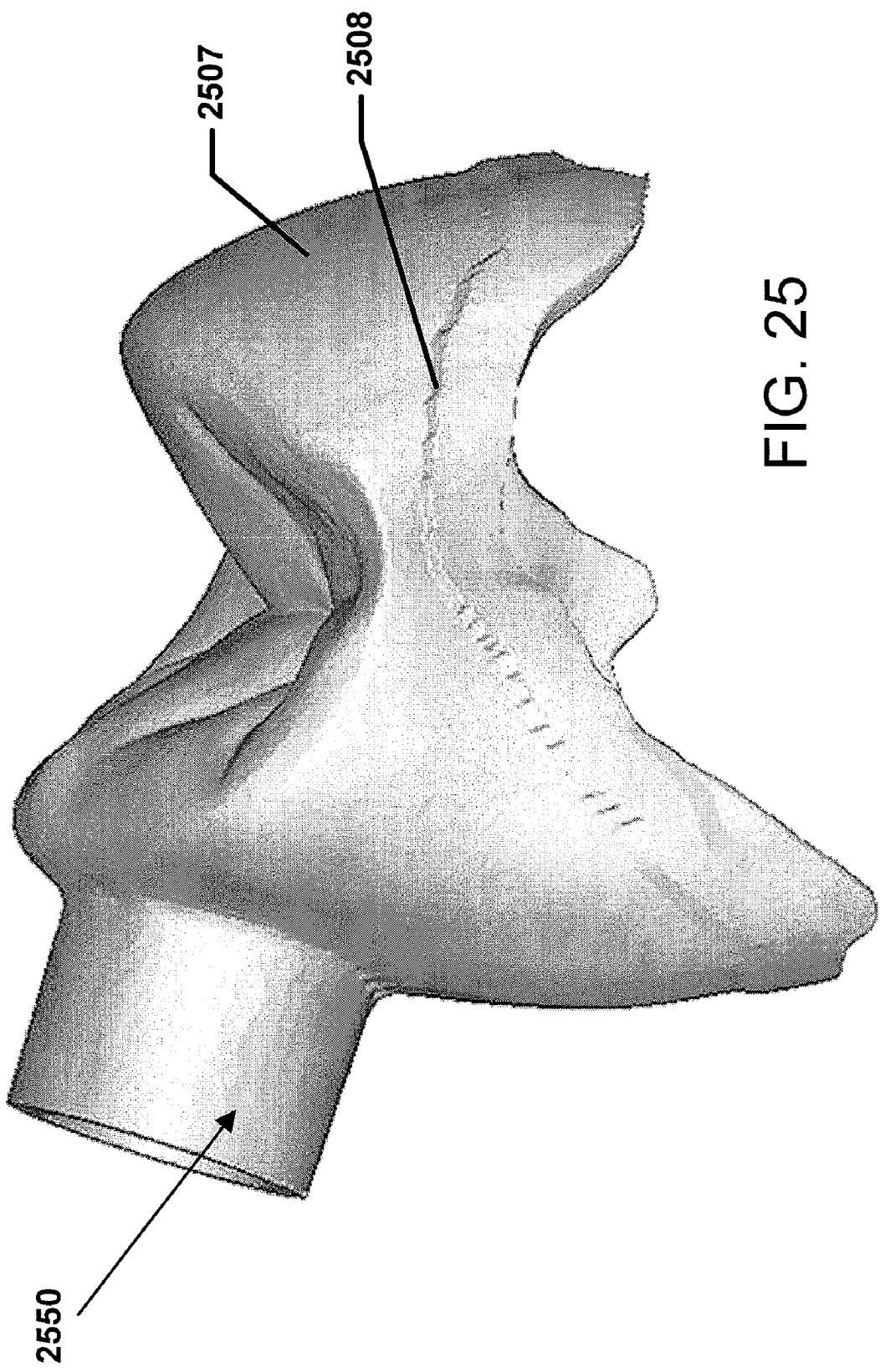
FIG. 25 is a perspective view of a coping superstructure including a sprue former arranged in accordance with the principles of the present disclosure.

For example, as shown in FIG. 25, sprue formers 2550 may be added to dental components that are fabricated through a casting process (e.g., a lost-wax casting procedure). In general, sprue formers 2550 enable casting of patterns by forming passages in a casting or pressing mold through which the fabrication material (e.g., metal, ceramic, etc.) may be conveyed. In one embodiment, sprue formers 2550 may be added automatically to any dental component to be cast. In another embodiment, a user may select a location and orientation of the sprue former 2550 for each dental component. Additional details regarding sprue formers may be found in U.S. application Ser. No. 11/983,083, filed Nov. 7, 2007, (issued as U.S. Pat. No. 7,946,334) the disclosure of which is hereby incorporated herein by reference.

Figure 26:
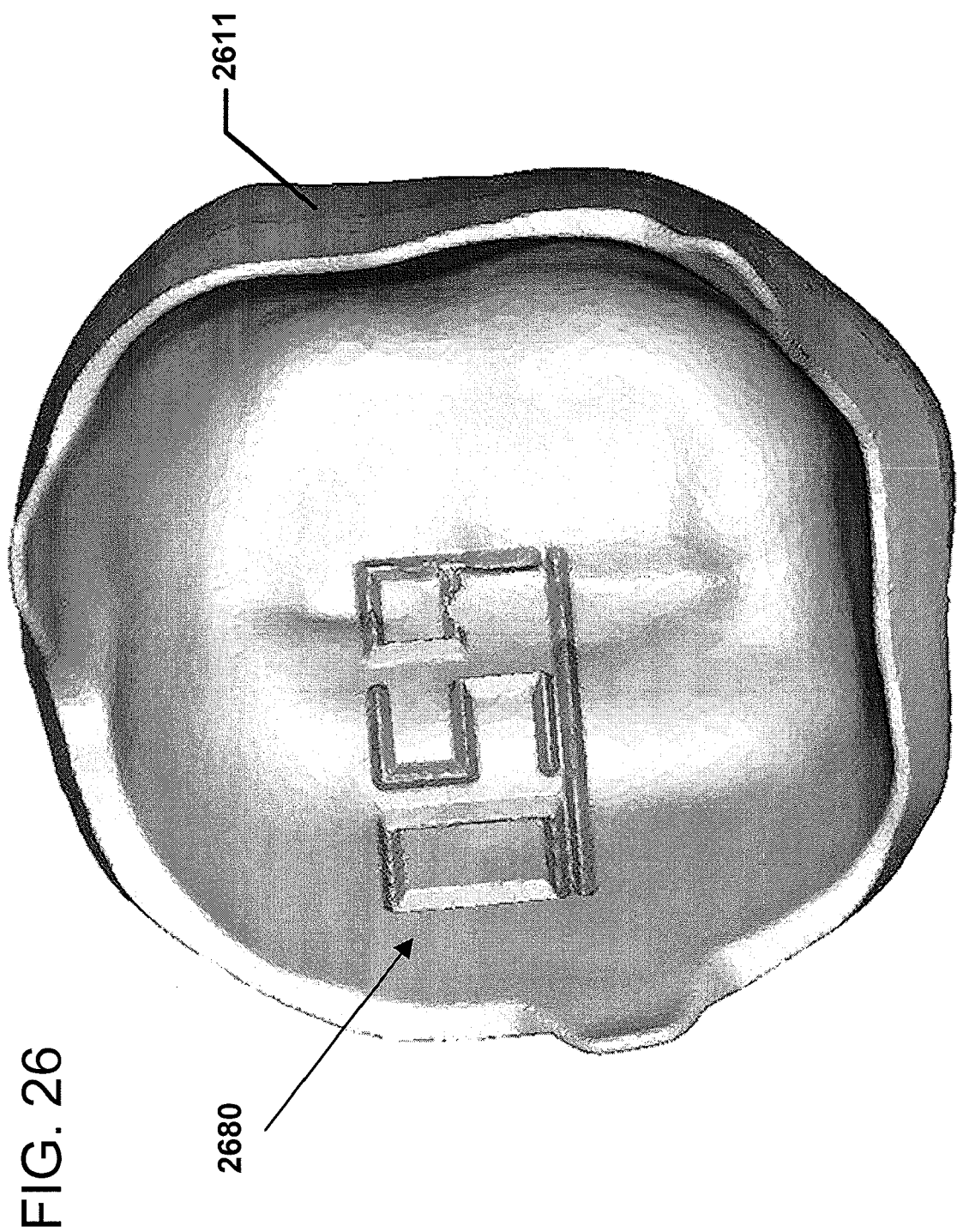
FIG. 26 is a plan view of an interior surface of a crown superstructure to which a serial number has been added in accordance with the principles of the present disclosure.

In other embodiments, unique identification numbers 2680 or batch numbers may be added to one or more components of the dental appliances during the design phase to track fabricated components during the manufacturing phase (e.g., see FIG. 26). For example, the identifications numbers 2680 may be added to the electronic models of the dental components (e.g., by an automated process, through interaction with the user, etc.) and accordingly printed or etched onto the dental components when the components are fabricated. In the example shown in FIG. 26, a serial number 2680 has been added to the bottom of an electronic model of a crown superstructure 2611. In other embodiments, the identification numbers 2680 may be added to any suitable portion of a dental component.

Referring to FIGS. 37-42, maintaining an appropriate distance between dental components during a casting process can be difficult. Adding tabs and a coupling material to one or more components may facilitate proper positioning between the dental components. For example, adding tabs to a crown superstructure may facilitate positioning a fabricated pattern of a crown superstructure on a fabricated coping substructure during a casting process. The crown pattern and fabricated coping may further be held together using a wax or other adhesive substance.

Figure 37:
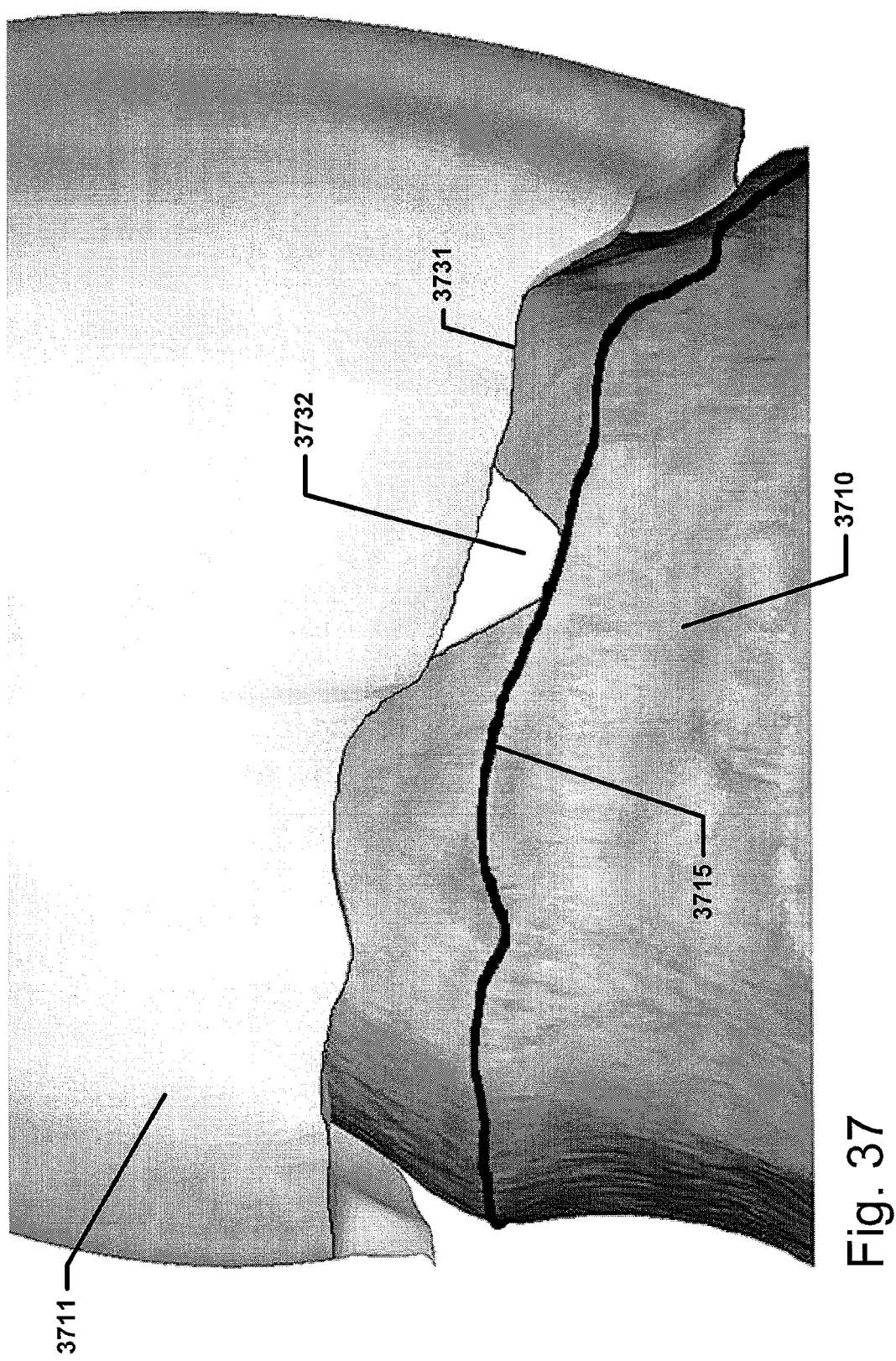
FIG. 37 is a perspective view of a crown superstructure having tabs extending to a margin curve of a corresponding preparation site in accordance with the principles of the present disclosure.
Figure 38:
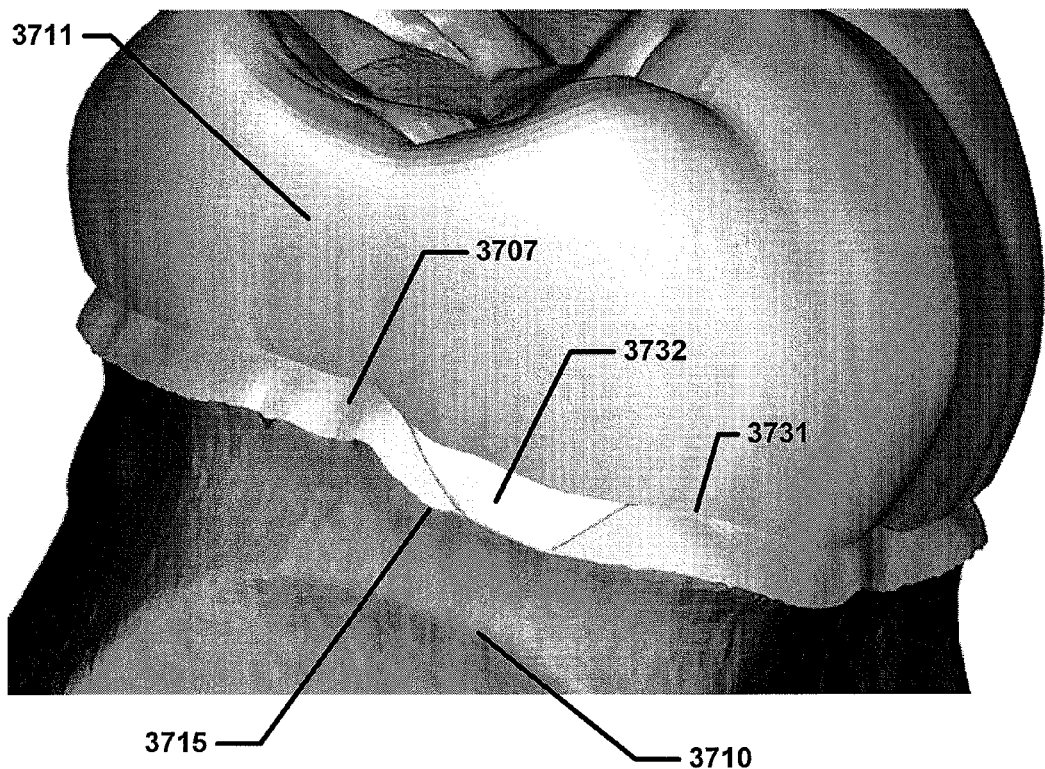
FIGS. 38 and 39 are perspective views of crown superstructures that have tabs and that are mounted over coping substructures arranged on preparation sites in accordance with the principles of the present disclosure.
Figure 39:
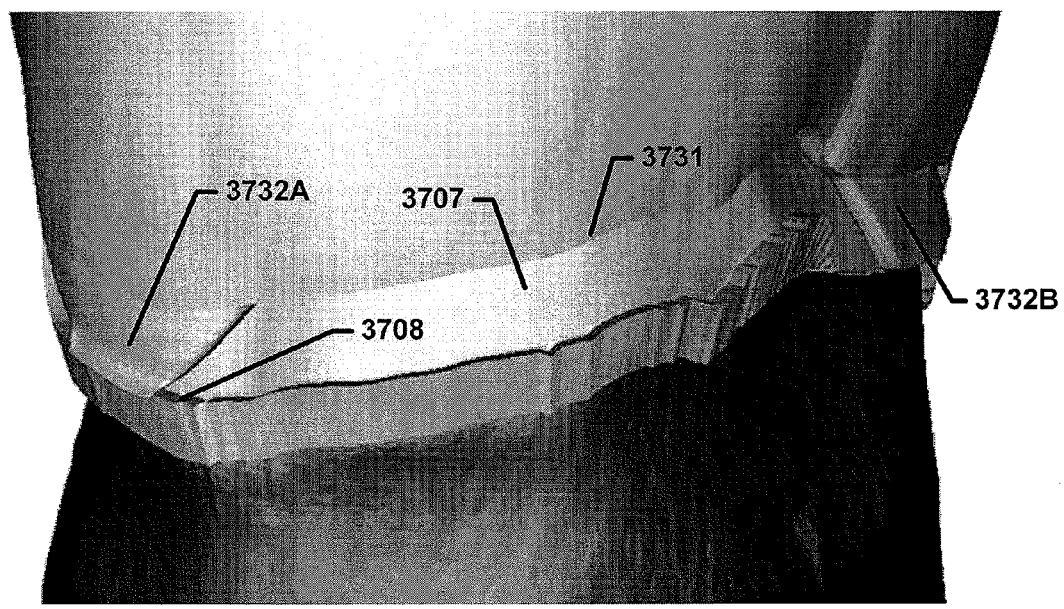

FIG. 37 is a partial perspective view of an electronic model of a crown superstructure 3711 having tabs 3732 extending away from the perimeter of the crown superstructure 3711. In general, the tabs 3732 extend from a perimeter 3731 of the crown superstructure 3711 toward a margin curve 3715 of a preparation site 3710. FIGS. 38 and 39 are partial perspective views of the electronic model of the crown superstructure 3711 arranged over a coping substructure 3707.

In one embodiment, the tabs 3732 of the crown superstructure 3711 sit upon a collar 3708 of the coping substructure 3707 to maintain the crown superstructure 3911 at a fixed position relative to the coping substructure 3707 (e.g., see tab 3732A of FIG. 39). In other embodiments, however, the tabs 3732 may extend over the coping substructure 3707 to the depth of the margin curve 3715 of the preparation site 3710 (e.g., see tab 3732B of FIG. 39).

Figure 40:
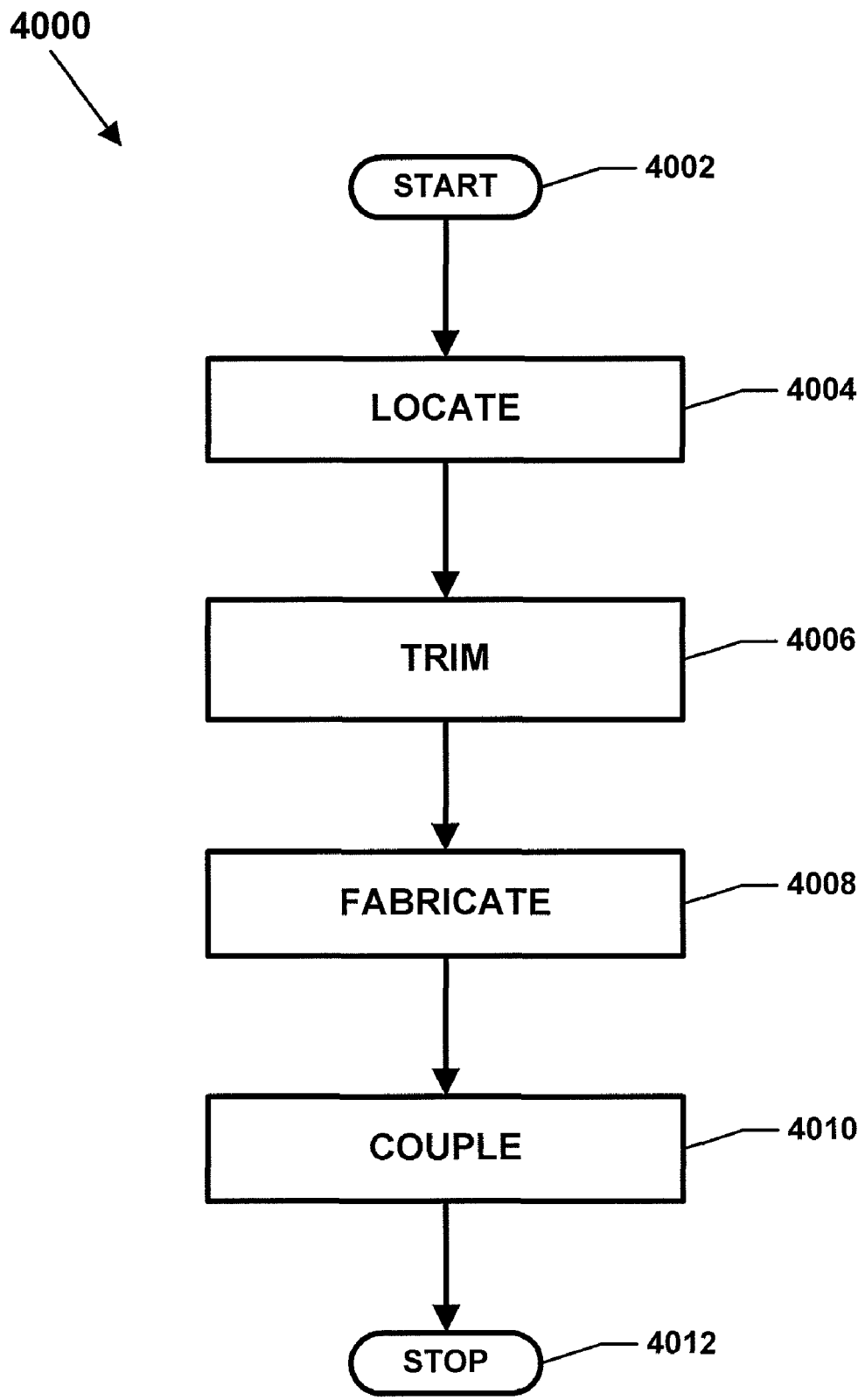
FIG. 40 is a flowchart illustrating an operational flow for an example positioning process by which tabs and coupling material may be utilized with a crown superstructure and coping substructure of a dental restoration to enhance casting performance in accordance with the principles of the present disclosure.
Figure 42:
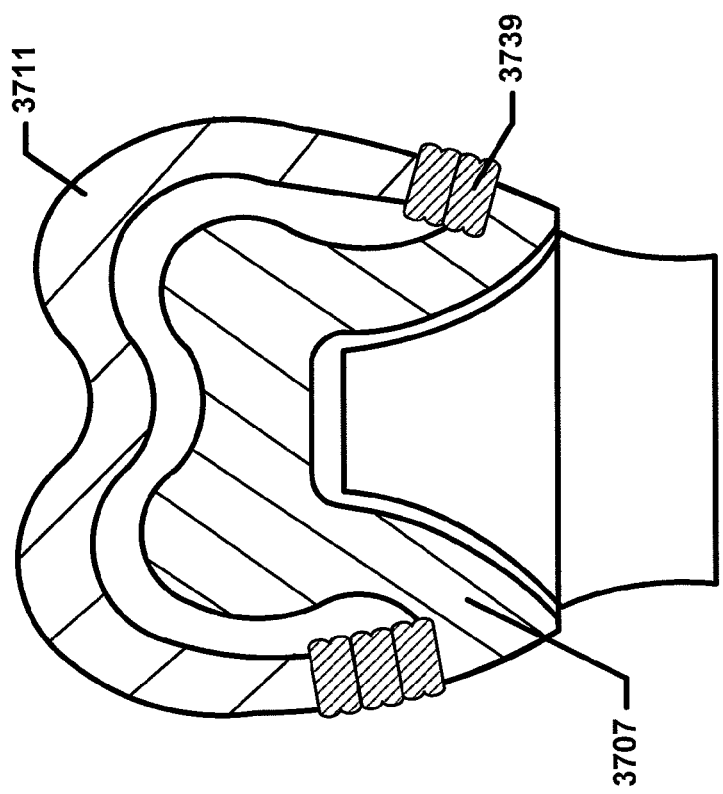
FIGS. 41 and 42 are schematic block diagrams of showing exemplary the results of the positioning process of FIG. 40 in accordance with the principles of the present disclosure.
Figure 41:
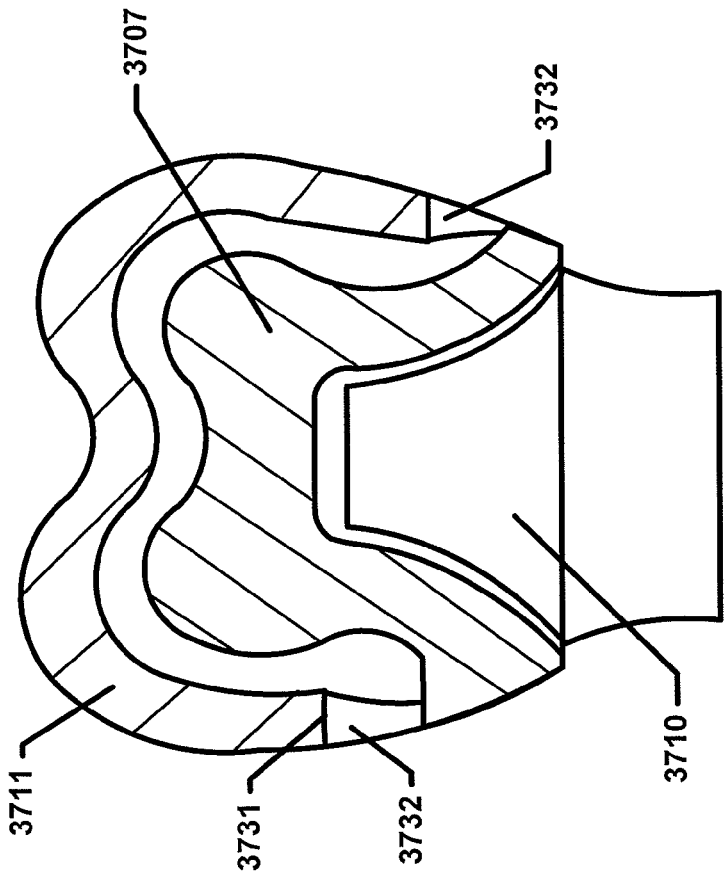

FIG. 40 is a flowchart illustrating an operational flow for an example positioning process 4000 by which tabs and coupling material may be utilized with a crown superstructure and coping substructure of a dental restoration to enhance casting performance. The positioning process 4000 initializes and begins at a start module 4002 and proceeds to a locate operation 4004.

The locate operation 4004 determines positions on a crown superstructure, such as crown superstructure 3711 of FIGS. 37-39, at which one or more tabs, such as tabs 3732 of FIGS. 37-39, may be added. In some embodiments, the locate operation 4004 automatically determines appropriate locations for a predetermined number of tabs. In one embodiment, the locate operation 4004 automatically determines appropriate locations based on the anatomy of a corresponding coping substructure, such as coping substructure 3707 of FIGS. 38 and 39. In one embodiment, the locate operation 4004 determines locations for three tabs. In other embodiments, the locate operation 4004 enables a user to determine appropriate tab positions interactively.

A trim operation 4006 removes one or more sections of material from the crown superstructure 3711 adjacent the perimeter 3731 to form the tabs 3732. In one embodiment, portions of the perimeter 3731 of the crown superstructure 3711 are offset from the coping substructure 3707 (see FIGS. 37-39 and 41). The remaining portions of the perimeter 3731 form the tabs 3732 (see FIGS. 37-39 and 41). Offsetting the perimeter 3731 of the crown superstructure 3711 provides gaps between the perimeter of the crown superstructure 3711 and the perimeter of the coping substructure 3707. In one embodiment, the trim operation 4006 raises the perimeter 3731 of the crown superstructure 3711 from the perimeter of the coping substructure 3707 by about 1 mm.

A fabricate operation 4008 prints or otherwise produces a pattern of the crown superstructure 3711 for casting. The fabricate operation 4008 prints or mills the pattern (e.g., of wax) of the crown superstructure 3711 with tabs 3732. The fabricate operation 4008 also produces a coping substructure. For example, the fabricate operation 4008 may print, mill, cast, or otherwise produce the coping substructure 3707.

A couple operation 4010 attaches the pattern of the crown superstructure 3711 including the tabs 3732 to the fabricated coping substructure 3707. For example, wax or other adhesive 3739 (FIG. 42) may be added over the gaps formed by the offset perimeter of the crown superstructure 3711 to secure the crown superstructure pattern to the coping substructure 3707. The wax 3739 inhibits movement of the crown superstructure pattern relative to the coping substructure during a pressing process, thereby providing a pressing mold with increased accuracy. The positioning process 4000 completes and ends at a stop module 4012.

Dental Bridges

Other multi-piece dental appliances may be generated by first generating an electronic model for the exterior of the complete appliance and subsequently generating electronic models for the different components of the appliance. For example, copings of a bridge framework may be generated using the design process 1700 disclosed above. In addition, bridge connectors also may be generated based on one or more components of a bridge framework as described herein.

A dental bridge provides tooth replacements for one or more teeth at which a natural abutment (e.g., tooth stump) is not convenient or possible. Typically, the dental bridge includes multiple dental restorations fixedly coupled together and anchored at one or both ends to natural teeth. Each restoration of the dental bridge includes a crown superstructure mounted to a portion of a bridge framework, which is formed from at least one coping coupled to either a second coping (e.g., to form a splinted crown) or one or more pontics. Typically, the coping mounts to a prepared tooth (e.g., ground stumps of natural teeth, implanted abutments, etc.). In one embodiment, two copings support a pontic over edentulous tissue therebetween.

Figure 43:
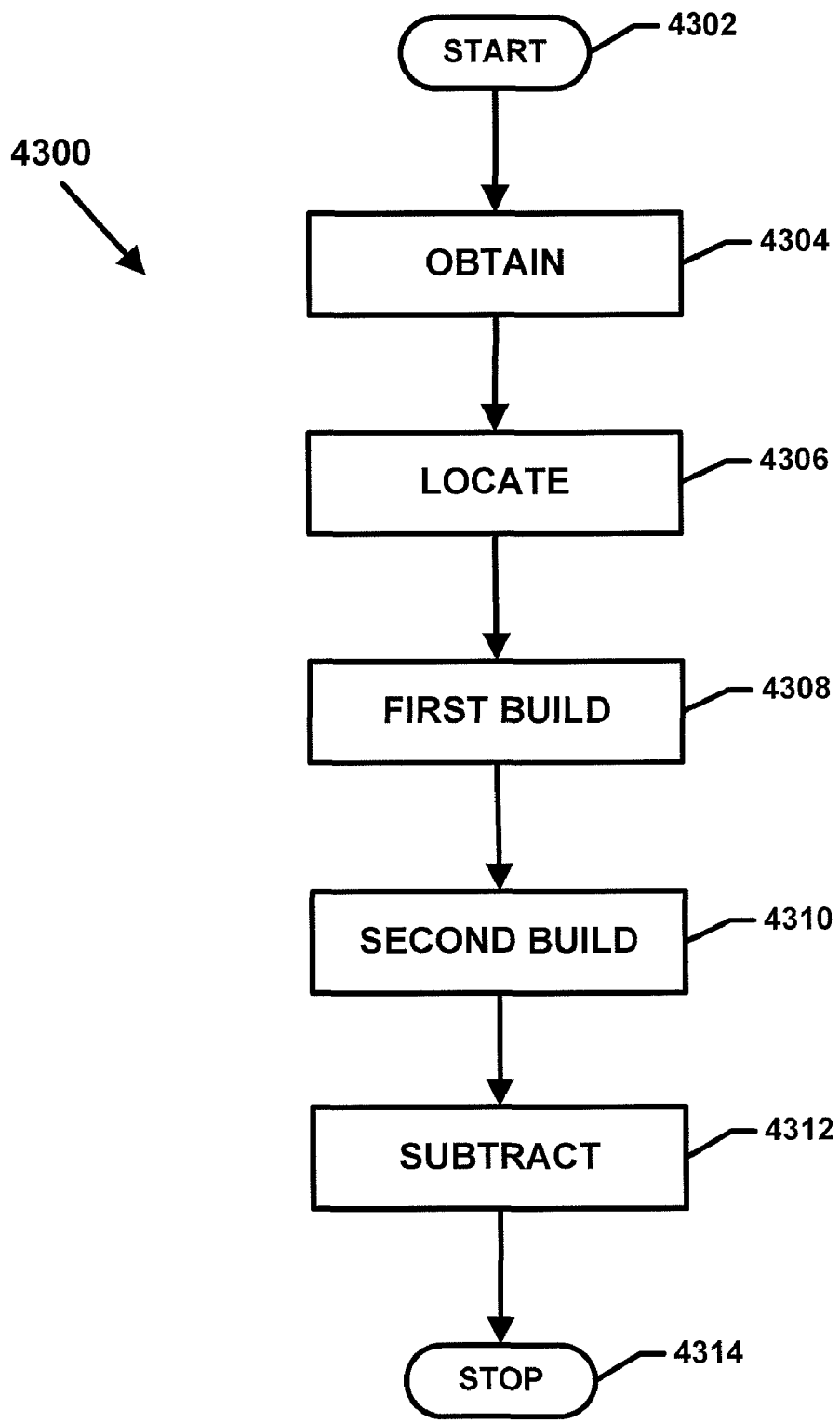
FIG. 43 is a flowchart illustrating an operational flow for an exemplary bridge design process implemented in accordance with the principles of the present disclosure.

FIG. 43 is a flowchart illustrating an operational flow for a bridge design process 4300. The bridge design process 4300 initializes and begins at the start module 4302 and proceeds to the obtain operation 4304. The obtain operation 4304 generates an electronic model of an appropriate section of the dentition and surrounding anatomy of the patient at which the dental bridge is to be installed. In one embodiment, the obtain operation 4304 generates the electronic model based on scanned positional data as described above.

A locate operation 4306 determines the number of teeth of the dentition to be replaced by the bridge appliance. The locate operation 4306 also identifies the same number of preparation sites and/or gaps of edentulous tissue within the electronic model of the dentition. In some embodiments, the locate operation 4306 presents the electronic model of the dentition and anatomy to the user and receives instructions from the user identifying the number of preparation sites and/or gaps and locations for each. In other embodiments, however, a computer processor may determine the number and arrangement of preparation sites and edentulous tissue based on identification rules.

The locate operation 4306 also may identify landmarks on the identified preparation sites and the edentulous tissue. For example, the locate operation 4306 may identify a margin curve for each tooth to be replaced by the bridge. In one embodiment, the margin curve for the tooth to be replaced by the pontic is generated on the gingival surface of the edentulous tissue below the pontic. In such an embodiment, the margin curve may be translated away from the gingival surface before generating the bridge components to inhibit designing a crown superstructure that would irritate the edentulous tissue.

A first build operation 4308 generates an electronic model of an exterior surface of a bridge appliance including one or more tooth substitutes (e.g., dental restorations). The tooth substitutes are arranged to interact with each other as natural teeth would. In general, the first build operation 4308 generates, obtains, or modifies the exterior surface model in accordance with the instructions and/or data acquired in the locate operation 4306.

In some embodiments, the first build operation 4308 retrieves a bridge template model from a library. In one embodiment, the first build operation 4308 retrieves the template model based on the appropriate number of teeth to be replaced, the type of teeth being replaced, and/or the number of pontics and coping substructures needed. In another embodiment, the first build operation 4308 may modify a standard bridge template to fit the preparation sites of the patient.

In other embodiments, the first build operation 4308 generates the electronic model of the exterior bridge surface to include an appropriate number of dental restorations as determined by the location operation 4306. For example, the first build operation 4308 may generate the dental restorations based on the landmarks (e.g., margin curves) identified in the surrounding anatomy of the patient. In one embodiment, the first build operation 4308 separately generates a dental restoration exterior surface for each tooth to be replaced and couples together the separately generated exterior surfaces.

Figure 44:
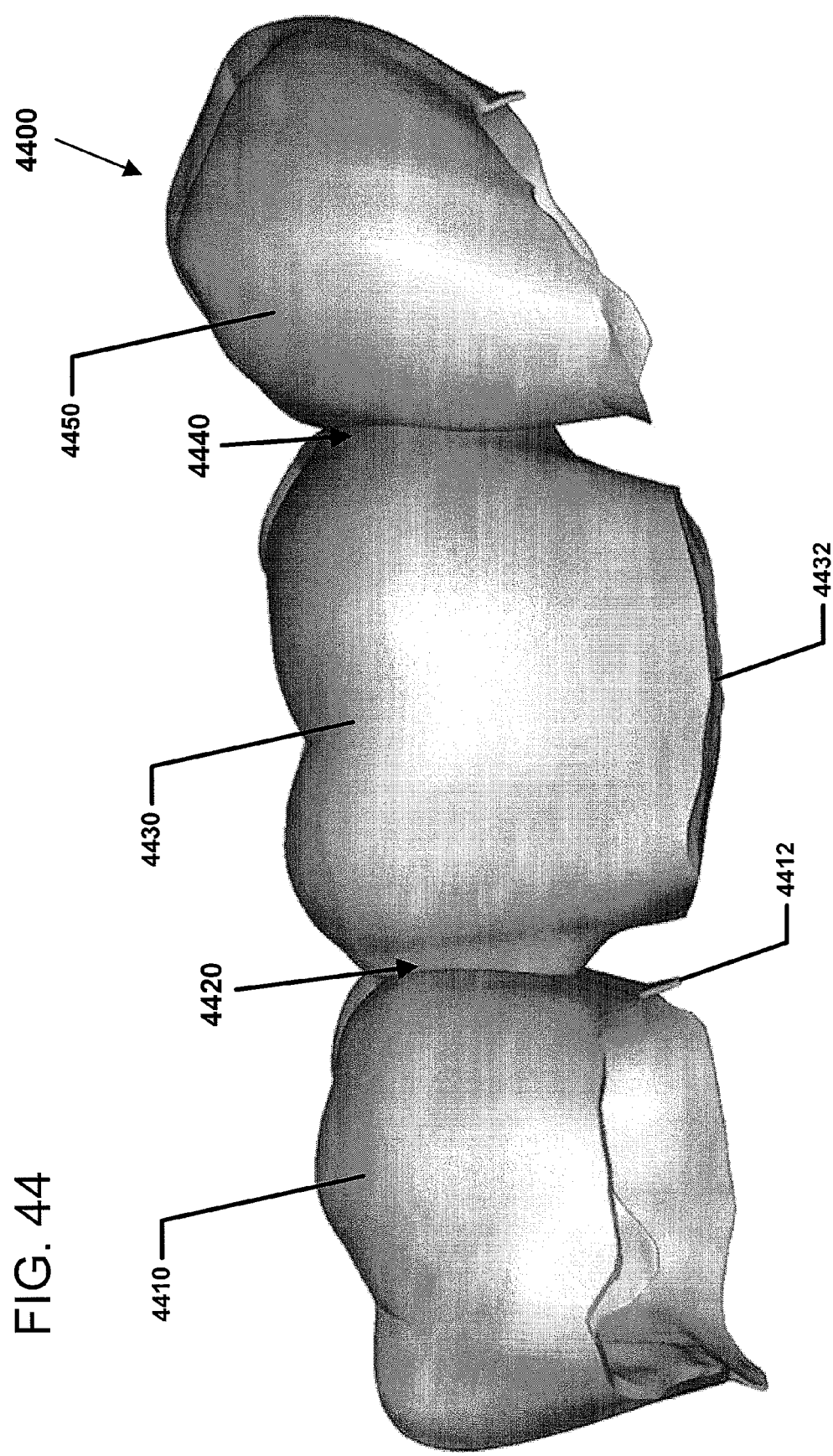
FIG. 44 is a perspective view of an electronic model of an exterior surface of a bridge appliance including an occlusal surface and sidewalls in accordance with the principles of the present disclosure.

One example of an exterior surface of a bridge appliance is shown at reference number 4400 of FIG. 44. The bridge appliance includes three dental restorations 4410, 4420, 4430 to replace three natural teeth of the patient. In the example shown, the three dental restorations 4410, 4430, 4450 are open models that are integrally connected along contact areas 4420, 4440. Typically, the dimensions and shape of the contact areas (i.e., interaction nexus) 4420, 4440 of the dental restorations is different for each restoration pair. In other embodiments, the bridge appliance may include closed and/or separate dental restorations.

A second build operation 4310 generates an electronic model of a bridge framework based on the bridge exterior surface model. In general, the bridge framework includes at least one pontic, at least one coping substructure, and at least one connector coupling the pontic to the coping substructure. In one embodiment, the second build operation 4310 generates the framework model to include one or more pontics supported between two coping substructures.

Figure 45:
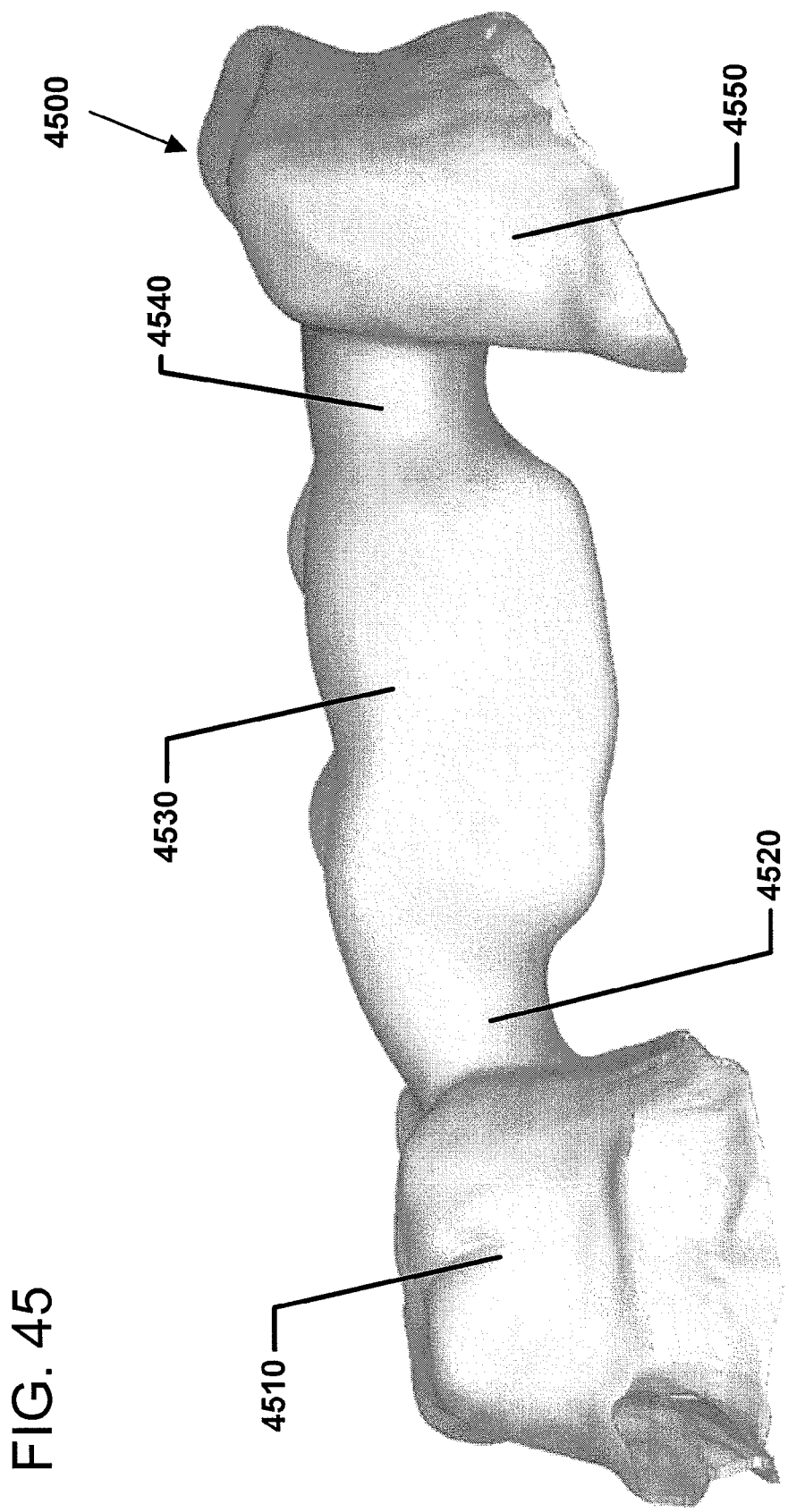
FIG. 45 is a perspective view of an exemplary bridge framework including a first coping substructure, a pontic, and a second coping substructure in accordance with the principles of the present disclosure.

FIG. 45 is a perspective view of an exemplary bridge framework 4500 including a first coping substructure 4510, a pontic 4530, and a second coping substructure 4550. A first connector 4520 couples together the first coping substructure 4510 and the pontic 4530 and a second connector 4540 couples together the pontic 4530 and the second coping substructure 4550. In other embodiments, the bridge framework 4500 may include additional pontics and/or coping substructures.

A subtract operation 4312 forms a crown top array (e.g., a combination of the crown superstructures for each of the dental restorations formed by the bridge appliance) to be mounted to the bridge framework. In general, the subtract operation 4312 forms the crown top array by removing the bridge framework electronic model, such as bridge framework 4500 of FIG. 45, from the bridge appliance electronic model, such as bridge appliance 4400 of FIG. 44. In one embodiment, the subtract operation 4312 forms an integral crown top array that may be installed on the bridge framework as a single piece. In another embodiment, the subtract operation 4312 forms a crown top array that may be fabricated and installed on the framework as multiple pieces.

In some embodiments, the subtract operation 4312 subtracts the framework by forming a bridge interior surface that cooperates with the bridge exterior surface to define the crown top array. In one embodiment, the subtract operation 4312 defines the bridge interior surface as an offset from the exterior surface of the bridge framework. In other embodiments, the subtract operation 4312 may remove volume occupied by the framework model from a closed bridge appliance model, thereby leaving behind a crown top array.

In some embodiments, the subtract operation 4312 also removes undercuts from the crown top array to facilitate installation of the crown top array on the framework. In one embodiment, the subtract operation 4312 removes the undercuts by determining a removal surface or removal volume of space that extends below the framework towards the preparation site and defining the bridge interior surface as being offset from the removal surface or removal volume.

Figure 46:
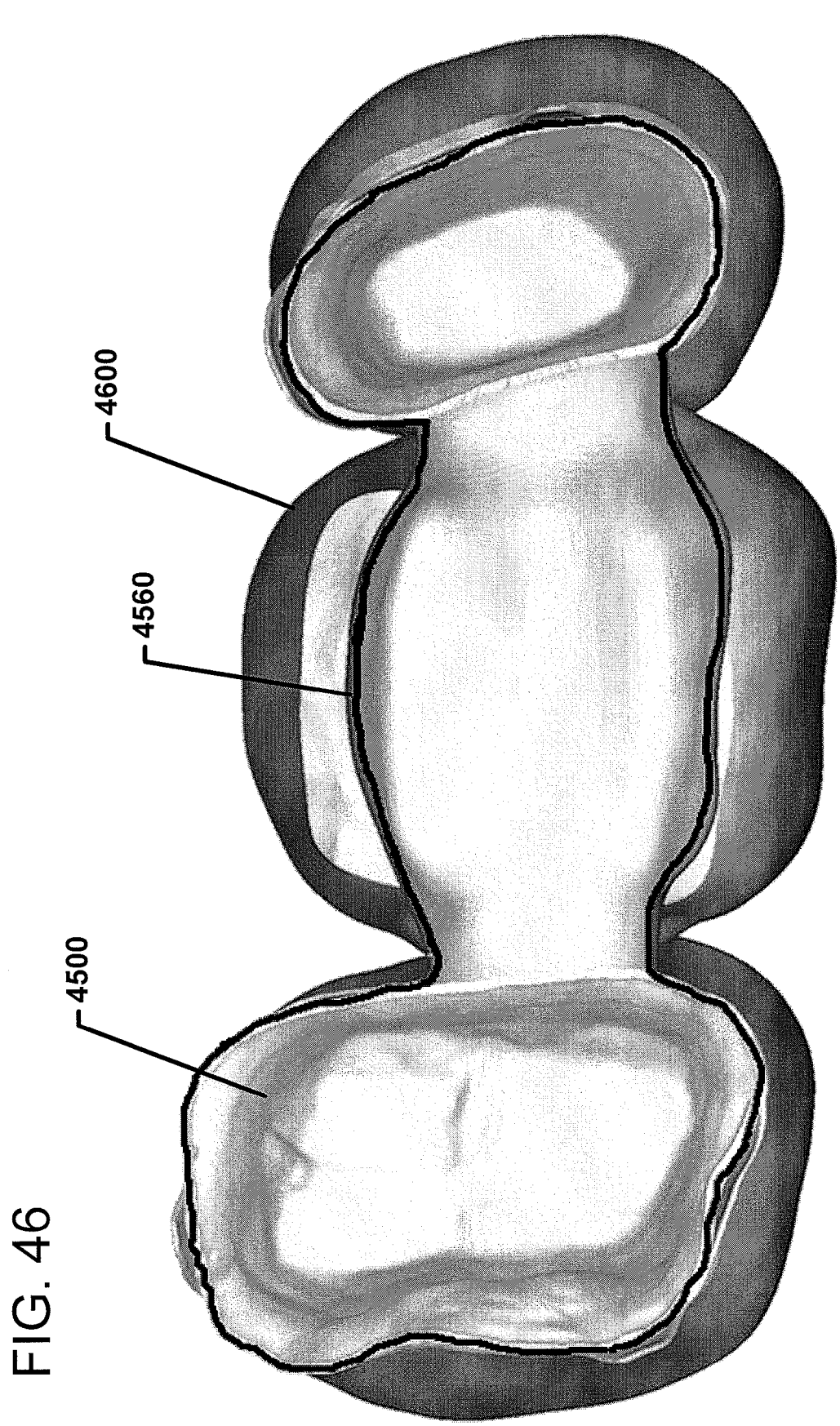
FIG. 46 is a plan view of the bridge framework of FIG. 45 arranged in cooperation with the bridge appliance of FIG. 44 in accordance with the principles of the present disclosure.
Figure 47:
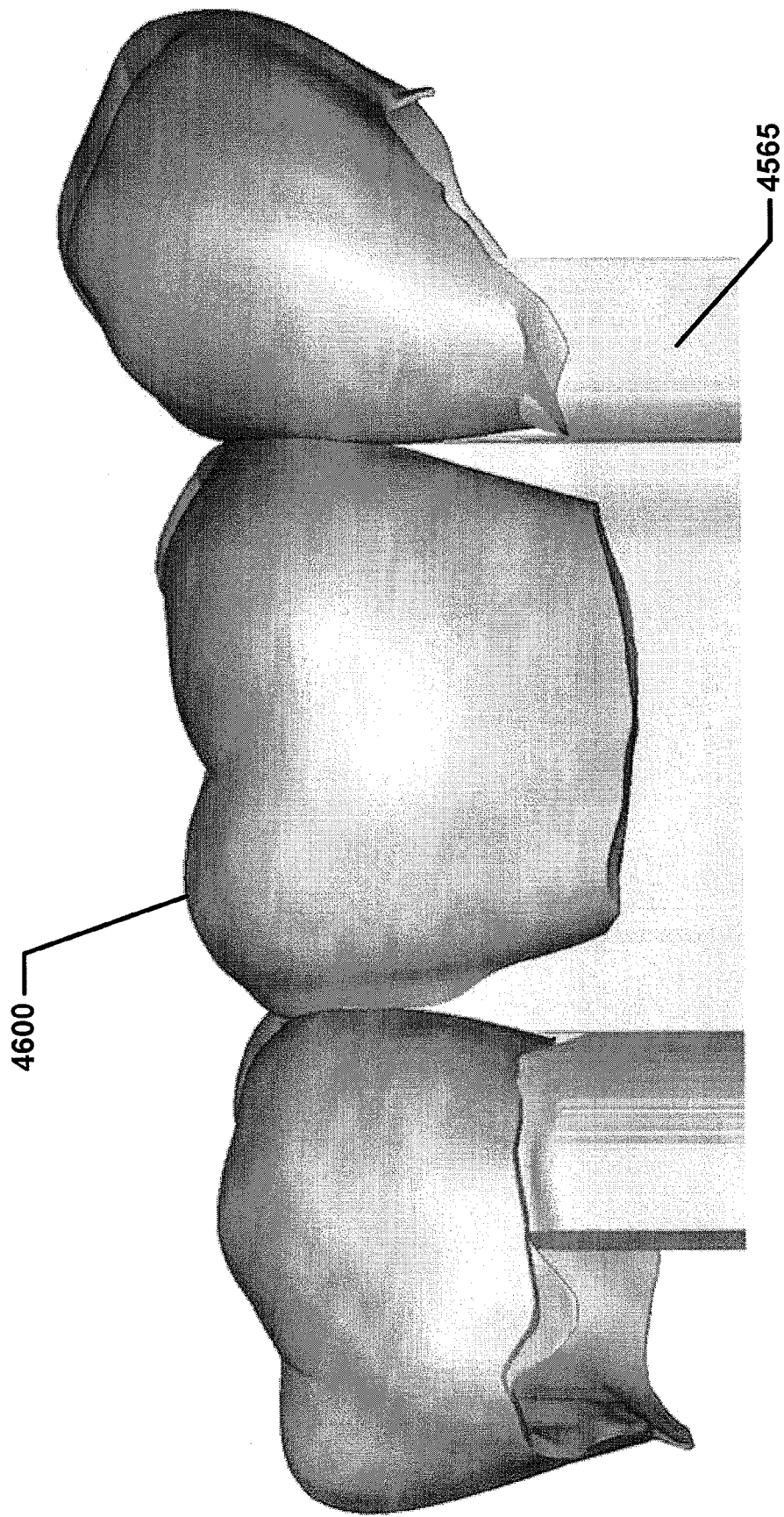
FIG. 47 is a perspective view of a bridge framework and corresponding removal surface being subtracted from the bridge appliance of FIG. 44 in accordance with the principles of the present disclosure.

For example, the bridge framework 4500 of FIG. 45 has a circumference 4560 as shown in FIG. 46. As shown in FIG. 47, the subtract operation 4312 may define a removal surface including the exterior surface of the framework 4500 and further including sidewalls 4565 defined by the circumference 4560 and extending towards a preparation site of the patient. The subtract operation 4312 defines a bridge interior surface based on a uniform or variable offset from the removal surface. The bridge interior surface cooperates with the bridge exterior surface to form a crown top array 4800 as shown in FIG. 48.

Portions of the bridge appliance 4600 that fall within the boundaries of the removal surface are removed from the bridge appliance model 4600. For example, a tab 4412 extending from the first dental restoration 4410 of FIG. 44 falls within the boundaries of the sidewalls 4565 shown in FIG. 46. Accordingly, the first dental restoration 4810 of the resulting crown top array 4800 shown in FIG. 48 does not include the tab.

Similarly, the second dental restoration 4430 of the bridge appliance 4400 of FIG. 44 is a closed electronic model. The surface of the second dental restoration 4430 closest to the preparation site falls within the boundaries of the removal surface shown in FIG. 47. Accordingly, the second dental restoration 4830 of the crown top array 4800 of FIG. 48 is an open electronic model without an abutment surface. The bridge design process 4300 completes and ends at a stop module 4314.

Figure 48:
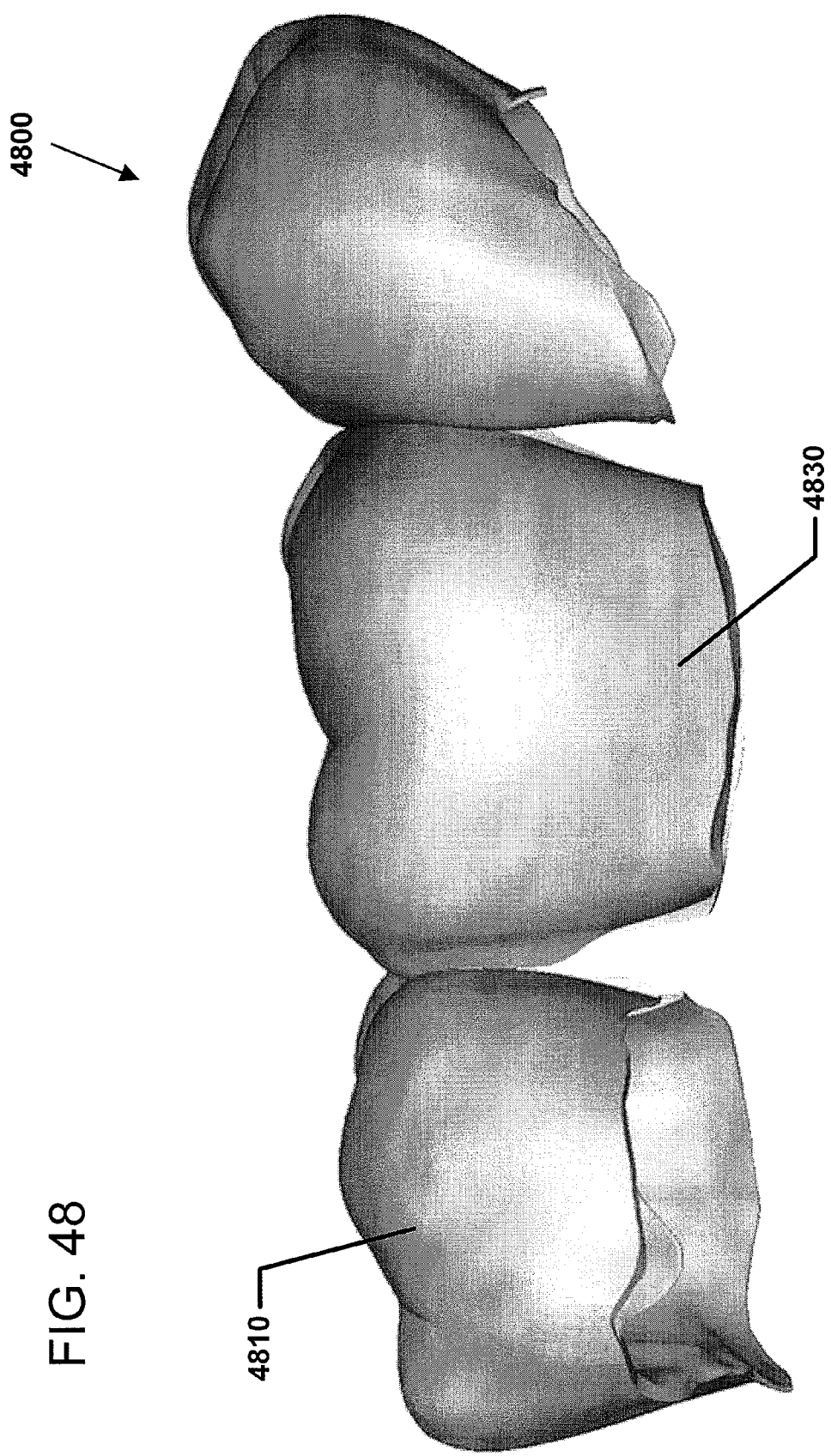
FIG. 48 is a perspective view of a crown-top array produced by subtracting the bridge framework and corresponding removal surface of FIG. 47 from the bridge appliance of FIG. 44 in accordance with the principles of the present disclosure.
Figure 49:
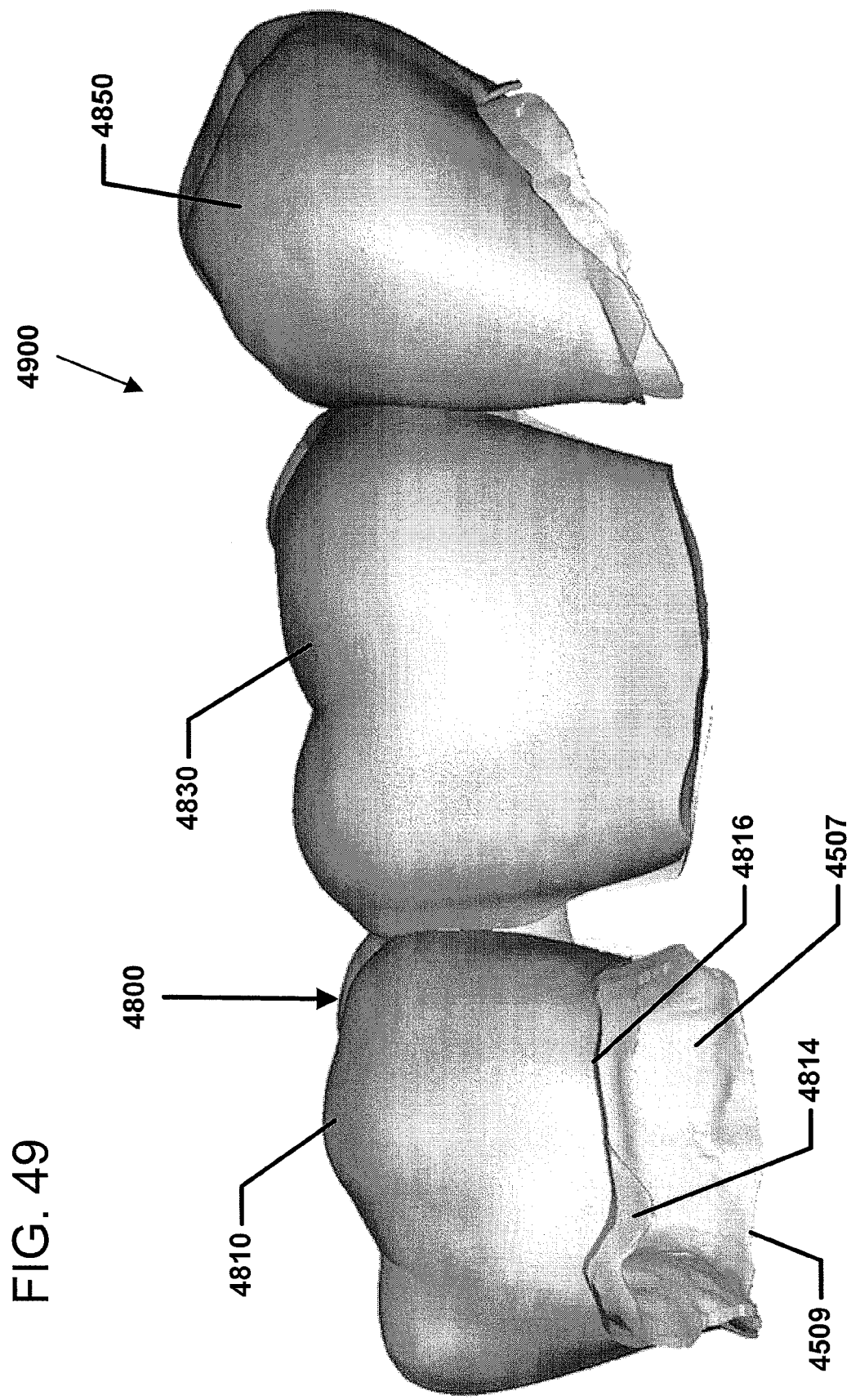
FIG. 49 is a perspective view showing an electronic model of a dental bridge including the crown top array of FIG. 48 installed over the framework of FIG. 45 in accordance with the principles of the present disclosure.

FIG. 49 is a perspective view showing an electronic model 4900 of a dental bridge including the crown top array 4800 of FIG. 48 installed over the framework 4500 of FIG. 45. In the example shown, the first dental restoration 4810 includes tabs 4814 extending from a perimeter 4816 of the crown top array 4800 offset from a perimeter 4509 of a corresponding coping substructure 4507. In other embodiments, however, each of the dental restorations of the crown top array 4800 may include fewer or greater tabs.

Figure 50:
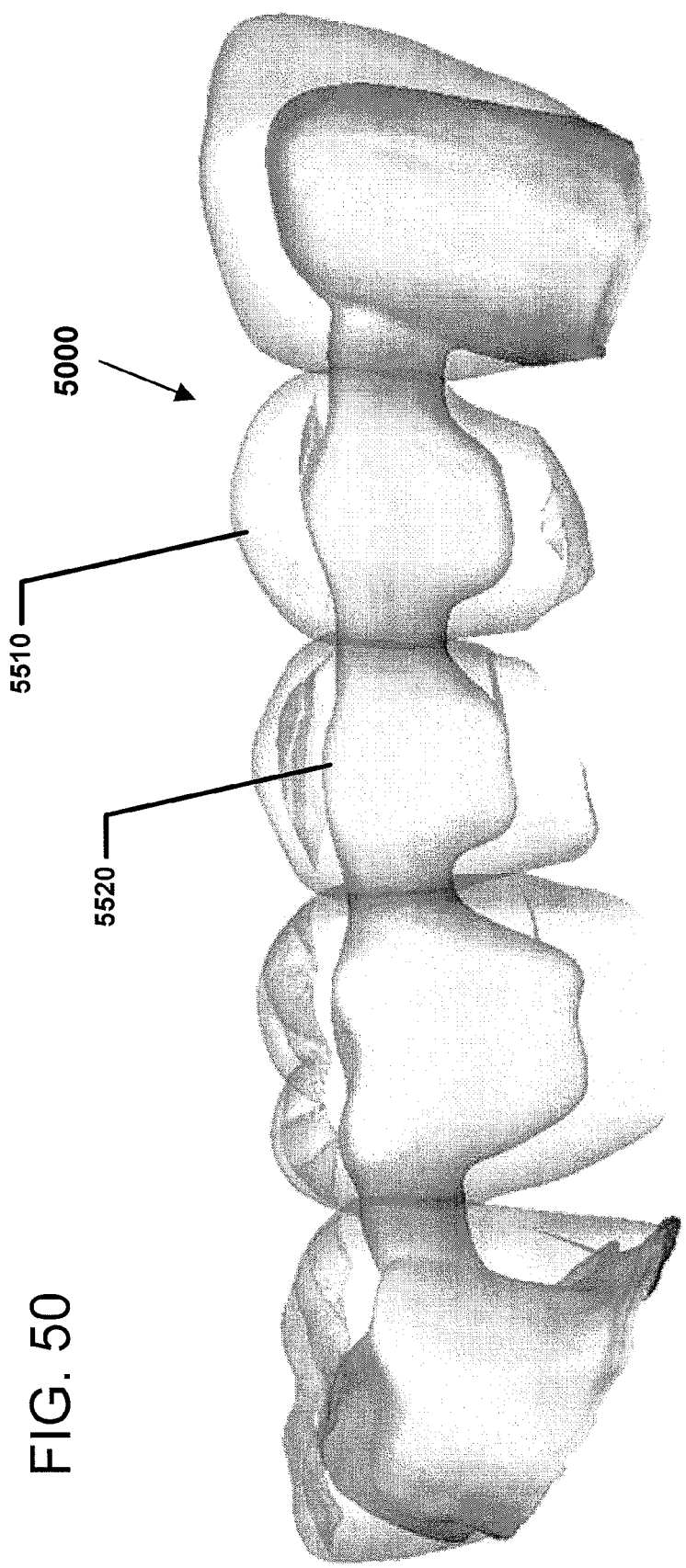
FIG. 50 is a perspective view of an electronic model of another dental bridge configured in accordance with the principles of the present disclosure.

FIG. 50 is a perspective view of an electronic model 5000 of another dental bridge. The dental bridge model 5000 includes a crown top array 5010 and framework 5020 configured to replace five teeth using two coping substructures to support three pontics. The crown top array 5010 of FIG. 50 has been made transparent to clarify the relationship and interaction between the crown top array 5010 and the framework 5020.

Figure 27:
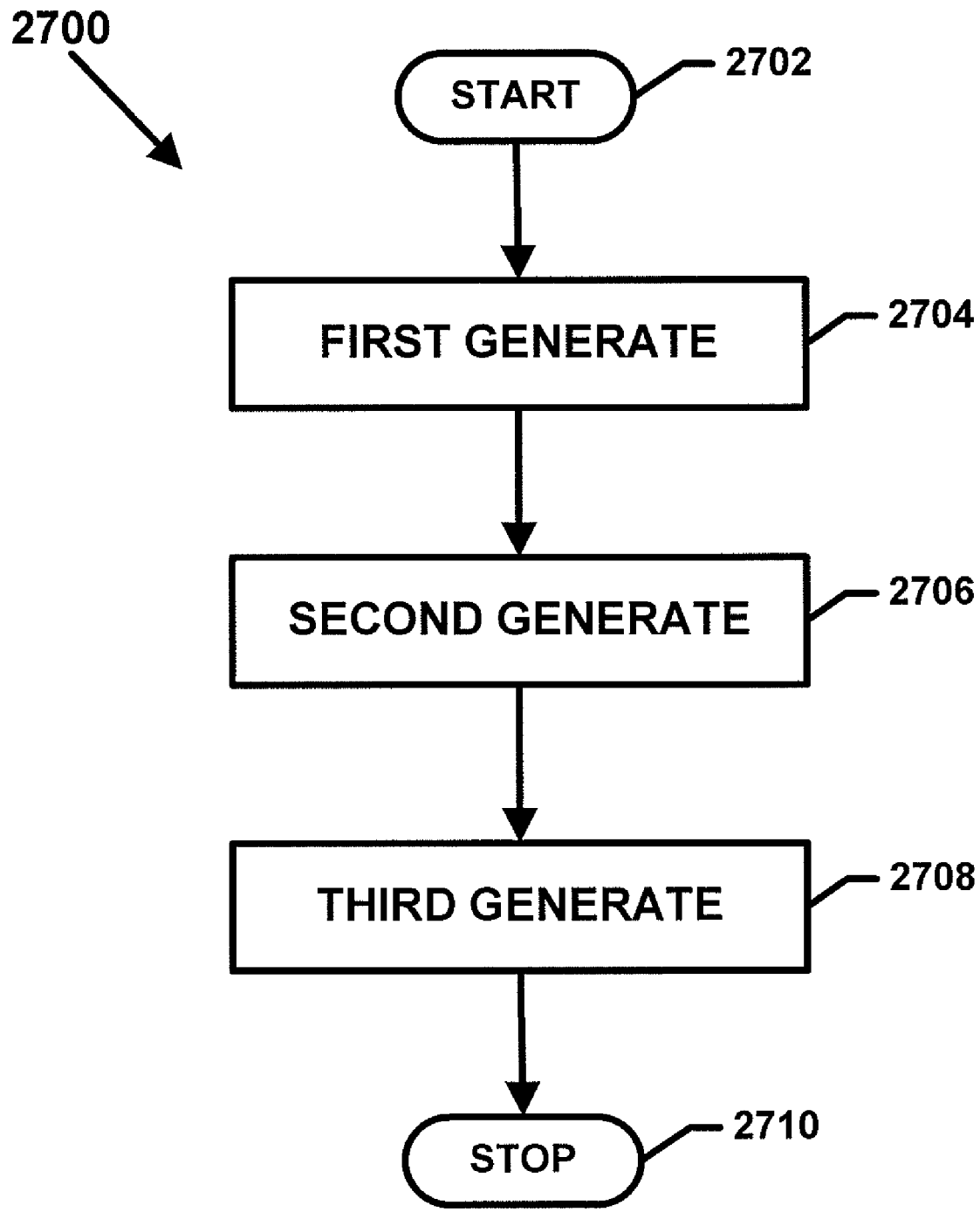
FIG. 27 is a flowchart illustrating an operational flow for a framework design process in accordance with the principles of the present disclosure.

Referring now to FIG. 27, a framework design process 5100 is one example process by which the second build operation 4310 of FIG. 43 may be implemented. The framework design process 2700 initializes and begins at a start module 2702 and proceeds to a first generate operation 2704. The first generate operation 2704 provides coping substructures for each of the natural teeth that will anchor and support the bridge appliance.

In some embodiments, the first generate operation 2704 generates the coping substructures based on the exterior surface of the bridge appliance. In one embodiment, the first generate operation 2704 follows at least part of the dental restoration design process 1700 of FIG. 17 to form the coping substructures. In other embodiments, however, the first generate operation 2704 may provide the coping substructures using any suitable process.

Figure 51:
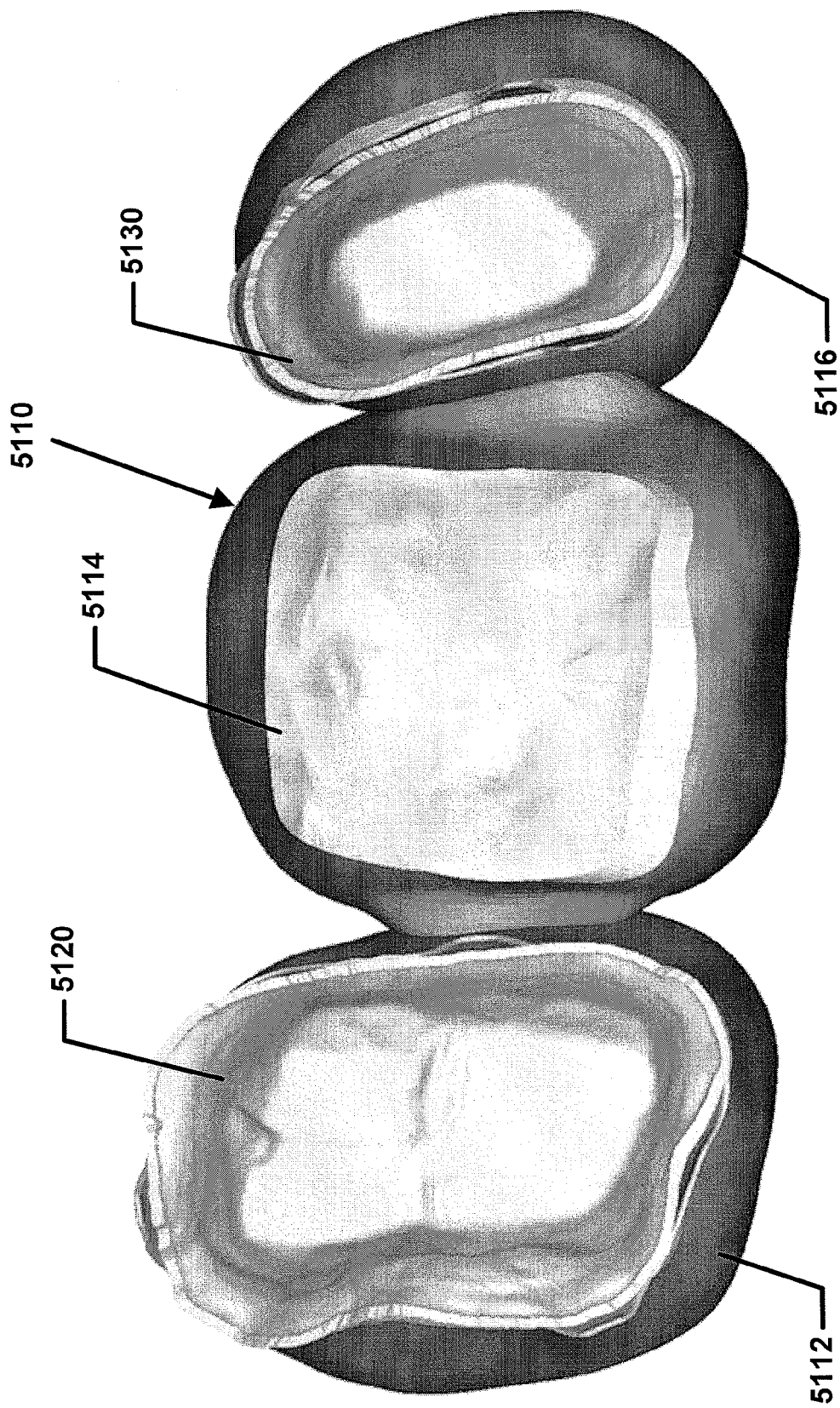
FIG. 51 is a plan view of the abutment surface of the coping substructures arranged within first and second outer dental restoration, respectively, of the bridge appliance in accordance with the principles of the present disclosure.
Figure 52:
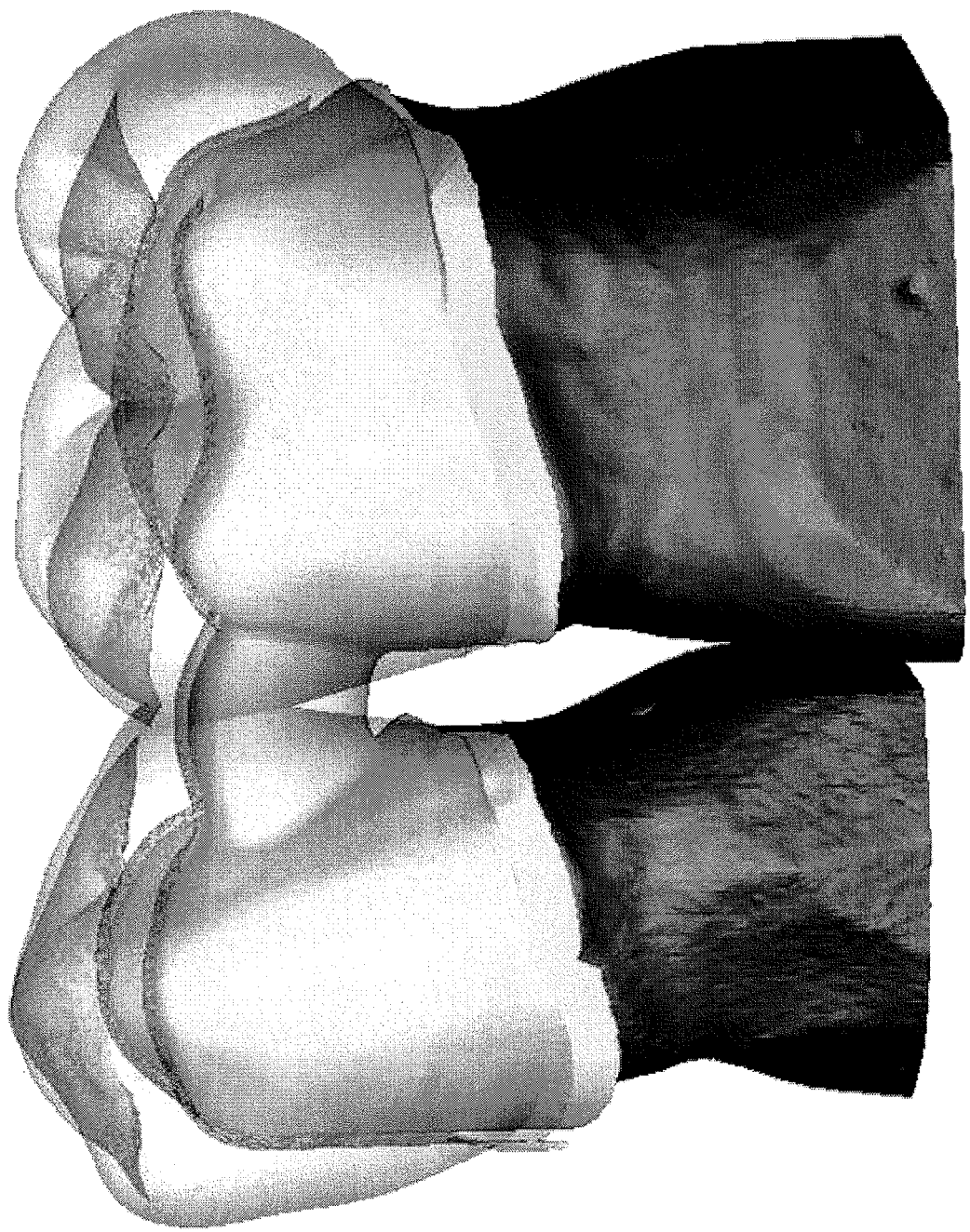
FIG. 52 is a perspective view of a splinted crown having a framework including two coping substructures coupled together by a connector.

The results of the first generate operation 2704 are shown in FIG. 51. FIG. 51 is a plan view of the abutment surface of the coping substructures 5120, 5130 arranged within first and second outer dental restoration 5112, 5116, respectively, of the bridge appliance 5110. In some embodiments, the first generate operation 2704 also defines initial crown superstructures corresponding to each of the copings substructures 5120, 5130. In other embodiments, however, only the coping substructures 5120, 5130 are produced.

A second generate operation 2706 generates the appropriate number of pontics. In some embodiments, the second generate operation 2706 may generate a pontic and a corresponding crown superstructure. In other embodiments, however, only the pontics are generated. In general, the second generate operation 2706 generates the pontics based on the exterior surface of the bridge appliance. For example, the second generate operation 2706 may generate the pontics in accordance with the constraints listed herein for generating the coping exterior surface of a dental restoration.

A third generate operation 2708 creates the connectors that couple together the components of the bridge framework. In one embodiment, the third generate operation 2708 creates the connectors based on the exterior surface of the crown top array or the bridge appliance. For example, the third generate operation 2708 may create connectors to fit within the contact area (i.e., interaction nexus) of each restoration pair of the bridge framework (e.g., see FIG. 28). In other embodiments, however, the connectors may be generated using any suitable process. The framework design process 2700 completes and ends at a stop module 2710.

Figure 28:
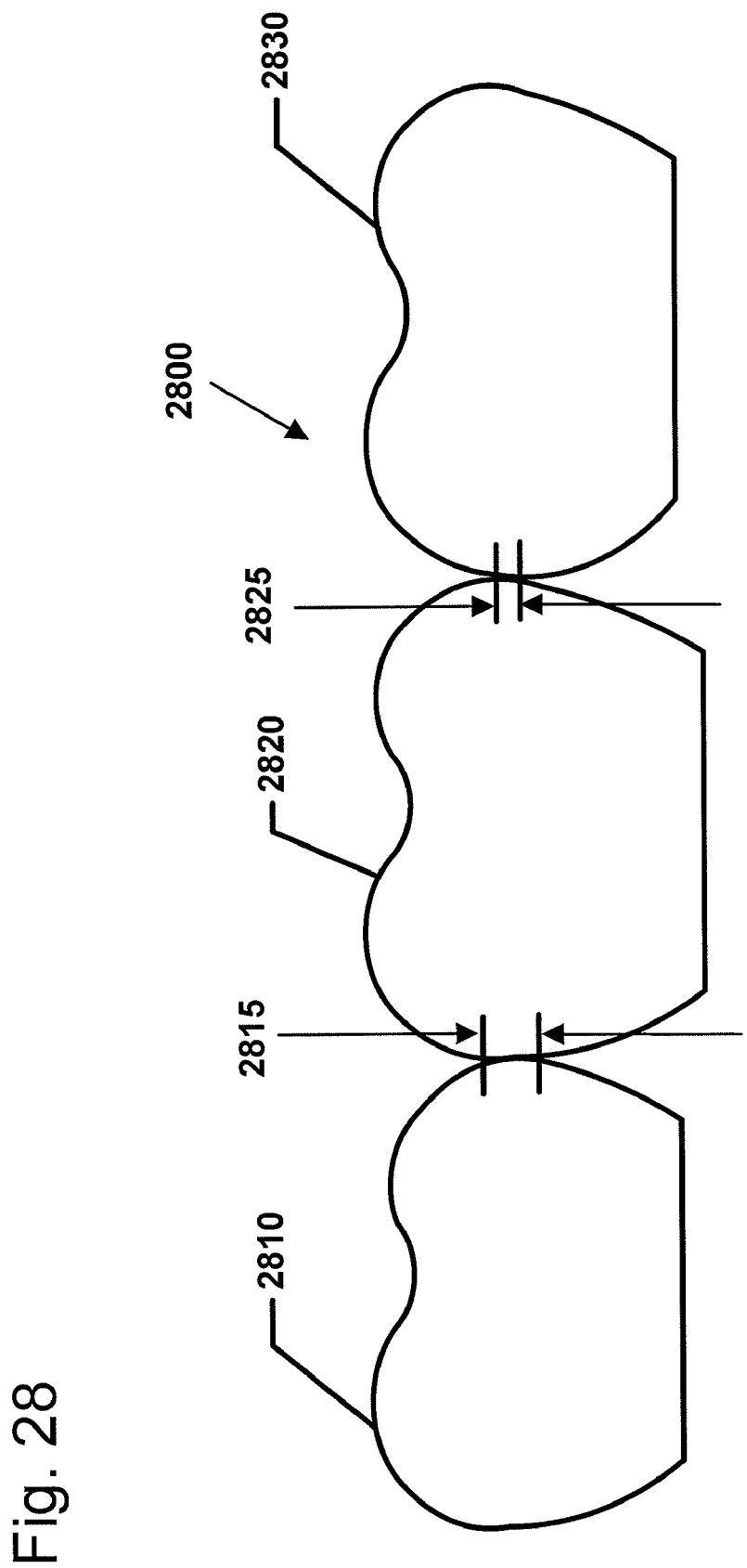
FIG. 28 is a schematic block diagram of a bridge appliance including three dental restorations interacting with each other at contact areas in accordance with the principles of the present disclosure.

FIG. 28 is a schematic block diagram of an exterior surface 2810 of a bridge appliance 2800 including three dental restorations 2810, 2820, 2830 that interact with each other at contact areas 2815, 2825. The shape and orientation of each contact area 2815, 2825 may vary with each restoration pair. Accordingly, the thickness of connectors generated to fit within the contact areas of the bridge exterior surface may vary along their lengths.

Figure 29:
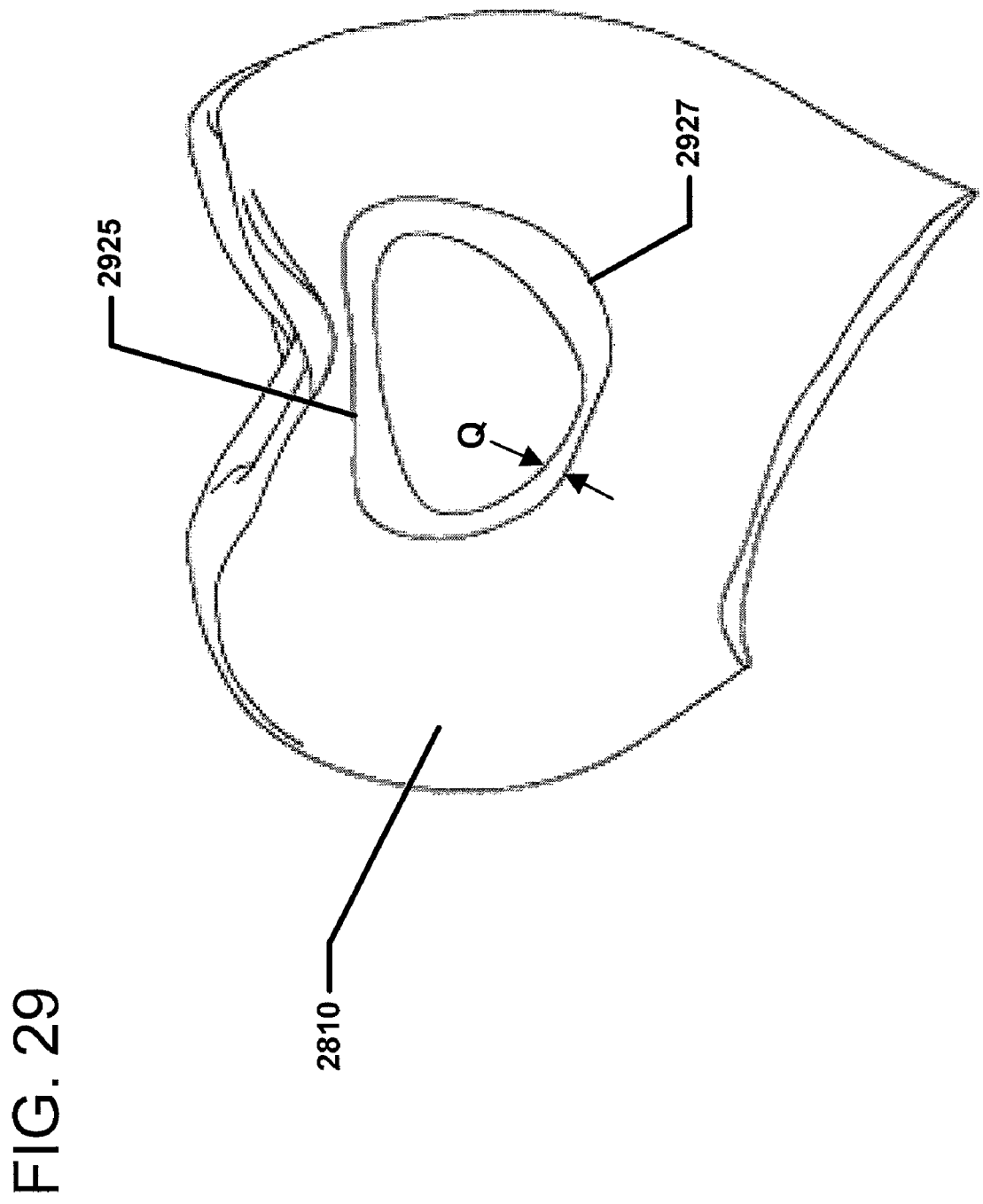
FIG. 29 is a side view of a dental restoration of a bridge appliance over which curves representing the contact area and the connector cross-section have been superimposed in accordance with the principles of the present disclosure.

FIG. 29 is a schematic block diagram of a side view of the first dental restoration 2810 of FIG. 28. A first curve 2925 representing the perimeter of the contact area 2815 between the first dental restoration 2810 and the second dental restoration 2820 is shown. A second curve 2927 representing the cross-sectional circumference of the connector 2923 is shown offset inwardly from the first curve 2925 by an amount Q. In one embodiment, the second curve 2927 is offset by an amount Q ranging from about 0.5 millimeters to about 1 millimeter.

Automated Design

Figure 30:
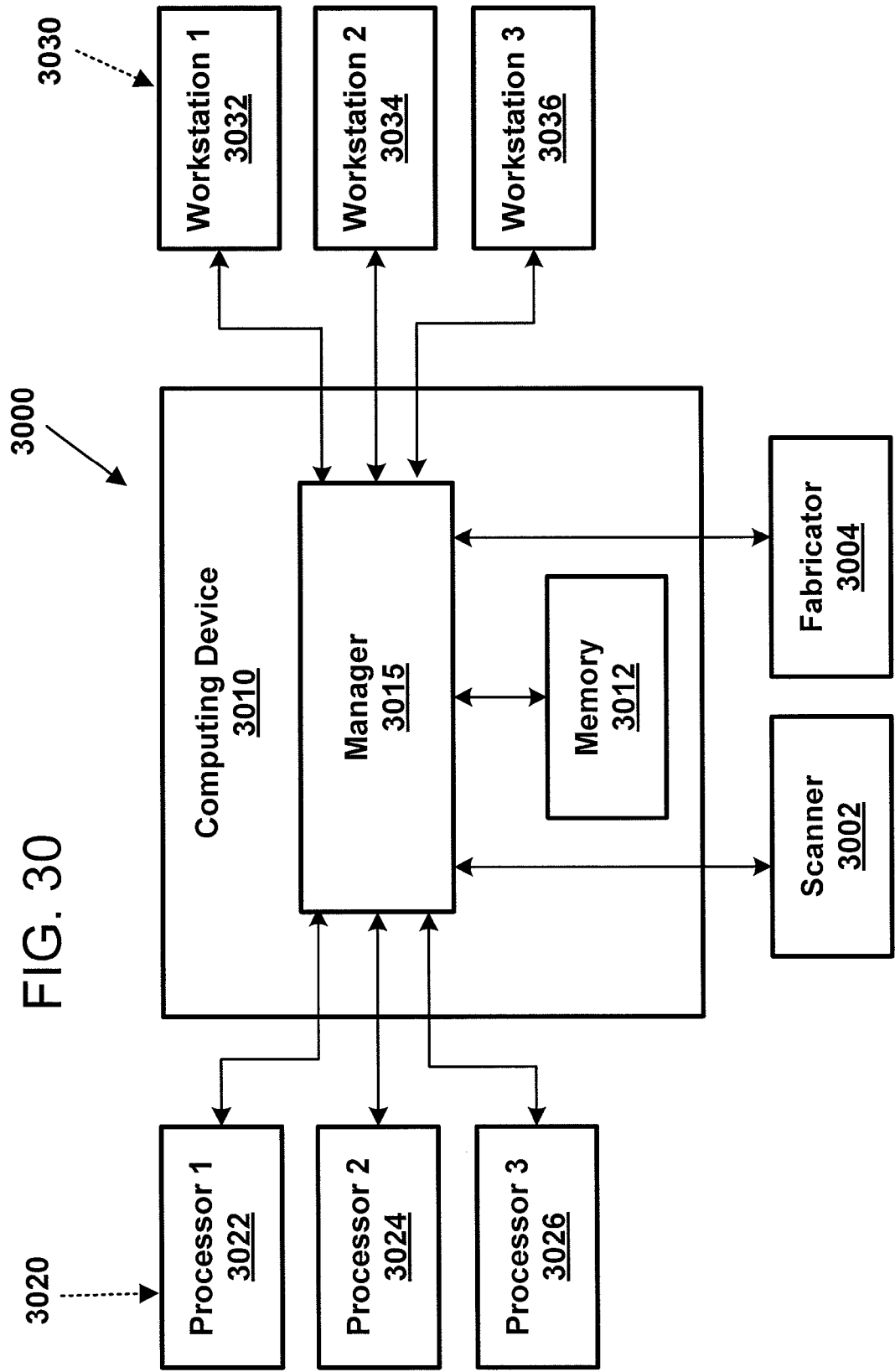
FIG. 30 is a schematic block diagram of a design and fabrication system that is configured to design and fabricate dental appliances in accordance with the principles of the present disclosure.

Referring to FIGS. 30-32(A-B), the generation of dental appliances may be at least partially automated. For example, one or more of the model generation processes may be performed automatically by a computer. Other model generation processes may be performed interactively with the user. Advantageously, partial automation significantly decreases the time a skilled technician spends on a given electronic model.

For example, in one embodiment, a dental technician may upload a first electronic model to a work station to interact with the first electronic model. The dental technician may send the first electronic model to a server for intelligent processing upon reaching a particular stage in the design process. The technician may proceed to work on another available electronic model while the server further processes the first electronic model. The same or another technician can return to working on the first electronic model at a later time when the first electronic model again becomes available.

Figure 32B:
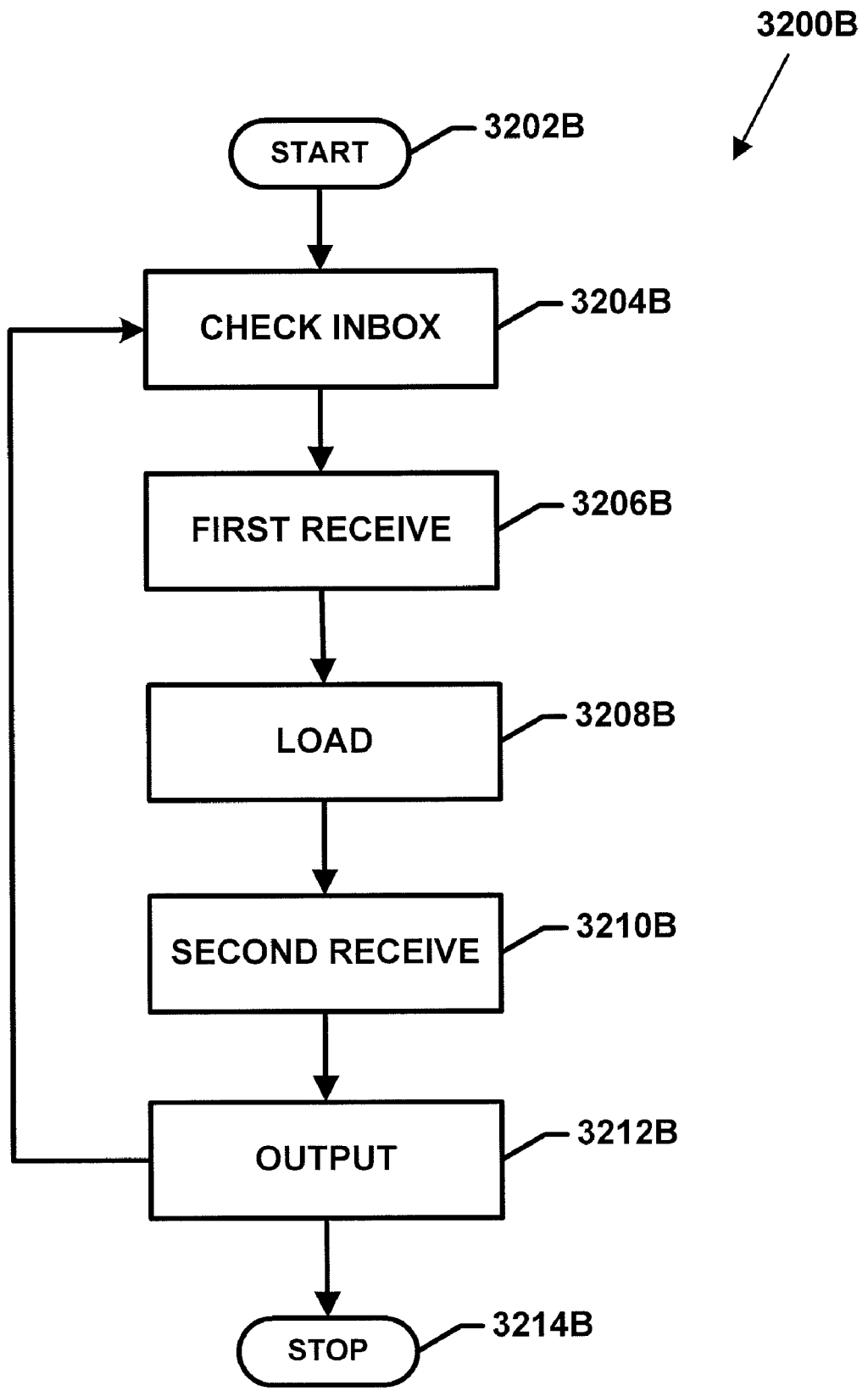
FIG. 32B is a flowchart illustrating an operational flow for an exemplary interaction process by which a technician or other user of the design and fabrication system may implement steps of the design and fabrication process of FIG. 31 in accordance with the principles of the present disclosure.

FIG. 30 is a schematic block diagram of a design and fabrication system 3000 that is configured to design and fabricate dental appliances in accordance with the principles of the present disclosure. FIGS. 31, 32A, and 32B are flowcharts illustrating operational flows for processes to be performed using the design and fabrication system 3000. FIG. 31 illustrates a design and fabrication process 3100 by which dental appliances may be designed and fabricated. FIG. 32A illustrates a management process 3200A by which one or more processors may implement steps of the design and fabrication process 3100. FIG. 32B illustrates an interaction process 3200 by which a technician or other user of the design and fabrication system 3000 may implement steps of the design and fabrication process 3100.

The design and fabrication system 3000 includes at least one scanner 3002, a computing device 3010, and at least one fabrication device 3004. The scanner 3002 is configured to obtain positional data pertaining to a preparation site and/or surrounding anatomy of the patient. Preferred scanners 3002 include a laser line scanner arranged and configured for scanning dental study casts. However, any suitable scanner (e.g., an optical scanner) may be used and a number of other scanning methodologies (e.g., direct intra-oral scanning) might be employed to generate the scanned image data.

The computing device 3010 is configured to receive from the scanner 3002 the positional data (e.g., 3D coordinate data) of the preparation site, to generate an electronic model of a dental appliance to be installed on the preparation site, and to send information obtained from the generated electronic model to the fabrication device 3004. One or more of these steps may be performed automatically, at least in part, by the computing device 3010. In other steps, user interaction may be appropriate as disclosed in greater detail herein. The computing device 3010 also provides a file management system for tracking the progress of electronic models and scheduling processor time for automated steps.

The fabrication device 3004 produces either the dental appliance or a pattern from which the dental appliance may be manufactured based on the electronic model. One non-limiting example of a suitable fabrication device includes a rapid prototyping machine. In one embodiment, the fabrication device 3004 prints one or more wax patterns of the dental appliance. The dental appliance may be manufactured from these wax patterns (e.g., through a lost-wax casting technique). In another embodiment, the fabrication device 3004 directly prints one or more pieces of the dental appliances out of metal, ceramic, or other suitable material. In another embodiment, the fabrication device 3004 mills one or more pieces of the dental appliance.

The computing device 3010 is communicatively coupled to one or more processors 3020 configured to perform automated processes on the electronic model. In one embodiment, the processors 3020 are installed within the computing device 3010. In other embodiments, however, the computing device 3010 may be coupled to one or more external processors 3020. In the example shown in FIG. 30, the computing device 3010 is communicatively coupled to a first external processor 3022, a second external processor 3024, and a third external processor 3026. One or more of the processors 3020 may be arranged at locations remote from the computing device 3010 and/or from each other.

The computing device 3010 also is communicatively coupled to one or more work stations 3030 through which a technician or other user may perform manual or interactive processes on the electronic model. In the example shown in FIG. 30, the computing device 3010 is communicatively coupled to a first workstation 3032, a second workstation 3034, and a third workstation 3036. In one embodiment, one or more workstations 3030 may be arranged at locations remote from the computing device 3010 and/or each other.

Each work station 3030 is configured to obtain one or more electronic models from the computing device 3010, to display the electronic models to a technician or other user, and to enable interactive editing of the electronic model by the technician. In one embodiment, each work station 3030 includes input and output devices for receiving editing instructions and displaying the results of the editing instructions to the technician.

In general, the file management system schedules processor time for performing any automated initial processing steps in generating the electronic models. Technicians can access the file management system from any of the work stations. Upon accessing the file management system, the technicians can view, select, and download electronic models to the work stations for further processing. Each electronic model may be passed between the processors and the workstations multiple times during the generation process. Accordingly, different technicians can edit the same electronic model at different times and/or in different places. Typically, each technician performs only a small number of processes on any one electronic model.

The computing device 3010 includes memory 3012 in which the scanned positional data and the generated electronic models can be stored. The computing device 3010 includes a manager 3015 that obtains information from the memory 3012 prior to processing (e.g., at the processor or the workstation) and stores information in the memory 3012 after processing. The file manager 3015 also supervises which processes are performed automatically by the processors 3020 and which processes are performed interactively with a user. The manager 3015 also schedules when the automated processes are performed and tracks each of the electronic models through the design and manufacturing process.

For example, when an electronic model is stored in the memory 3012 of the computing device 3010, the file manager 3015 of the file management system 3000 may determine the next stage in the process and send the electronic model to an available processor 3020 for further editing. The processor performs the next one or more processes that can be performed automatically. In one embodiment, the electronic model may be processed by more than one processor. When the automatic processes have been completed and additional processing is appropriate, the electronic model may be returned to the file management system and identified as available for interactive editing.

The principles of the design and fabrication system 3000 can be understood by walking through an example design and fabrication process 3100 (FIG. 31). The design and fabrication process 3100 enables a dental restoration having multiple pieces (e.g., a crown superstructure and a coping substructure) to be manufactured to suit the anatomy of a particular patient. The design and fabrication process 3100 initializes and begins at a start module 3102 and proceeds to a scan operation 3104.

The scan operation 3104 obtains positional data relating to a preparation site on which a dental appliance is to be mounted. In one embodiment, the scan operation 3104 obtains positional information from a dental impression (e.g., a plaster study cast). In another embodiment, the scan operation 3104 obtains positional information directly from the mouth of the patient (e.g., via intra-oral scanning). In one embodiment, the positional information includes adjacent teeth, antagonistic teeth, the edentulous tissue, and/or other surrounding anatomy.

A generate operation 3106 creates an electronic model of the preparation site based on the positional data obtained by the scan operation 3104. Typically, the generate operation 3106 is performed automatically. For example, the manager 3015 of the computing device 3010 may send the positional data obtained from the scanner 3002 to one or more of the processors 3020 to generate the electronic model. In one embodiment, the generate operation 3106 creates the electronic model of the preparation site including surrounding anatomy.

A detect operation 3108 finds and optionally marks (e.g., annotates) landmarks (e.g., a margin curve, collar location and/or dimensions, etc.) on the electronic model of the preparation site. In one embodiment, the detect operation 3108 also finds and optionally marks (e.g., annotates) landmarks (e.g., heights of contour, cusps, and fossae, on adjacent teeth) on the surrounding anatomy. The detect operation 3108 may determine trends in landmarks for adjacent teeth (e.g., curvature of ridges, reduction or increase in height, etc.). Typically, the detect operation 3108 is performed automatically. In one embodiment, the manager 3015 schedules the detect operation 3108 to be performed immediately after the generate operation 3106. In another embodiment, the manger 3015 schedules the detect operation 3108 to be performed at a later time and/or on a different processor.

A modify operation 3110 presents an electronic model to a user and enables the user to manipulate the electronic model. Typically, the modify operation 3110 enables the user to adjust changes and/or additions previously made to the electronic model by the processors. For example, the user may adjust the shape, size, color, texture, landmarks, or other attribute of the electronic models. Typically, the modify operation 3110 is implemented by a technician on a work station. Alternatively, however, the modify operation 3110 may be implemented on the computer device 3010 using input devices of the computer device 3010.

At this stage of the example application, the modify operation 3110 presents the electronic model of the preparation site to a technician for review. In general, this modify operation 3110 sends the electronic model of the preparation site to one or more of the workstations 3030 for display to the technician. In one embodiment, the modify operation 3110 presents annotated landmarks to the technician with the electronic model. The first modify operation 3110 also may receive instructions from the user (e.g., via an input device of the workstation 3030) adjusting the identification of the landmarks, deleting landmarks, and/or identifying additional landmarks.

For example, a technician may choose to define the margin curve of the preparation site differently than the automated detection process. In one embodiment, the user may redraw the annotation indicating the margin curve using an input device during the modify operation 3110. In another embodiment, the user may drag portions of the annotated landmark, such as a diagramming line, to more appropriate positions on the electronic model. In another embodiment, the user may add new annotations to identify additional landmarks and/or delete current annotations.

A receive operation 3112 enables the technician to provide additional input effecting the generation of subsequent electronic models. For example, in one embodiment, the receive operation 3112 may receive instructions from the technician indicating a fabrication material for one or more components for which electronic models are to be generated. Different fabrication materials may have different constraints (e.g., maximum thickness, minimum thickness, etc.) to be met. Accordingly, the component electronic models may be generated based on the input fabrication material. In other embodiments, the receive operation 3112 determines default values or the technician may choose not to provide instructions at one or more stages of the design process.

A build operation 3114 creates an electronic model of the dental appliance or component thereof based on the modified electronic model and the user input. In general, the build operation 3114 is performed automatically by one or more processors 3020. For example, at this stage of the example application, the build operation 3114 may generate an electronic model of a dental restoration shaped and dimensioned to fit the patient anatomy surrounding the preparation site. In a preferred embodiment, the build operation 3114 generates an exterior surface of the dental appliance including an occlusal surface and sidewalls.

In some embodiments, the build operation 3114 obtains an electronic model template of the dental appliance to be designed. In one embodiment, the build operation 3114 obtains a parametric model template having attribute values assigned based on the landmarks detected in the detect operation 3108, reviewed in the modify operation 3110, and/or input in the receive operation 3112. In another embodiment, the build operation 3114 may be performed automatically before the user reviews the identified landmarks in the modify operation 3110 or before the user inputs additional instructions in the receive operation 3112. In other embodiments, the build operation 3114 generates the dental appliance using other suitable processes.

A first determination module 3116 determines whether all components of the dental appliance have been generated. For example, in one embodiment, when designing a bridge framework, the first determination module 3116 may determine whether electronic models for all coping substructures, pontics, connectors, and crown tops have been created. If the first determination module 3116 determines electronic models for all components have been generated, then the design and fabrication process 3100 proceeds to a verify operation 3118. If the first determination module 3116 determines electronic models for all components have not been generated, however, then the design and fabrication process 3100 may cycle back to the modify operation 3110 (see the solid arrow at N1). In an alternative embodiment, the design and fabrication process 3100 may cycle back to the receive operation 3112 (see the dotted arrow at N2).

The design and fabrication process 3100 may cycle iteratively through the modification operation 3110, the receive operation 3112, and the build operation 3114 to produce different components of a dental appliance. These operations 3110, 3112, 3114 represent conceptual steps in the design process and do not imply the same software or algorithms are applied each time the operation is performed. Rather, different algorithms may be applied by these operations 3110, 3112, 3114 depending on the current stage of the design process. For example, the build operation 3114 may create a first electronic model (e.g., of a dental restoration) by obtaining a template for the exterior surface of the dental restoration during one iteration and may create another electronic model (e.g., a coping exterior surface) during a subsequent iteration by generating the electronic model based on previously obtained positional and/or landmark data.

At this stage of the example application, the first determination module 3116 determines that neither a coping substructure nor a crown superstructure have been generated for the dental restoration. Accordingly, the first determination module 3116 determines the design process is not complete. In the example shown in FIG. 31, the design process 3100 cycles back to the modify operation 3110 for another iteration. In one embodiment, the design process 3100 skips the modify operation 3110 and receive operation 3112 and proceeds directly to the build operation 3114 for a second iteration (see the dotted arrow at N3).

In another embodiment, however, the modify operation 3110 presents the dental appliance electronic model to the user for review and/or interactive editing during the second iteration. In a preferred embodiment, the modify operation 3110 presents the exterior surface of the dental appliance including the occlusal surface and sidewalls. For example, the modify operation 3110 may provide the dental appliance electronic model to one or more of the workstations 3030 for display. The modify operation 3110 also may receive instructions from the technician scaling, transforming, or otherwise adjusting the electronic model of the exterior surface.

The receive operation 3112 may receive any input from the user relevant to generating the next electronic model and the build operation 3114 creates the next electronic model. In this example application, the second iteration of the build operation 3114 generates an abutment surface of the dental restoration. The first determination module 3116 determines additional processing is necessary and cycles back to the modify operation 3110 for a third iteration.

In one embodiment, the third iteration of the modify operation 3110 presents the newly generated abutment surface model to the technician and enables the technician to adjust the abutment surface. Also during the third iteration, the receive operation 3112 may receive instructions from the technician indicating a location and/or dimensions for a collar to be defined on a coping substructure. The third iteration of the build operation 3114 may generate an exterior surface of a coping substructure based on the previously obtained electronic models and/or the previously received user input. The build operation 3114 also may combine the coping exterior surface with the abutment surface to form an electronic model of a coping substructure.

In the example application, the fourth iteration of the modify, receive, and build operations 3110, 3112, 3114 yields an interior surface of the crown superstructure, which may be combined with the exterior surface of the dental restoration to form an electronic model of the crown superstructure. During additional iterations of these operations 3110, 3112, 3114, additional feature to the electronic model, such as the tabs, sprue formers, and/or identification numbers disclosed herein, may be added. When the additional features have been added, the first determination module 3116 determines the design phase of the design and fabrication process 3100 is complete. Accordingly, the process 3100 proceeds to the verify operation 3118.

The verify operation 3118 may provide quality control by presenting the completed electronic models of the dental appliance to the technician. In general, the verify operation 3118 presents the electronic models of the dental appliance to one or more technicians to enable the technicians to decide whether the dental appliance is ready for fabrication. For example, the verify operation 3118 may enable the technician to select whether to view the components separately or arranged together to view interaction between the components. In one embodiment, the verify operation 3118 presents the electronic models to a technician at a location remote from the location at which the electronic models were designed and/or modified, thereby allowing for remote supervision of the design process.

A second determination module 3120 determines whether the technician approved the electronic models of the dental appliance during the verify operation 3118. For example, the second determination module 3120 may determine the technician provided instructions to proceed with fabrication. Alternatively, the second determination module 3120 may determine the technician provided instructions to perform one or more adjusts on the electronic models or to redo the entire design process 3100.

If the second determination module 3120 determines the technician did not approve the electronic model, then the design and fabrication process 3100 may cycle back to the modify operation 3110 to enable a technician to adjust the electronic models in accordance with the verifying technician instructions. Alternatively, the second determination module 3120 may scrap the electronic models of the dental appliance and restart at the modification operation 3110 with only the scanned positional data.

If the second determination module 3120 determines the technician did approve the electronic model, however, then the design and fabrication process 3100 may proceed to a fabricate operation 3122. The fabricate operation 3122 transmits the electronic models to a fabricator (e.g., fabricator 3004 of FIG. 30) to produce components of the dental appliance based on the electronic models. In one embodiment, the fabricate operation 3122 finalizes the electronic models (e.g., optimizes the model meshes, adds fabrication supports, and/or translates the electronic model to a format suitable for fabrication) before sending the models to the fabricator 3004. For example, in one embodiment, the fabricate operation 3122 may print patterns of the dental appliance components. In another embodiment, the fabricate operation 3122 may print and/or mill the actual dental appliance components. The design and fabrication process 3100 completes and ends at a stop module 3124.

FIG. 32A is a flowchart illustrating an operational flow for a management process 3200A by which the manager 3015 of the design and fabrication system 3000 implement steps of the design and fabrication process 3100. The management process 3200A initializes and begins at a start module 3202A and proceeds to a process operation 3204A.

The process operation 3204A schedules time with one or more processors 3020 of the design and fabrication system 3000 for performing one or more of the automated steps (e.g., the scan operation 3104, the generate operation 3106, the detect operation 3108, the build operation 3114, and the fabricate operation 3116) of the design and fabrication process 3100 (see the first dotted line section of FIG. 31). In one embodiment, the process operation 3204A schedules the same processor 3020 to perform multiple sequential steps. In another embodiment, the process operation 3204A schedules different processors (e.g., at different locations) to perform different steps.

A store operation 3206A receives the processed electronic models (i.e., or positional data if the generate step 3106 has not yet been performed) and stores the information in memory 3012. The store operation 3206A also may update a status log to indicate a current placement of the electronic model within the design process. In one embodiment, if the next step to be performed is an interactive step (see second dotted line section of FIG. 31), then the store operation 3206A may store metadata with the electronic model indicating the electronic model is available for interactive processing.

A first receive operation 3208A receives a request for one of the electronic models. For example, the first receive operation 3208A may receive a request from one of the work stations 3030 to transmit a partially completed electronic model of a dental appliance. In one embodiment, the first receive operation 3208A may first receive a request for a status listing of each electronic model stored on the computer system 3010. In another embodiment, the first receive operation 3208A may receive a request for a listing of electronic models available for interactive processing.

In response, a present operation 3210A sends the requested electronic model to the requesting technician. For example, the present operation 3210A may transmit the requested electronic model to the requesting work station 3030 via a networking environment (e.g., a LAN, a WAN, the Internet, etc.). In another embodiment, the present operation 3210A allows the work station 3030 to pull the electronic model from memory 3012.

A second receive operation 3212A subsequently obtains the electronic model back from the technician. For example, in one embodiment, the second receive operation 3212A may receive a modified version of the electronic model. In another embodiment, the second receive operation 3212A may receive additional information (e.g., metadata about the electronic model, instructions for another technician to modify one or more components of the electronic model, etc.). In one embodiment, the second receive operation replaces a copy of the electronic model in memory with the received modified copy.

A determination module 3214A determines whether processing of the electronic model has been completed (e.g., the electronic model is ready for fabrication). If the determination module 3214A determines the processing has not been completed, then the management process 3200A cycles back to the process operation 3204A to begin again. If the determination module 3214A determines the processing has been completed, however, then the management process 3200A completes and ends at a stop module 3216A. In one embodiment, completing the management process includes sending the electronic model to a fabricator.

FIG. 32B is a flowchart illustrating an exemplary interaction process 3200B by which a technician may perform one of the operation (e.g., operation 3110, receive operation 3112, or verify operation 3118 of FIG. 31) using the design and fabrication system 3000. The interaction process 3200B initializes and begins at a start module 3202B and proceeds to a check operation 3204B.

The check operation 3204B determines whether any electronic models are available for editing. For example, the check operation 3204B may determine whether any electronic models have arrived at one of the interactive steps of the design and fabricate process 3100 of FIG. 31. In one embodiment, the check operation 3204B determines whether any electronic models are indicated by the manager 3015 of the computer device 3010 as ready for review or interactive editing. Available electronic models may be displayed to the technician.

A first receive operation 3206B receives a selection of an available electronic model from the technician. In one embodiment, the first receive operation 3206B receives a selection from a technician at a first workstations 3032 coupled to the file management device 3010. A load operation 3208B obtains (e.g., downloads) the selected electronic model to the first workstation 3032 from the file management device 3010. A second receive operation 3210B obtains editing instructions from the technician. For example, the second receive operation 3210B may receive editing instructions at the first workstation 3032. An output operation 3212B sends the edited electronic model back to the file management device 3010 for storage. The editing process 3200B completes and ends at a stop module 3214.

In still other embodiments, other dental appliances, such as implants or custom abutments can be produced using the processed described herein. The disclosure is not limited to the type of dental appliance designed. Additional details describing the design of dental appliances having multiple components can be found, e.g., in the Ser. No. 11/186,391 application noted above.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A method for designing a dental restoration having a coping substructure and a crown superstructure, the method comprising:
   providing an electronic model of a preparation site onto which the dental restoration is to be installed, the electronic model of the preparation site including surrounding anatomy;
   obtaining an electronic model of an exterior surface of the dental restoration based on the surrounding anatomy;
   generating an abutment surface of the dental restoration based on the preparation site;
   generating a coping exterior surface based on a first offset from the abutment surface of the dental restoration;
   deforming the coping exterior surface based on constraints related to the coping substructure or the crown superstructure to form a finalized coping exterior surface;
   combining the finalized coping exterior surface with the abutment surface to form an electronic model of the coping substructure;
   generating a crown interior surface based on a second offset from the finalized crown exterior surface; and
   combining the crown interior surface with the crown exterior surface to form an electronic model of the crown superstructure.

2. The method of claim 1, further comprising:
   fabricating the coping substructure; and
   fabricating the crown superstructure.

3. The method of claim 1, wherein generating the coping exterior surface based on the first offset from the abutment surface comprises generating the coping exterior surface based on a generally uniform offset from the abutment surface.

4. The method of claim 1, wherein deforming the coping exterior surface based on constraints comprises:
   determining a maximum thickness of the crown superstructure;
   determining a minimum thickness of the crown superstructure;
   deforming the coping exterior surface outwardly toward the crown exterior if a distance between the coping exterior surface and the crown exterior surface exceeds the maximum thickness of the crown superstructure; and
   deforming the coping exterior surface inwardly away from the crown exterior if the distance between the coping exterior surface and the crown exterior surface does not meet the minimum thickness of the crown superstructure.

5. The method of claim 1, wherein deforming the coping exterior surface based on constraints further comprises:
   determining a minimum thickness of the coping substructure; and
   deforming the coping exterior surface outwardly toward the crown exterior if a distance between the coping exterior surface and the abutment surface exceeds the maximum thickness of the crown superstructure.

6. A method for designing a dental bridge having a framework and a crown top array, the method comprising:
   providing an electronic model of a dentition of a patient including at least a first preparation site and a gap of edentulous tissue onto which the dental bridge is to be installed, the electronic model of the dentition further including surrounding anatomy;
   obtaining an electronic model of an exterior surface of the dental bridge based at least partially on the surrounding anatomy, the exterior surface of the dental bridge defining exterior surfaces for at least a first tooth and a second tooth;
   generating an electronic model of a bridge framework based on the electronic model of the exterior surface of the dental bridge including generating an electronic model of at least a first coping substructure, an electronic model of at least a first pontic, and an electronic model of at least a first connector to extend between the first coping substructure and the first pontic, wherein generating the electronic model of at least the first coping substructure comprises:
      generating an abutment surface of the first tooth of the exterior surface based on the preparation site;
      generating a coping exterior surface of the first coping substructure based on a first offset from the abutment surface of the first tooth;
      deforming the coping exterior surface based on constraints related to the coping substructure or the exterior surface to form a finalized coping exterior surface;
      combining the finalized coping exterior surface with the abutment surface to form an electronic model of the coping substructure;
   wherein the first connector is generated based on a contact area of the first and second teeth on the exterior surface of the dental bridge.

7. The method of claim 6, wherein the first pontic is generated based on the exterior surface of the dental bridge representing the second tooth.

8. The method of claim 6, further comprising:
   receiving instructions indicating an appropriate number of coping substructures and an appropriate number of pontics to form the bridge framework, wherein obtaining the electronic model of the exterior surface of the dental bridge comprises obtaining the electronic model including the appropriate number of coping substructures and the appropriate number of pontics.

* * * * *